(12) United States Patent
Sinha Roy et al.

(10) Patent No.: US 7,928,058 B2
(45) Date of Patent: Apr. 19, 2011

(54) PHARMACEUTICAL COMPOSITION COMPRISING OXYNTOMODULIN DERIVATIVES AND A METHOD FOR REDUCING BODY WEIGHT USING THE COMPOSITION

(75) Inventors: Ranabir Sinha Roy, Edison, NJ (US); Elisabetta Bianchi, Rome (IT); Antonello Pessi, Rome (IT); Paolo Ingallinella, Pomezia (IT); Donald J. Marsh, Hillsborough, NJ (US); George J. Eiermann, Marlboro, NJ (US); Yingjun Mu, Fanwood, NJ (US); Yun-Ping Zhou, East Brunswick, NJ (US)

(73) Assignees: Merck Sharp & Dohme Corp., Rahway, NJ (US); Istituto Di Ricerche Di Biologia Molecolare P. Angeletti S.p.A., Pomezia (Roma) (IT)

( * ) Notice: Subject to any disclaimer, the term of this patent is extended or adjusted under 35 U.S.C. 154(b) by 22 days.

(21) Appl. No.: 12/223,942

(22) PCT Filed: Feb. 16, 2007

(86) PCT No.: PCT/US2007/004306
§ 371 (c)(1),
(2), (4) Date: Aug. 13, 2008

(87) PCT Pub. No.: WO2007/100535
PCT Pub. Date: Sep. 7, 2007

(65) Prior Publication Data
US 2010/0144617 A1    Jun. 10, 2010

Related U.S. Application Data

(60) Provisional application No. 60/775,544, filed on Feb. 22, 2006, provisional application No. 60/834,452, filed on Jul. 31, 2006.

(51) Int. Cl.
*A61K 38/00* (2006.01)
(52) U.S. Cl. ........ 514/1.1; 514/11.7; 514/21.3; 530/300
(58) Field of Classification Search ........................ None
See application file for complete search history.

(56) References Cited

U.S. PATENT DOCUMENTS

| 6,271,011 | B1 * | 8/2001 | Lee et al. ....................... 435/200 |
| 6,692,923 | B2 * | 2/2004 | Lal et al. ......................... 435/7.1 |
| 7,666,835 | B2 * | 2/2010 | Bloom et al. .................... 514/12 |

FOREIGN PATENT DOCUMENTS

| WO | WO 01/83527 | 11/2001 |
| WO | WO 2004/062685 | 7/2004 |
| WO | WO 2006/134340 | 12/2006 |
| WO | WO 2007/056362 | 5/2007 |

OTHER PUBLICATIONS

Dakin et al., End.145: 2687-2695, 2004.*
Hinke et al., J. Biol. Chem., vol. 275 (2000), pp. 3827-3834, "Dipeptidyl peptidase IV (DPIV/CD26) degradation of glucagon".

* cited by examiner

*Primary Examiner* — Robert Landsman
*Assistant Examiner* — Gyan Chandra
(74) *Attorney, Agent, or Firm* — John David Reilly; John C. Todaro

(57) ABSTRACT

Modified oxyntomodulin derivatives. Such derivatives can be used for the treatment of metabolic diseases such as diabetes and obesity.

18 Claims, 17 Drawing Sheets

| PEG Positional Scan on [Aib²] – Oxm |||||
|---|---|---|---|---|
|  | GLP-1R EC$_{50}$(nM) | GCG-R EC$_{50}$(nM) | Activation % | GLP-1R/GCGR |
| OXM | 9.2 | 0.6 | (87) | +/+ |
| OXM Aib² | 0.5 | 68.4 | (95) | +/+ |
| OXM99  (C38) 40K | 6.1 | >1000 | (66) | +/− |
| OXM100 (C38) 60K | 22.5 | >1000 | (22) | +/− |
| OXM103 (C20) 40K | 6.2 | 5.5 | (73) | (+/+) |
| OXM105 (C21) 40K | 28.5 | 648 | (21) | +/− |
| OXM107 (C24) 40K | 35.2 | >1000 | (30) | +/− |
| OXM109 (C28) 40K | 7.6 | >1000 | (65) | +/− |

FIG.14

| Oxm: Truncation analysis | | | | |
|---|---|---|---|---|
| Peptide | Sequence | GLP-1R (nM) | GcgR (nM) | Activation % |
| OxmOH | HSQGTFTSDYSKYLDSRRAQDFVQWLMNTKRNRNNIA | 13.8 | 0.6 | (87) |
| OxmNH$_2$ | HSQGTFTSDYSKYLDSRRAQDFVQWLMNTKRNRNNIA | 9.2 | 5.5 | (100) |
| Oxm25 | HSQGTFTSDYSKYLDSRRAQDFVQWLMNTKRNRNNI | 31.7 | 3.1 | (102) |
| Oxm26 | HSQGTFTSDYSKYLDSRRAQDFVQWLMNTKRNRNN | 16.0 | 2.3 | (99) |
| Oxm27 | HSQGTFTSDYSKYLDSRRAQDFVQWLMNTKRNRN | 13.4 | 1.7 | (101) |
| Oxm90 | HSQGTFTSDYSKYLDSRRAQDFVQWLMNTKRNR | <3.2 | 1.3 | (84) |
| Oxm91 | HSQGTFTSDYSKYLDSRRAQDFVQWLMNTKRN | <3.2 | 0.57 | (95) |
| Oxm92 | HSQGTFTSDYSKYLDSRRAQDFVQWLMNTKR | <0.13 | 0.26 | (115) |
| Oxm93 | HSQGTFTSDYSKYLDSRRAQDFVQWLMNTK | <0.13 | 0.13 | (100) |
| GcgOH | HSQGTFTSDYSKYLDSRRAQDFVQWLMNT | NA | 0.14 | (100) |

FIG. 16

| Peptide | EC50 (hGLP-1R), nM | | EC$_{80}$ (hGcgR) |
|---|---|---|---|
| | "-DPP-IV" | "+DPP-IV" | nM |
| OXM99 | 7.5 | 27.5 | >1000 |
| OXM100 | 22.5 | 184.5 | >1000 |
| OXM103 | 6.2 | 12.7 | 5.5 |
| OXM105 | 28.5 | 36.7 | 648 |
| OXM107 | 29.7 | 182.4 | >1000 |
| OXM109 | 7.6 | 14.5 | >1000 |
| OXM110 | 0.2 | 0.08 | 0.61 |
| OXM112 | 6.9 | 10.9 | 164 |
| OXM113 | 93.3 | 92.3 | >1000 |
| OXM114 | 0.06 | 0.05 | 34.1 |
| OXM117 | 9.2 | 41.3 | >1000 |
| OXM118 | 0.025 | <0.5 | 538 |
| OXM121 | >125 | >125 | >1000 |
| OXM124 | >100 | >100 | >1000 |
| OXM125 | 3.9 | 42.5 | >1000 |
| OXM127 | >500 | >500 | >1000 |
| OXM129 | 25.0 | 123.2 | >1000 |
| OXM130 | 5.8 | 8.7 | PENDING |
| OXM131 | 0.9 | 2.2 | PENDING |

FIG.17

PHARMACEUTICAL COMPOSITION COMPRISING OXYNTOMODULIN DERIVATIVES AND A METHOD FOR REDUCING BODY WEIGHT USING THE COMPOSITION

CROSS REFERENCE TO RELATED APPLICATIONS

This patent application claims benefit of International Patent Application No. PCT/US2007/004306, which was filed 16 Feb. 2007 and which claims benefit of U.S. Provisional Application No. 60/775,544, filed 22 Feb. 2006, and U.S. Provisional Application No. 60/834,452, filed 31 Jul. 2006.

FIELD OF THE INVENTION

The present invention relates to oxyntomodulin derivatives, their synthesis, and their use for the treatment of metabolic disorders such as diabetes and obesity.

REFERENCE TO SEQUENCE LISTING SUBMITTED ELECTRONICALLY

The sequence listing of the present application is submitted electronically via EFS-Web as an ASCII formatted sequence listing with a file name "MRLDOB22046USPCT-SEQTXT-30APR2010.txt", creation date of Apr. 30, 2010, and a size of 114 KB. This sequence listing submitted via EFS-Web is part of the specification and is herein incorporated by reference in its entirety.

BACKGROUND OF THE INVENTION

The hormone oxyntomodulin (OXM, glucagon-37) is a posttranslational product of preproglucagon processing in the intestine and central nervous system (CNS) and is secreted from L-cells in the gut in response to food intake. Discovered in 1983, OXM has been implicated in the regulation of food intake and energy expenditure. Central or peripheral administration of OXM in rats causes a decrease in short term food intake with minimal effects on gastric emptying (Dakin et al. *Endocrinology*, 142:4244-4250 (2001), Dakin et al. *Endocrinology*, 145:2687-2695 (2004)). Repeated intracerebroventricular administration of OXM in rats results in elevated core temperatures and reduced weight gain compared to pair-fed animals, suggesting effects on both caloric intake and energy expenditure (Dakin et al. *Am. J. Physiol. Endocrinol. Metab.*, 283:E1173-E1177 (2002)).

OXM is a 37-amino acid peptide. It has been reported that the effects of OXM in inhibiting gastric acid secretion can be mimicked by the 8-residue C-terminal fragment Oxm(30-37), known as SP-1 (Caries-Bonnet et al., *Peptides*, 1996, 17:557-561. In humans, a single 90 min intravenous infusion of OXM in normal weight healthy subjects reduced hunger scores and food intake at a buffet meal by ~19%. Cumulative 12 hour caloric intake was reduced by ~11% with no reports of nausea or changes in food palatability (Cohen et al., *J. Clin. Endocrinol. Metab.*, 88:4696-4701 (2003)). More recently, pre-prandial injections of OXM over a 4 week period in obese healthy volunteers (BMI ~33) led to a significant reduction of caloric intake on the first day of treatment (~25%) that was maintained over the course of the study (35% reduction after 4 weeks) (Wynne et al., *Diabetes* 54:2390-2395 (2005)). Robust weight loss was observed at the end of the study in treated subjects (1.9%, placebo-corrected). Plasma levels of OXM were similar to that observed in the infusion study (peak concentration ~950 pM). The absence of any tachyphylaxis and a low incidence of mild and transient nausea (~3%) despite the relatively high doses necessitated by the poor in vivo stability of OXM (plasma $t_{1/2}$<12 min) renders this hormone one of the few obesity targets with both human validation and an attractive tolerability profile.

OXM has a very short half-life and is rapidly inactivated by the cell surface dipeptidyl peptidase IV (hereafter DP-IV). However, DP-IV inhibitors are weight-neutral in the clinic, suggesting that supraphysiological levels of OXM (900-1000 pM) may be required to achieve weight loss in humans.

Oxyntomodulin therefore shows potential as a treatment for metabolic disorders such as diabetes and obesity. However, because of the poor in vivo stability of OXM, there exists a need to develop OXM derivatives that can be safely and efficaciously administered for the treatment of metabolic diseases, such as diabetes and obesity. It would be further desirable if analogs or derivatives were developed that were modified by conjugation to moieties that would improve stability and pharmacokinetics, more particularly modifications that confer resistance to DP-IV cleavage. The instant invention provides OXM polypeptide derivatives and methods for the treatment or prevention of metabolic disorders such as obesity and diabetes by administering the derivatives described herein.

SUMMARY OF THE INVENTION

The present invention provides a polypeptide comprising:

(SEQ ID NO: 160)
$H_xX_1X_2GTFTSDYX_3X_4YLDX_5X_6X_6AX_7X_8FVX_7WLX_9X_{10}X_{11}K$ $RNRNNX_{12}X_{13}X_{14}$, wherein $H_x$ is selected from the group consisting of His; imidazole-lactic acid (ImiH); desamino-His ($\Delta NH_2$-H); acetyl His; pyroglutamyl His (PyrH); N-methyl-His (Me-H); N,N-dimethyl-His ($Me_2$-H); Benzoyl His (Bz-H); Benzyl His (Bzl-H); and Phe;

$X_1$ is selected from the group consisting of Ser; Gly; Ala; Arg; Asn; Asp; Glu; Gln; His; Ile; Lys; Met; Phe; Pro; Thr; Trp; Tyr; Val; D-Ala; D-Ser; and α-aminoisobutyric acid;

$X_2$ is Gln, Asp, Glu, Pro, Leu or L-norleucine;

$X_3$ is Ser, Ala, Cys, Cys(mPEG), or Cys(cholesteryl);

$X_4$ is Lys, Cys, Cys(mPEG), or Cys(cholesteryl);

$X_5$ is Ser or Ala;

$X_6$ is any amino acid;

$X_7$ is Gln, Cys, Cys(mPEG), or Cys(cholesteryl);

$X_8$ is Asp, Cys, Cys(mPEG), or Cys(cholesteryl);

$X_9$ is Met, Met(O), Val, norleucine, alanine, α-aminoisobutyric acid or O-methyl-homoserine;

$X_{10}$ is Asn, Cys, Cys(mPEG), or Cys(cholesteryl);

$X_{11}$ is Thr, Cys, Cys(mPEG), or Cys(cholesteryl);

$X_{12}$ is Ile, Cys, Cys(mPEG), or Cys(cholesteryl);

$X_{13}$ is Ala, Cys, Cys(mPEG), or Cys(cholesteryl); and $X_{14}$ is amide, carboxylate, secondary amide, Ala, K(palmitoyl), Cys, Cys(mPEG), Cys(cholesteryl) or any linker to which mPEG or cholesterol is linked with a chemical bond. Pharmaceutically acceptable salts thereof are contemplated as well.

Additionally, any one or two of $X_3$, $X_4$, $X_6$-$X_8$, and $X_{10}$-$X_{14}$ may be Cys(mPEG) Cys(cholesteryl); Cys(mPEG)teine may also be $C_1$; $C_2$; $C_3$ or $C_6$, wherein $C_1$=Cys(mPEG)$_5$ kDa, $C_2$=Cys(mPEG)20 kDa, $C_3$=Cys(mPEG)$_2$40 kDa, $C_6$=Cys (MPEG)$_2$60 kDa and each corresponds to a cysteine residue PEGylated via the side chain thiol with linear methoxyPEG (mPEG) or branched mPEG$_2$ of the indicated molecular weight.

The present invention relates to OXM polypeptide derivatives of the formula:

HαDGTFTSDYSKYLDSRRAQDFVQWLmNTKRNRNNIAC$_3$ (SEQ ID NO: 120)

wherein C$_3$=Cys[(mPEG)$_2$40 kDa], each corresponding to an amidated cysteine residue PEGylated via the side-chain thiol with a branched mPEG [(mPEG)$_2$] of the indicated MW; α is α-amino isobutyric acid (aib); and m=methionine sulfoxide (Met(O)).

In another embodiment of the present invention, there is provided a polypeptide comprising:

H$_x$SQGTFTSDYSKYLDSRRAQDFVQWLMNTKRNRNNIA, (SEQ ID NO: 161)

wherein H$_x$ is selected from the group consisting of His, H$_1$=Imidazole-lactic acid (ImiH); desamino-His (ΔNH$_2$-H), acetyl His, pyroglutamyl His, N-methyl-His (Me-H), N,N-dimethyl-His (Me$_2$-H); Benzoyl His (Bz-H), Benzyl His (Bzl-H), and Phe.

In yet another embodiment of the present invention, there is provided a polypeptide comprising:

HX$_1$QGTFTSDYSKYLDSRRAQDFVQWLMNTKRNRNNIA (SEQ ID NO: 162)

wherein X$_1$ is selected from the group consisting of Ser, Gly, Ala, Arg; Asn, Asp, Glu, Gln, His, Ile, Lys, Met, Phe, Pro, Thr, Trp, Tyr, Val, D-Ala, D-Ser, and α-aminoisobutyric acid.

The present invention further provides for a polypeptide comprising:

HSX$_2$GTFTSDYSKYLDSRRAQDFVQWLMNTKRNRNNIA (SEQ ID NO: 163)

X$_2$ is selected from the group consisting of Gln, Asp, Gln, Pro, Len, and L-norleucine.

In another embodiment of the present invention, there is provided a polypeptide comprising:

HSQGTFTSDYX$_3$X$_4$YLDSX$_6$X$_6$AX$_7$X$_8$FVX$_7$WLMX$_{10}$X$_{11}$KRNRN NX$_{12}$X$_{13}$X$_{14}$ (SEQ ID NO: 164)

wherein X$_3$ is Ser, Ala, Cys(mPEG), or Cys(cholesteryl);
X$_4$ is Lys, Cys(mPEG), or Cys(cholesteryl);
X$_6$ is any one of Arg, Cys(mPEG), or Cys(cholesteryl);
X$_7$ is any one of Gln, Cys(mPEG), or Cys(cholesteryl);
X$_8$ is Asp, Cys(mPEG), or Cys(cholesteryl);
X$_{10}$ is Asn, Cys(mPEG), or Cys(cholesteryl);
X$_{11}$ is Thr, Cys(mPEG), or Cys(cholesteryl);
X$_{12}$ is Ile, Cys(mPEG), or Cys(cholesteryl);
X$_{13}$ is Ala, Cys(mPEG), or Cys(cholesteryl); and
X$_{14}$ is amide, carboxylate, secondary amide, Ala, K(palmitoyl), Cys(mPEG), Cys(cholesteryl), or any linker to which mPEG or cholesterol is linked with a chemical bond.

wherein one or two of X$_3$ X$_4$, X$_6$-X$_8$, and X$_{10}$-X$_{14}$ is Cys (mPEG) or Cys(cholesteryl).

In an embodiment of the present invention, there is provided a polypeptide comprising:

HαX$_{15}$GTFTSDYSKYLDSZZAX$_{16}$DFVQWLX$_{17}$NTX$_{18}$ (SEQ ID NO: 165)

wherein X$_{15}$ is D or Q;
Z is any amino acid;
X$_{16}$ is C$_8$, Cys(N-ethylmaleimidyl), Q or C;
X$_{17}$ is m or M;
X$_{18}$ is an amidated k or K.

In another embodiment of the present invention, there is provided a polypeptide comprising:

HαDGTFTSDYSKYDSZZAQDFVQWLmNTKRNRNNIAX$_{19}$, (SEQ ID NO: 166)

wherein X$_{19}$ is C or C$_8$, Cys(N-ethylmaleimidyl).

In yet another embodiment of the present invention, there is provided a polypeptide of the formula:

HαDGTFTSDYSKYLDS-TtdsEC-CONH$_2$

In an embodiment of the present invention, there is provided a polypeptide of the formula:

HαDGTFTSDYSKYLDSRRAQDFVQWLmNTKRNRNNIA-Ttds-EEEEEC-COOH, (SEQ ID NO: 155)

wherein Ttds is 1-amino-4,7,10-trioxa-13-tridecanamine succinimic acid.

In another embodiment of the present invention there is provided a method for the treatment of a metabolic disease in a subject comprising administering to the subject a polypeptide as described above. The metabolic disease may be selected from the group consisting of diabetes, metabolic syndrome, hyperglycemia, and obesity and may be administered via a route peripheral to the brain, such as an oral, mucosal, buccal, sublingual, nasal rectal, subcutaneous, transdermal intravenous, intramuscular or intraperitoneal route.

In yet another embodiment of the present invention, there is provided a pharmaceutical composition comprising a polypeptide as described above and a pharmaceutically suitable carrier.

The present invention further relates to the use of the polypeptides of the present invention in the preparation of a medicament useful for the treatment or prevention of metabolic disorders such as diabetes or obesity in a subject in need thereof by administering the polypeptides and pharmaceutical compositions of the present invention.

BRIEF DESCRIPTION OF THE DRAWINGS

FIG. 14 summarizes the in vitro activity data at the GLP1 and GCG receptors in tabular form.

FIG. 16 illustrates in vitro potency data for the C-terminal truncated analogs acting at the GLP1 and GCG receptors (OxmOH (SEQ ID NO:167), OxmNH$_2$ (SEQ ID NO:4), Oxm25 (SEQ ID NO:27), Oxm26 (SEQ ID NO:28), Oxm27 (SEQ ID NO:29), Oxm90 (SEQ ID NO:94), Oxm91 (SEQ ID NO:95), Oxm92 (SEQ ID NO:96), Oxm93 (SEQ ID NO:97), GcgOH (SEQ ID NO:168)).

FIG. 17 presents in vitro potency data for select PEGylated OXM analogs acting at the GLP1 and GCG receptors.

DETAILED DESCRIPTION OF THE INVENTION

Figure 1A:
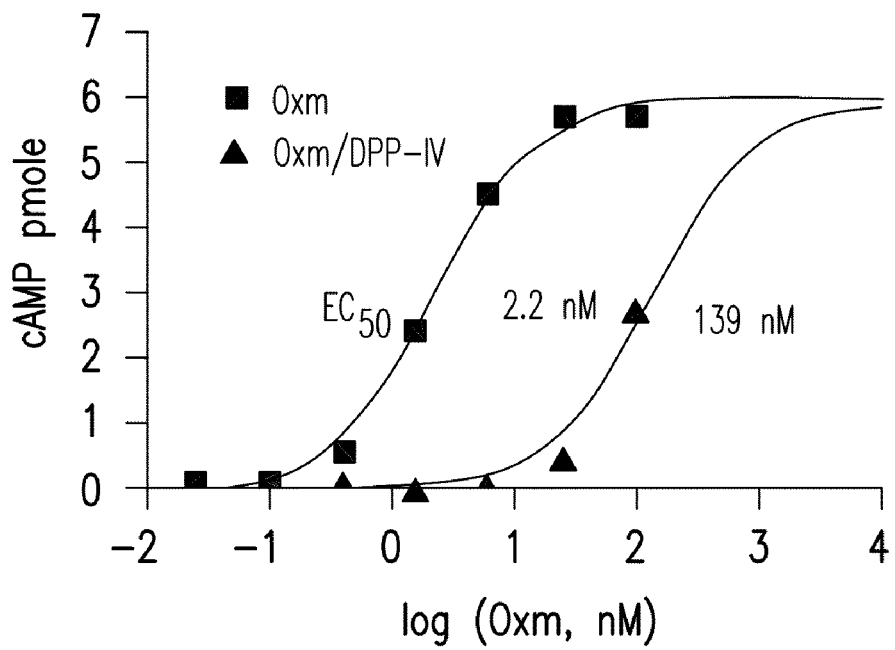
FIG. 1 depicts activation of a mutant form of the human GLP-1 receptor by (a) native porcine OXM and (b) PEGylated OXM2 and loss of potency due to preincubation of the peptides with DP-IV.
Figure 1B:
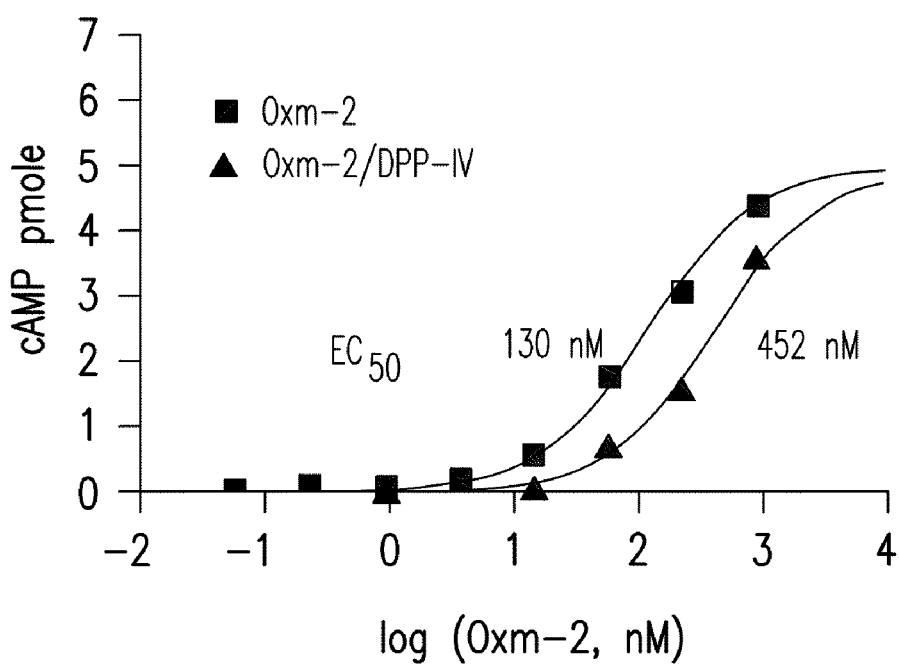

The invention relates to modified OXM derivatives. The OXM derivatives are developed by PEGylation or conjugation to other moieties or carrier proteins to improve stability and pharmacokinetics, and/or by incorporation of substitutions of amino acid residues to render the peptides resistant to DP-IV cleavage. In addition, the stabilized OXM derivatives do not exhibit glucagon receptor agonist activity, and may thereby offer certain advantages in the treatment of hyperglycemia and obesity in diabetic or prediabetic subjects. For those subjects, up-regulation of glucagon receptor signaling should be avoided, since it may result in elevated blood glucose levels.

Unless otherwise specified, the terms "polypeptide," "protein," and "peptide" is understood by the skilled artisan to also encompass various modified and/or stabilized forms. Such modified forms may be chemically modified forms, including, without limitation, PEGylated forms, palmitoylated forms, cholesterol-modified forms, etc. Modifications also include intra-molecular crosslinking and covalent attachment to various moieties such as lipids, flavin, biotin, polyethylene glycol derivatives, etc. In addition, modifications may also include cyclization, branching and cross-linking. Further, amino acids other than the conventional twenty amino acids encoded by genes may also be included in a polypeptide.

The Structures of the OXM Derivatives

The present invention provides modified OXM derivatives. In particular, the present invention relates to novel stabilized modified OXM polypeptide derivatives of the formula:

$$\text{(SEQ ID NO: 160)}$$
$$H_xX_1X_2GTFTSDYX_3X_4YLDX_5X_6X_6AX_7X_8FVX_7WLX_9X_{10}X_{11}KRNR$$
$$NNX_{12}X_{13}X_{14},$$

wherein $H_x$ is selected from the group consisting of His; imidazole-lactic acid (ImiH); desamino-His (ΔNH$_2$-H); acetyl His; pyroglutamyl His (PyrH); N-methyl-His (Me-H); N,N-dimethyl-His (Me$_2$-H); Benzoyl His (Bz-H); Benzyl His (Bzl-H); and Phe;

$X_1$ is selected from the group consisting of Ser; Gly; Ala; Arg; Asn; Asp; Glu; Gln; His; Ile; Lys; Met; Phe; Pro; Thr; Trp; Tyr; Val; D-Ala; D-Ser; and α-aminoisobutyric acid;

$X_2$ is Gln, Asp, Glu, Pro, Leu or L-norleucine;

$X_3$ is Ser, Ala, Cys, Cys(mPEG), or Cys(cholesteryl);

$X_4$ is Lys, Cys, Cys(mPEG), or Cys(cholesteryl);

$X_5$ is Set or Ala;

$X_6$ is any amino acid;

$X_7$ is Gln, Cys, Cys(mPEG), or Cys(cholesteryl);

$X_8$ is Asp, Cys, Cys(mPEG), or Cys(cholesteryl);

$X_9$ is Met, Met(O), Val, norleucine, alanine, α-aminoisobutyric acid or O-methyl-homoserine;

$X_{10}$ is Asn, Cys, Cys(mPEG), or Cys(cholesteryl);

$X_{11}$ is Thr, Cys, Cys(mPEG), or Cys(cholesteryl);

$X_{12}$ is Ile, Cys, Cys(mPEG), or Cys(cholesteryl);

$X_{13}$ is Ala, Cys, Cys(mPEG), or Cys(cholesteryl); and $X_{14}$ is amid; carboxylate, secondary amide, Ala, K(palmitoyl), Cys, Cys(mPEG), Cys(cholesteryl) or any linker to which mPEG or cholesterol is linked with a chemical bond.

Additionally, any one or two of $X_3X_4$, $X_6$-$X_8$, and $X_{10}$-$X_{14}$ may be Cys(mPEG) or Cys(cholesteryl); Cys(mPEG)teine may also be $C_1$; $C_2$; $C_3$ or $C_6$, wherein $C_1$=Cys(mPEG)5 kDa, $C_2$=Cys(mPEG)20 kDa, $C_3$=Cys(mPEG)$_2$40 kDa, $C_6$=Cys (mPEG)$_2$60 kDa and each corresponds to a cysteine residue PEGylated via the side chain thiol with linear methoxyPEG (mPEG) or branched mPEG$_2$ of the indicated MW.

The present invention further provides an OXM polypeptide of the formula:

$$\text{(SEQ ID NO: 120)}$$
$$H\alpha DGTFTSDYSKYLDSRRAQDFVQWLmNTKRNRNNIAC_3$$

wherein $C_3$=Cys[(mPEG)$_2$40 kDa], each corresponding to an amidated cysteine residue PEGylated via the side-chain thiol with a branched mPEG [(mPEG)$_2$] of the indicated MW; α is α-amino isobutyric acid (aib); and m=methionine sulfoxide [Met(O)].

In an embodiment of the present invention, there is provided a polypeptide comprising:

$$\text{(SEQ ID NO: 162)}$$
$$HX_1QGTFTSDYSKYLDSRRAQDFVQWLMNTKRNRNNIA$$

wherein $X_1$ is selected from the group consisting of Ser, Gly, Ala, Arg; Asn, Asp, Gln, Gln, His, Ile, Lys, Met, Phe, Pro, Thr, Trp, Tyr, Val, D-Ala, D-Ser, and α-aminoisobutyric acid.

The present invention further provides for a polypeptide comprising:

$$\text{(SEQ ID NO: 163)}$$
$$HSX_2GTFTSDYSKYLDSRRAQDFVQWLMNTKRNRNNIA$$

$X_2$ is selected from the group consisting of Gln, Asp, Glu, Pro, Leu, and L-norleucine.

In another embodiment of the present invention, there is provided a polypeptide comprising:

(SEQ ID NO: 164)
HSQGTFTSDYX$_3$X$_4$YLDSX$_6$X$_6$AX$_7$X$_8$FVX$_7$WLMX$_{10}$X$_{11}$KRNRNNX$_{12}$X$_{13}$X$_{14}$ wherein X$_3$ is Ser, Ala, Cys(mPEG), or Cys(cholesteryl);
X$_4$ is Lys, Cys(mPEG), or Cys(cholesteryl);
X$_6$ is Arg, Cys(mPEG), or Cys(cholesteryl);
X$_7$ is Gln, Cys(mPEG), or Cys(cholesteryl);
X$_8$ is Asp, Cys(mPEG), or Cys(cholesteryl);
X$_{10}$ is Asn, Cys(mPEG), or Cys(cholesteryl);
X$_{11}$ is Thr, Cys(mPEG), or Cys(cholesteryl);
X$_{12}$ is Ile, Cys(mPEG), or Cys(cholesteryl);
X$_{13}$ is Ala, Cys(mPEG), or Cys(cholesteryl); and X$_{14}$ is amide, carboxylate, secondary amide, Ala, K(palmitoyl), Cys (mPEG), Cys(cholesteryl), or any linker to which mPEG or cholesterol is linked with a chemical bond.

wherein one or two of X$_3$ X$_4$, X$_6$-X$_8$, and X$_{10}$-X$_{14}$ is Cys (mPEG) or Cys(cholesteryl).

In an embodiment of the present invention, there is provided a polypeptide comprising:

(SEQ ID NO: 165)
HαX$_{15}$GTFTSDYSKYLDSZZAX$_{16}$DFVQWLX$_{17}$NTX$_{18}$ wherein X$_{15}$ is D or Q;
Z is any amino acid;
X$_{16}$ is C8, Q or C;
X$_{17}$ is m or M;
X$_{18}$ is amidated k or K.

In another embodiment of the present invention, there is provided a polypeptide comprising:

(SEQ ID NO: 166)
HαDGTFTSDYSKYDSZZAQDFVQWLmNTKRNRNNIAX$_{19}$, wherein X$_{19}$ is C or C$_8$.

In yet another embodiment of the present invention, there is provided a polypeptide of the formula:

(SEQ ID NO: 152)
HαDGTFTSDYSKYLDS-TtdsEC-CONH$_2$.

In an embodiment of the present invention, there is provided a polypeptide of the formula:

(SEQ ID NO: 155)
HαDGTFTSDYSKYLDSRRAQDFVQWLmNTKRNRNNIA-Ttds-EEEE EC-COOH.

As used herein, the abbreviations of amino acid residues are shown as follows:

| Amino Acids | Three-Letter Abbreviations | One-Letter Abbreviations |
|---|---|---|
| Alanine | Ala | A |
| Arginine | Arg | R |
| Asparagine | Asn | N |
| Aspartate | Asp | D |
| Cysteine | Cys | C |
| Histidine | His | H |
| Isoleucine | Ile | I |
| Glutamine | Gln | Q |
| Glutamate | Glu | E |
| Glycine | Gly | G |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Unless specifically designated otherwise, all the amino acid residues are in the L-form.

In comparison to the wild-type OXM, the OXM derivatives of the present invention contain several amino acid substitutions, and/or can be PEGylated or otherwise modified (e.g. with cholesterol moieties). Analogs may be double conjugated, e.g., with to both cholesterol and PEG. Such OXM derivatives are resistant to cleavage and inactivation by dipeptidyl peptidase IV (DP-IV).

By "receptor agonist" is meant any endogenous or exogenous (drug) substance or compound that can interact with a receptor, for example, the GLP-1R or the glucagon receptor, and thereby initiate a pharmacological or biochemical response characteristic of receptor activation. Typically, the OXM derivatives of the instant invention are characterized by their affinity to the human GLP-1R and display an EC50 for this receptor in the range of 0.1 pM to 1 µM. The OXM derivatives of the instant invention also are characterized by their affinity to the GcgR, displaying an EC50>1 µM.

The OXM derivatives of the present invention may be useful in the reduction of food intake and body weight and may mediate glucose-stimulated insulin secretion (GSIS) from pancreatic islets, thereby providing a treatment option for individuals afflicted with a metabolic disorder such as obesity, diabetes, metabolic syndrome X, hyperglycemia, impaired fasting glucose, and other prediabetic states.

TABLE 1

OXM Derivatives

| SEQ ID NO | Peptides | Sequences |
|---|---|---|
| 1 | OXM1 | HGQGTFTSDYSKYLDSRRAQDFVQWLMNTKRNRNNIAA-COOH |
| 2 | OXM2 | HGQGTFTSDYSKYLDSRRAQDFVQWLMNTKRNRNNIAC$_2$-COOH |
| 3 | OXM3 | HGQGTFTSDYSKYLDSRRAQDFVQWLMNTKRNRNNIAC$_3$-COOH |
| 4 | OXM-NH$_2$ | HSQGTFTSDYSKYLDSRRAQDFVQWLMNTKRNRNNIA-CONH$_2$ |
| 5 | Ac-OXM-NH$_2$ | Ac-HSQGTFTSDYSKYLDSRRAQDFVQWLMNTKRNRNNIA-CONH$_2$ |

TABLE 1-continued

OXM Derivatives

| SEQ ID NO | Peptides | Sequences |
|---|---|---|
| 6 | Ac-OXM | Ac-HSQGTFTSDYSKYLDSRRAQDFVQWLMNTKRNRNNIA-COOH |
| 7 | OXM4 | HαQGTFTSDYSKYLDSRRAQDFVQWLMNTKRNRNNIA-COOH |
| 8 | OXM5 | HVQGTFTSDYSKYLDSRRAQDFVQWLMNTKRNRNNIA-COOH |
| 9 | OXM6 | HaQGTFTSDYSKYLDSRRAQDFVQWLMNTKRNRNNIA-COOH |
| 10 | OXM7 | HsQGTFTSDYSKYLDSRRAQDFVQWLMNTKRNRNNIA-COOH |
| 11 | OXM8 | HSEGTFTSDYSKYLDSRRAQDFVQWLMNTKRNRNNIA-COOH |
| 12 | OXM9 | HSDGTFTSDYSKYLDSRRAQDFVQWLMNTKRNRNNIA-COOH |
| 13 | OXM10 | HSLGTFTSDYSKYLDSRRAQDFVQWLMNTKRNRNNIA-COOH |
| 14 | OXM11 | HSnGTFTSDYSKYLDSRRAQDFVQWLMNTKRNRNNIA-COOH |
| 15 | OXM12 | HGEGTFTSDYSKYLDSRRAQDFVQWLMNTKRNRNNIA-COOH |
| 16 | OXM13 | FSQGTFTSDYSKYLDSRRAQDFVQWLMNTKRNRNNIA-COOH |
| 17 | OXM14 | Pyr-HSQGTFTSDYSKYLDSRRAQDFVQWLMNTKRNRNNIA-CONH$_2$ |
| 18 | OXM15 | HSPGTFTSDYSKYLDSRRAQDFVQWLMNTKRNRNNIA-COOH |
| 19 | OXM16 | H$_1$SQGTFTSDYSKYLDSRRAQDFVQWLMNTKRNRNNIA-CONH$_2$ |
| 20 | OXM17 | Me-HSQGTFTSDYSKYLDSRRAQDFVQWLMNTKRNRNNIA-CONH$_2$ |
| 21 | OXM18 | H$_2$SQGTFTSDYSKYLDSRRAQDFVQWLMNTKRNRNNIA-CONH$_2$ |
| 22 | OXM19 | Me$_2$-HSQGTFTSDYSKYLDSRRAQDFVQWLMNTKRNRNNIA-CONH$_2$ |
| 23 | OXM20 | Bz-HSQGTFTSDYSKYLDSRRAQDFVQWLMNTKRNRNNIA-CONH$_2$ |
| 24 | OXM21 | Bzl-HSQGTFTSDYSKYLDSRRAQDFVQWLMNTKRNRNNIA-CONH$_2$ |
| 25 | OXM23 | HAEGTFTSDVSSYLEGQAAKEFIAWLMNTKRNRNNIA-CONH$_2$ |
| 26 | OXM24 | HSQGTFTSDYAKYLDARRAQDFVQWLMNTKRNRNNIA-CONH$_2$ |
| 27 | OXM25 | HSQGTFTSDYSKYLDSRRAQDFVQWLMNTKRNRNNI-CONH$_2$ |
| 28 | OXM26 | HSQGTFTSDYSKYLDSRRAQDFVQWLMNTKRNRNN-CONH$_2$ |
| 29 | OXM27 | HSQGTFTSDYSKYLDSRRAQDFVQWLMNTKRNRN-CONH$_2$ |
| 30 | OXM28 | HαQGTFTSDYSKYLDSRRAQDFVQWLMNTKRNRNNIA-CONH$_2$ |
| 31 | OXM29 | HαQGTFTSDYSKYLDSRRAQDFVQWLMNTKRNRNNIAC-CONH$_2$ |
| 32 | OXM30 | HαQGTFTSDYSKYLDSRRAQDFVQWLMCTKRNRNNIA-CONH$_2$ |
| 33 | OXM31 | HsQGTFTSDYSKYLDSRRAQDFVQWLmNTKRNRNNIA-COOH |
| 34 | OXM32 | HsQGTFTSDYSKYLDSRRAQDFVQWLMNTKRNRNNIA-CONH$_2$ |
| 35 | OXM33-36 precursor | HsQGTFTSDYSKYLDSRRAQDFVQWLMNTKRNRNNIAC-CONH$_2$ |
| 36 | OXM33 | HsQGTFTSDYSKYLDSRRAQDFVQWLMNTKRNRNNIAC$_1$-CONH$_2$ |
| 37 | OXM34 | HsQGTFTSDYSKYLDSRRAQDFVQWLMNTKRNRNNIAC$_2$-CONH$_2$ |
| 38 | OXM35 | HsQGTFTSDYSKYLDSRRAQDFVQWLMNTKRNRNNIAC$_3$-CONH$_2$ |
| 39 | OXM36 | HsQGTFTSDYSKYLDSRRAQDFVQWLMNTKRNRNNIAC$_4$-CONH$_2$ |
| 40 | OXM37 | HAQGTFTSDYSKYLDSRRAQDFVQWLMNTKRNRNNIA-CONH$_2$ |
| 41 | OXM38 | HRQGTFTSDYSKYLDSRRAQDFVQWLMNTKRNRNNIA-CONH$_2$ |
| 42 | OXM39 | HNQGTFTSDYSKYLDSRRAQDFVQWLMNTKRNRNNIA-CONH$_2$ |

TABLE 1-continued

OXM Derivatives

| SEQ ID NO | Peptides | Sequences |
|---|---|---|
| 43 | OXM40 | HDQGTFTSDYSKYLDSRRAQDFVQWLMNTKRNRNNIA-CONH$_2$ |
| 44 | OXM41 | HEQGTFTSDYSKYLDSRRAQDFVQWLMNTKRNRNNIA-CONH$_2$ |
| 45 | OXM42 | HQQGTFTSDYSKYLDSRRAQDFVQWLMNTKRNRNNIA-CONH$_2$ |
| 46 | OXM43 | HHQGTFTSDYSKYLDSRRAQDFVQWLMNTKRNRNNIA-CONH$_2$ |
| 47 | OXM44 | HIQGTFTSDYSKYLDSRRAQDFVQWLMNTKRNRNNIA-CONH$_2$ |
| 48 | OXM45 | HLQGTFTSDYSKYLDSRRAQDFVQWLMNTKRNRNNIA-CONH$_2$ |
| 49 | OXM46 | HKQGTFTSDYSKYLDSRRAQDFVQWLMNTKRNRNNIA-CONH$_2$ |
| 50 | OXM47 | HMQGTFTSDYSKYLDSRRAQDFVQWLMNTKRNRNNIA-CONH$_2$ |
| 51 | OXM48 | HFQGTFTSDYSKYLDSRRAQDFVQWLMNTKRNRNNIA-CONH$_2$ |
| 52 | OXM49 | HPQGTFTSDYSKYLDSRRAQDFVQWLMNTKRNRNNIA-CONH$_2$ |
| 53 | OXM50 | HTQGTFTSDYSKYLDSRRAQDFVQWLMNTKRNRNNIA-CONH$_2$ |
| 54 | OXM51 | HWQGTFTSDYSKYLDSRRAQDFVQWLMNTKRNRNNIA-CONH$_2$ |
| 55 | OXM52 | HYQGTFTSDYSKYLDSRRAQDFVQWLMNTKRNRNNIA-CONH$_2$ |
| 56 | OXM53 | HsEGTFTSDYSKYLDSRRAQDFVQWLMNTKRNRNNIA-CONH$_2$ |
| 57 | OXM54 | HsQGTFTSDYSKYLDSRRAQDFVQWLMNTKRNRNNIAC$_5$-CONH$_2$ |
| 58 | OXM55-59 precursor | HsQGTFTSDYSKYLDSRRACDFVQWLMNTKRNRNNIA-CONH$_2$ |
| 59 | OXM55 | HsQGTFTSDYSKYLDSRRAC$_5$DFVQWLMNTKRNRNNIA-CONH$_2$ |
| 60 | OXM56 | HsQGTFTSDYSKYLDSRRAC$_1$DFVQWLMNTKRNRNNIA-CONH$_2$ |
| 61 | OXM57 | HsQGTFTSDYSKYLDSRRAC$_2$DFVQWLMNTKRNRNNIA-CONH$_2$ |
| 62 | OXM58 | HsQGTFTSDYSKYLDSRRAC$_3$DFVQWLMNTKRNRNNIA-CONH$_2$ |
| 63 | OXM59 | HsQGTFTSDYSKYLDSRRAC$_4$DFVQWLMNTKRNRNNIA-CONH$_2$ |
| 64 | OXM60 | HsQGTFTSDYSKYLDSRRAQDFVQWLnNTKRNRNNIA-CONH$_2$ |
| 65 | OXM61 | HsQGTFTSDYSKYLDSRRAQDFVQWLMC$_5$TKRNRNNIA-CONH$_2$ |
| 66 | OXM62 | HsQGTFTSDYSKYLDSRRAQDFVQWLMC$_1$TKRNRNNIA-CONH$_2$ |
| 67 | OXM63 | HsQGTFTSDYSKYLDSRRAQDFVQWLMC$_2$TKRNRNNIA-CONH$_2$ |
| 68 | OXM64 | HsQGTFTSDYSKYLDSRRAQDFVQWLMC$_3$TKRNRNNIA-CONH$_2$ |
| 69 | OXM65 | HsQGTFTSDYSKYLDSRRAQDFVQWLMC$_4$TKRNRNNIA-CONH$_2$ |
| 70 | OXM66 | HαQGTFTSDYSKYLDSRRAQDFVQWLMNTKRNRNNIAC$_5$-CONH$_2$ |
| 71 | OXM67 | HαQGTFTSDYSKYLDSRRAQDFVQWLMNTKRNRNNIAC$_1$-CONH$_2$ |
| 72 | OXM68 | HαQGTFTSDYSKYLDSRRAQDFVQWLMNTKRNRNNIAC$_2$-CONH$_2$ |
| 73 | OXM69 | HαQGTFTSDYSKYLDSRRAQDFVQWLMNTKRNRNNIAC$_3$-CONH$_2$ |
| 74 | OXM70 | HαQGTFTSDYSKYLDSRRAQDFVQWLMNTKRNRNNIAC$_4$-CONH$_2$ |
| 75 | OXM71 | HsEGTFTSDYSKYLDSRRAQDFVQWLMNTKRNRNNIAC-CONH$_2$ |
| 76 | OXM72 | HsEGTFTSDYSKYLDSRRAQDFVQWLMNTKRNRNNIAC$_5$-CONH$_2$ |
| 77 | OXM73 | HsEGTFTSDYSKYLDSRRAQDFVQWLMNTKRNRNNIAC$_1$-CONH$_2$ |
| 78 | OXM74 | HsEGTFTSDYSKYLDSRRAQDFVQWLMNTKRNRNNIAC$_2$-CONH$_2$ |
| 79 | OXM75 | HsEGTFTSDYSKYLDSRRAQDFVQWLMNTKRNRNNIAC$_3$-CONH$_2$ |
| 80 | OXM76 | HsEGTFTSDYSKYLDSRRAQDFVQWLMNTKRNRNNIAC$_4$-CONH$_2$ |

TABLE 1-continued

OXM Derivatives

| SEQ ID NO | Peptides | Sequences |
| --- | --- | --- |
| 81 | OXM77 | HsQGTFTSDYSKYLDSRRAQCFVQWLMNTKRNRNNIA-CONH$_2$ |
| 82 | OXM78 | HsQGTFTSDYSKYLDSRRAQC$_5$FVQWLMNTKRNRNNIA-CONH$_2$ |
| 83 | OXM79 | HsQGTFTSDYSKYLDSRRAQC$_1$FVQWLMNTKRNRNNIA-CONH$_2$ |
| 84 | OXM80 | HsQGTFTSDYSKYLDSRRAQC$_2$FVQWLMNTKRNRNNIA-CONH$_2$ |
| 85 | OXM81 | HsQGTFTSDYSKYLDSRRAQC$_3$FVQWLMNTKRNRNNIA-CONH$_2$ |
| 86 | OXM82 | HsQGTFTSDYSKYLDSRRAQC$_4$FVQWLMNTKRNRNNIA-CONH$_2$ |
| 87 | OXM83 | HsQGTFTSDYSKYLDSRRAQDFVCWLMNTKRNRNNIA-CONH$_2$ |
| 88 | OXM84 | HsQGTFTSDYSKYLDSRRAQDFVC$_5$WLMNTKRNRNNIA-CONH$_2$ |
| 89 | OXM85 | HsQGTFTSDYSKYLDSRRAQDFVC$_1$WLMNTKRNRNNIA-CONH$_2$ |
| 90 | OXM86 | HsQGTFTSDYSKYLDSRRAQDFVC$_2$WLMNTKRNRNNIA-CONH$_2$ |
| 91 | OXM87 | HsQGTFTSDYSKYLDSRRAQDFVC$_3$WLMNTKRNRNNIA-CONH$_2$ |
| 92 | OXM88 | HsQGTFTSDYSKYLDSRRAQDFVC$_4$WLMNTKRNRNNIA-CONH$_2$ |
| 93 | OXM89 | HsQGTFTSDYSKYLDSRRAQDFVQWLVNTKRNRNNIA-CONH$_2$ |
| 94 | OXM90 | HSQGTFTSDYSKYLDSRRAQDFVQWLMNTKRNR-CONH$_2$ |
| 95 | OXM91 | HSQGTFTSDYSKYLDSRRAQDFVQWLMNTKRN-CONH$_2$ |
| 96 | OXM92 | HSQGTFTSDYSKYLDSRRAQDFVQWLMNTKR-CONH$_2$ |
| 97 | OXM93 | HSQGTFTSDYSKYLDSRRAQDFVQWLMNTK-CONH$_2$ |
| 98 | OXN94 | HαQGTFTSDYSKYLDSRRAQDFVQWLmNTKRNRNNIAC-CONH$_2$ |
| 99 | OXM95 | HsDGTFTSDYSKYLDSRRAQDFVQWLMNTKRNRNNIAC$_5$-CONH$_2$ |
| 100 | OXM96 | HαEGTFTSDYSKYLDSRRAQDFVQWLMNTKRNRNNIAC$_5$-CONH$_2$ |
| 101 | OXM97 | HαDGTFTSDYSKYLDSRRAQDFVQWLMNTKRNRNNIAC$_5$-CONH$_2$ |
| 102 | OXM98 | HαQGTFTSDYSKYLDSRRAQDFVQWLmNTKRNRNNIAC$_5$-CONH$_2$ |
| 103 | OXM99 | HαQGTFTSDYSKYLDSRRAQDFVQWLmNTKRNRNNIAC$_3$-CONH$_2$ |
| 104 | OXM100 | HαQGTFTSDYSKYLDSRRAQDFVQWLmNTKRNRNNIAC$_6$-CONH$_2$ |
| 105 | OXM101 | HαQGTFTSDYSKYLDSRRAQDFVQWLmNTKRNRNNIAC$_4$-CONH$_2$ |
| 106 | OXM102 | HαQGTFTSDYSKYLDSRRAC$_5$DFVQWLMNTKRNRNNIA-CONH$_2$ |
| 107 | OXM103 | HαQGTFTSDYSKYLDSRRAC$_3$DFVQWLMNTKRNRNNIA-CONH$_2$ |
| 108 | OXM104 | HαQGTFTSDYSKYLDSRRAQC$_5$FVQWLMNTKRNRNNIA-CONH$_2$ |
| 109 | OXM105 | HαQGTFTSDYSKYLDSRRAQC$_3$FVQWLMNTKRNRNNIA-CONH$_2$ |
| 110 | OXM106 | HαQGTFTSDYSKYLDSRRAQDFVC$_5$WLmNTKRNRNNIA-CONH$_2$ |
| 111 | OXM107 | HαQGTFTSDYSKYLDSRRAQDFVC$_3$WLmNTKRNRNNIA-CONH$_2$ |
| 112 | OXM108 | HαQGTFTSDYSKYLDSRRAQDFVQWLMC$_5$TKRNRNNIA-CONH$_2$ |
| 113 | OXM109 | HαQGTFTSDYSKYLDSRRAQDFVQWLMC$_3$TKRNRNNIA-CONH$_2$ |
| 114 | OXM110 | HsQGTFTSDYSKYLDSRRAQDFVQWLMNTKRNRNNIAK(palmitoyl)-CONH$_2$ |
| 115 | OXM111 | H$_2$αQGTFTSDYSKYLDSRRAQDFVQWLmNTKRNRNNIAC-CONH$_2$ |
| 116 | OXM112 | H$_2$αQGTFTSDYSKYLDSRRAQDFVQWLmNTKRNRNNIAC$_5$-CONH$_2$ |
| 117 | OXM113 | H$_2$αQGTFTSDYSKYLDSRRAQDFVQWLmNTKRNRNNIAC$_3$-CONH$_2$ |

TABLE 1-continued

OXM Derivatives

| SEQ ID NO | Peptides | Sequences |
|---|---|---|
| 118 | OXM114 | H₂αQGTFTSDYSKYLDSRRAQDFVQWLmNTKRNRNNIAC₄-CONH₂ |
| 119 | OXM116 | HαDGTFTSDYSKYLDSRRAQDFVQWLmNTKRNRNNIAC-CONH₂ |
| 120 | OXM117/145/146 | HαDGTFTSDYSKYLDSRRAQDFVQWLmNTKRNRNNIAC₃-CONH₂ |
| 121 | OXM118 | HαDGTFTSDYSKYLDSRRAQDFVQWLmNTKRNRNNIAC₄-CONH₂ |
| 122 | OXM119 | HαQGTFTSDYCKYLDSRRAQDFVQWLmNTKRNRNNIA-CONH₂ |
| 123 | OXM120 | HαQGTFTSDYC₅KYLDSRRAQDFVQWLmNTKRNRNNIA-CONH₂ |
| 124 | OXM121 | HαQGTFTSDYC₃KYLDSRRAQDFVQWLmNTKRNRNNIA-CONH₂ |
| 125 | OXM122 | HαQGTFTSDYSCYLDSRRAQDFVQWLmNTKRNRNNIA-CONH₂ |
| 126 | OXM123 | HαQGTFTSDYSC₅YLDSRRAQDFVQWLmNTKRNRNNIA-CONH₂ |
| 127 | OXM124 | HαQGTFTSDYSC₃YLDSRRAQDFVQWLmNTKRNRNNIA-CONH₂ |
| 128 | OXM125 | HαDGTFTSDYSKYLDSRRAC₃DFVQWLmNTKRNRNNIA-CONH₂ |
| 129 | OXM126 | HαQGTFTSDYSKYLDSRRAQDCVQWLmNTKRNRNNIA-CONH₂ |
| 130 | OXM127 | HαQGTFTSDYSKYLDSRRAQDC₄VQWLmNTKRNRNNIA-CONH₂ |
| 131 | OXM128 | H₂αDGTFTSDYSKYLDSRRACDFVQWLmNTKRNRNNIA-CONH₂ |
| 132 | OXM129 | H₂αDGTFTSDYSKYLDSRRAC₃DFVQWLmNTKRNRNNIA-CONH₂ |
| 133 | OXM130 | HαDGTFTSDYSKYLDSRRAQDFVQWLMNTK-CONH₂ |
| 134 | OXM131 | HαDGTFTSDYSKYLDSRRAQDFVQWLMNTK-CONH₂ |
| 135 | OXM132 | HαQGTFTSDYSKYLDSRRACDFVQWLmNTKRNRNNIA-CONH₂ |
| 136 | OXM133 | HαQGTFTSDYSKYLDSRRAC₅DFVQWLmNTKRNRNNIA-CONH₂ |
| 137 | OXM134 | HαQGTFTSDYSKYLDSRRAC₃DFVQWLmNTKRNRNNIA-CONH₂ |
| 138 | OXM135 | HαQGTFTSDYSKYLDSRRACDFVQWLmNTK-CONH₂ |
| 139 | OXM136 | HαQGTFTSDYSKYLDSRRAC₃DFVQWLmNTK-CONH₂ |
| 140 | OXM137 | HαDGTFTSDYSKYLDSRRACDFVQWLmNTK-CONH₂ |
| 141 | OXM138 | HαDGTFTSDYSKYLDSRRAC₃DFVQWLmNTK-CONH₂ |
| 142 | OXM139 | HαDGTFTSDYSKYLDSRRAQDFVQWLmNTKRNRNNIAC₈-CONH₂ |
| 143 | OXM141 | HαDGTFTSDYSKYLDSRRAC₃DFVQWLmNTKRNRNNIAC₄-CONH₂ |
| 144 | OXM142 | HαQGTFTSDYSKYLDSRRAC₃DFVQWLmNTKRNRNNIAC₄-CONH₂ |
| 145 | OXM143 | HαQGTFTSDYSKYLDSRRAC₈DFVQWLmNTK-CONH₂ |
| 146 | OXM144 | HαDGTFTSDYSKYLDSRRAC₈DFVQWLmNTK-CONH₂ |
| 147 | OXM147 | HαQGTFTSDYSKYLDSRRACDFVQWLMNTK-CONH₂ |
| 148 | OXM148 | HαQGTFTSDYSKYLDSRRAC₈DFVQWLMNTK-CONH₂ |
| 149 | OXM149 | HαDGTFTSDYSKYLDSRRACDFVQWLmNTk-CONH₂ |
| 150 | OXM150 | HαDGTFTSDYSKYLDSRRAC₈DFVQWLmNTk-CONH₂ |
| 151 | OXM151 | HαDGTFTSDYSKYLDSEAAQDFVQWLmNTKRNRNNIAC-CONH₂ |
| 152 | OXM152 | HαDGTFTSDYSKYLDS-TtdsEC-CONH₂ |
| 153 | OXM153 | HαDGTFTSDYSKYLDSEAAQDFVQWLmNTKRNRNNIAC₈-CONH₂ |
| 154 | OXM154 | HαDGTFTSDYSKYLDSEAAQDFVQWLmNTKRNRNNIAC₃-CONH₂ |
| 155 | OXM155 | HαDGTFTSDYSKYLDSRRAQDFVQWLmNTKRNRNNIA-Ttds-EEEEEC-COOH |

TABLE 1-continued

OXM Derivatives

| SEQ ID NO | Peptides | Sequences |
|---|---|---|
| 156 | OXM174 | HαQGTFTSDYSKYLDSRRAC$_3$DFVQWLANTKRNRNNIA-CONH$_2$ |
| 157 | OXM175 | HαQGTFTSDYSKYLDSRRAC$_3$DFVQWLVNTKRNRNNIA-CONH$_2$ |
| 158 | OXM176 | HαQGTFTSDYSKYLDSRRAC$_3$DFVQWLαNTKRNRNNIA-CONH$_2$ |
| 159 | OXM199 | HαQGTFTSDYSKYLDSRRAC$_3$DFVQWLXNTKRNRNNIA-CONH$_2$ |

α = α-aminoisobutyric acid (Aib);
a = D-Ala;
s = D-Ser;
n = L-norleucine (Nle),
X = O-methyl-homoserine;
C$_1$ = Cys (mPEG) 5 kDa,
C$_2$ = Cys (mPEG) 20 kDa,
C$_3$ = Cys (mPEG)$_2$ 40 kDa, each corresponding to a cysteine residue PEGylated via the side-chain thiol with linear methoxyPEG (mPEG) or branched mPEG [(mPEG)$_2$] of the indicated MW;
C$_4$ = Cys (Cholesteryl), corresponding to a cysteine residue linked to cholesterol via the side-chain thiol;
C$_5$ = Cys(CH$_2$CONH$_2$), corresponding to a cysteine residue in which the side-chain thiol was reacted with iodoacetamide;
C$_6$ = Cys (mPEG)$_2$60 kDa, each corresponding to a cysteine residue PEGylated via the side-chain thiol with linear methoxyPEG (mPEG) or branched mPEG$_2$mPEG [(mPEG)$_2$] of the indicated MW;
H$_1$ = Imidazole-lactic acid (ImiH);
H$_2$ = desamino-His (ΔNH$_2$–H)$^1$
Ac = Acetyl;
Pyr = pyroglutamyl;
Me-H = N-methyl-His;
Me$_2$-H = N,N-dimethyl-His;
Bz = Benzoyl (C7H5O);
Bzl = Benzyl(C7H7);
m = methionine sulfoxide.
C$_7$ = (Cys)$_2$ (mPEG)2-40 kDa, each corresponding to two cysteine residues PEGylated via the side chain thiol to the same one linear methoxyPEG (mPEG) or one branched mPEG [(mPEG)$_2$],
C$_8$ = Cys (N-ethylmaleimidyl); Ttds, 1-amino-4,7,10-trioxa-13-tridecanamine succinimic acid;
k, D-Lysine.

1.1. Amino Acid Substitutions and Modifications

Substitution at X$_1$ (position 2 of OXM) is designed to improve the resistance of the OXM derivatives to proteolysis by DP-IV, which plays a key role in the degradation of many peptides, including OXM and GLP-1. It has been reported that substitution of Ser at position 2 with Gly in GLP-1 improves resistance to DP-IV cleavage (Lotte, B. K., *J. Med. Chem.*, 47:4128-4134 (2004)). In spite of the high degree of sequence homology between OXM and GLP-1, the Ser→Gly substitution at position 2 was not found to confer a similar effect on the modified OXM. However, the substitution of Ser at position 2 with Val, Ile, Asp, Glu, Met, Trp, Asn, D-Ala, D-Ser, or α-aminoisobutyric acid rendered the corresponding OXM derivative more resistant to DP-IV than the wild-type OXM, as discussed infra in the Examples. Peptides with a substitution at X$_1$ (position 2 of OXM) include: OXM4-7, 12, 23, 28-59, and the precursors of OXM33-36 and OXM55-59.

The substitutions at X$_2$ (position 3 of OXM) are designed to create OXM derivatives that are selective agonists of GLP-1R with minimal or no activation of GcgR. Such OXM derivatives may be advantageous when treating obese diabetics. Peptides with a substitution at X$_2$ (position 3 of OXM) include: OXM8-12, 15, 23, 53, 95, 96 and 97.

Similarly, the substitutions to Ala at X$_3$ and X$_5$ (positions 11 and 16) are designed to create OXM derivatives that are selective for GLP-1R and have no activity against GcgR. One such example of the substitutions to Ala at X$_3$ and X$_5$ (positions 11 and 16) is OXM24.

The substitutions to cysteine at any one or more of positions X$_3$ X$_4$, X$_6$-X$_8$, and X$_{10}$-X$_{14}$ allow for the PEGylation or cholesterylation of the OXM derivative at specific sites. Other substitutions or modifications are known in the art and include those which physically adhere to the surface of the active agent but do not chemically bond to or interact with the active agent. Two or more such modifications can be employed and may be selected from known organic and inorganic pharmaceutical excipients, including various polymers, low molecular weight oligomers, natural products, and surfactants.

1.2. PEGylation and/or Cholesterylation

The invention contemplates the use of multi-functional polymer derivatives, as exemplified by bifunctional and multi-arm N-maleimidyl PEG derivatives. A wide variety of polyethylene glycol (PEG) species may be used for PEGylation of the novel OXM derivatives of the present invention. Substantially any suitable reactive PEG reagent can be used and suitable species include, but are not limited to, those which are available for sale in the Drug Delivery Systems catalog of NOF Corporation (Yebisu Garden Place Tower, 20-3 Ebisu 4-chome, Shibuya-ku, Tokyo 150-6019) and, for exemplary purposes, of the Molecular Engineering catalog of Nelctar Therapeutics (490 Discovery Drive, Huntsville, Ala. 35806). By way of example and not limitation, the following PEG reagents are often preferred in various embodiments: multi-Arm PEG, mPEG(MAL)$_2$, mPEG2(MAL), any of the SUNBRIGHT activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOH, hydroxyl-PEG-aldehyde, carboxylic anhydride type-PEG, functionalized PEG-phospholipid), and other similar and/or suitable reactive PEGs as selected by those skilled in the art for their particular application and usage.

The novel OXM derivative peptides of the present invention can also contain two PEG moieties that are covalently attached via a carbamate or an amide linkage to a spacer moiety, wherein the spacer moiety is covalently bonded to the tertiary amide linker of the peptide. Each of the two PEG moieties used in such embodiments of the present invention may be linear and may be linked together at a single point of attachment. In one embodiment of the invention, each PEG moiety has a molecular weight of about 10 kilodaltons (10K) to about 60K (the term "about" indicating that in preparations of PEG, some molecules will weigh more, and some less, than the stated molecular weight). Each of the two PEG moieties may have a molecular weight of about 20K to about 40K. One skilled in the art will be able to select the desired polymer size based on such considerations as the desired dosage; circulation time; resistance to proteolysis; effects, if any, on biological activity; ease in handling; degree or lack of antigenicity; and other known effects of PEG on a therapeutic peptide.

In an embodiment of the present invention, the polymer backbone of the N-maleimidyl polymer derivative is a poly(alkylene glycol), copolymer thereof, terpolymer thereof, or mixture thereof. Examples include poly(ethylene glycol), poly(propylene glycol), and copolymers of ethylene glycol and propylene glycol. As explained in greater detail below, more preferred embodiments of the invention utilize PEG polymers, such as bifunctional PEG, multiarmed PEG, forked PEG, branched PEG, pendent PEG, and PEG with degradable linkages therein. However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including bifunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(-PEG-OH)_m$ in which R is derived from a core moiety, such as glycerol, glycerol oligomers, or pentaerythritol, and m represents the number of arms. Multi-armed PEG molecules, such as those described in U.S. Pat. No. 5,932,462, which is incorporated by reference herein in its entirety, can also be used as the polymer backbone.

Those of ordinary skill in the art will recognize that the foregoing list for substantially water soluble and non-peptidic polymer backbones is by no means exhaustive and is merely illustrative, and that all polymeric materials having the qualities described above are contemplated.

The sites of PEGylation on the OXM derivatives of the present invention are chosen taking into account the structure of OXM and its interactions with glucagon and GLP-1 receptors. Hence, the PEGylation is preferably site-specific. PEGylation at the thiol side-chain of cysteine has been widely reported (see, e.g., Caliceti & Veronese, 2003). If there is no Cys residue in the peptide, it can be introduced through substitution. The OXM derivatives of the present invention may be PEGylated through the side chains of cysteine. The OXM derivatives may contain Cys(mPEG)teine. The mPEG in Cys (mPEG)teine can have various molecular weights. The range of the molecular weight is preferably 5 kDa to 200 kDa, more 5 kDa to 100 kDa, and further preferably 20 kDa to 60 kDA. The mPEG can be linear or branched. For instance, the Cys (mPEG)teine of present invention may be $C_1$, $C_2$, $C_3$ or $C_6$. As exemplified herein, $C_1$ is Cys(mPEG)teine with a linear mPEG with a molecular weight of 5 kDa (Cys(mPEG)$_5$ kDa) (e.g., MPEG-MAL-5000, NEKTAR 2F2MOH01); $C_2$ is Cys (mPEG)teine with a linear mPEG with a molecular weight of 20 kDa (Cys(mPEG)20 kDa) (e.g., MPEG-MAL-20K, NEKTAR 2F2M0P01); $C_3$ is Cys(mPEG)teine with a branched mPEG with a molecular weight of 40 kDa (Cys(mPEG)$_2$40 kDa) (e.g., MPEG2-MAL-40K, NEKTAR 2D3Y0T01 or Y Shape PEG Maleimide, MW40K (JenKem Technology, item number Y-MAL-40K or SUNBRIGHT GL2-400MA Maleimide, (NOF Corporation) and $C_6$ is Cys(mPEG)teine with a branched mPEG with a molecular weight of 60 kDa (Cys (mPEG)$_2$60 kDa) (e.g., MPEG2-MAL-60K, NEKTAR 2D3Y0V01).

Alternatively, the cysteine residues in the OXM derivatives can also be derivatized with cholesterol via the side-chain thiol. Examples of cholesteryl OXM derivatives include: OXM36, OXM59, OXM65, OXM70, OXM76, OXM82, OXM88, and OXM101.

1.3. Other Modifications

The N-terminal Histidine $H_x$ can be mutated with derivatives from the group consisting of His, $H_1$=Imidazole-lactic acid (ImiH); desamino-His ($\Delta NH_2$—H), acetyl His, pyroglutamyl His(PyrH, N-methyl-His (Me-H), N,N-dimethyl-His (Me$_2$-H); Benzoyl His (Bz-H), Benzyl His (Bzl-H) and Phe. Acetylation and other modification and N-terminal capping groups at the N-terminus may stabilize OXM against DP-IV cleavage, while the amidation of C-terminus may prevent potential degradation in vivo by carboxypeptidases. OXM derivatives with N-terminal modifications include OXM14, and OXM16-22.

As illustrated in the examples, equimolar doses of OXM2 and OXM3 were effective in reducing overnight body weight gain in mice fed ad libitum, whereas similar doses of OXM1 and wild type or native (wt) Oxm were not efficacious in this model. OXM3 had the highest in vivo efficacy in dose-dependently reducing overnight body weight gain, likely reflecting its higher potency against GLP-1R compared to OXM2, which has a bulkier PEG moiety that likely interferes with receptor binding. For the PEGylated OXM derivatives, increased in vivo efficacy relative to wt OXM suggests that some stabilization against proteolysis, and for renal clearance, is induced by PEGylation alone, since both OXM2 and OXM3 are significantly less potent than native OXM against GLP-1R in vitro.

Additionally, a blood component may be utilized to stabilize the peptide. Preferred blood components comprise proteins such as immunoglobulins, serum albumin, ferritin, steroid binding proteins, transferrin, thyroxin binding protein, alpha.-2-macroglobulin, haptoglobin and the like.

2. Synthesis of the OXM Derivatives 2.1. The Synthesis of Peptides

The following general procedure was used to synthesize some of the OXM derivatives. Solid phase peptide synthesis was performed using Fmoc chemistry under batch or continuous flow conditions (see, for example, Pennington and Dunn, Peptide Synthesis Protocols (1994), vol. 35) using PEG-polystyrene resins. Peptides were cleaved from the resin and deprotected using trifluoroacetic acid (TFA), and cation scavengers such as phenol triisopropylsilane, and water. Peptides were precipitated with cold methyl-t-butyl ether and the precipitated peptide was washed twice with cold ether prior to lyophilization. Peptide identity was confirmed by reversed-phase HPLC on a C4 column using water/acetonitrile with 0.1% TFA as typical mobile phases, and by electrospray mass spectrometry. Peptides were purified to $\geq 95\%$ by reverse phase HPLC.

2.2 PEGylation of Peptides

Peptides are first synthesized and are then PEGylated at the thiol side-chain of cysteine. The following general procedure was used for PEGylation of peptides.

PEGylation reactions were run between a thiolated peptide precursor and a maleimide-mPEG to form a thioether bond. The reaction was run at a pH 7.3 and the maleimide-mPEG amount ranged from 0.5 to 10-fold molar excess with respect to the thiolated peptide. The PEGylated OXM peptide was then isolated using reverse-phase HPLC or ion-exchange chromatography followed by size exclusion chromatography. Finally, PEGylated peptides were characterized using analytical RP-HPLC, and MALDI tof mass spectrometry.

3. Implications of OXM-Based Therapy

OXM-based therapy has the potential to favorably impact both obesity and diabetes. Weight loss efficacy and reduction in food intake upon peripheral administration of OXM has been well validated in humans. Studies by the present inventors have shown that peripherally administered porcine OXM is sufficient to reduce short term food intake and overnight body weight gain in mice. Although the incretin (antihyperglycemic) activity of OXM has not been well investigated to date, it has been demonstrated for the first time that the glucose lowering activity of OXM is comparable to that of GLP-1 in a mouse intraperitoneal glucose tolerance test (IP-GTT). Like GLP-1, OXM induces robust glucose stimulated insulin secretion (GSIS) from static isolated murine islets and perfused rat pancreata (Jarrousse et al., *Endocrinology*, 115: 102-105 (1984)), suggesting a low risk of hypoglycemia compared to conventional insulin secretagogues. In rats, negligible effects of OXM on gastric emptying have been reported (Dakin et al., *Endocrinology*, 145:2687-2695 (2004)). In mice, OXM reduces gastric emptying by ~25% at a maximally efficacious dose for glucose lowering, which is less than that produced by a maximally efficacious dose of the GLP-1 receptor agonist exendin 4 (47% reduction). Potentially benign effects of OXM on gastric emptying in humans may therefore play a role in the enhanced tolerability of this peptide hormone compared to current GLP-1 mimetics.

It is suggested that the polypeptides of the present invention may be useful for the treatment of obesity and/or diabetes. Secondary indications are metabolic syndrome, hyperglycemia, impaired fasting glucose, and other prediabetic states. Alternate indications for the polypeptides of the present invention include any and all indications for GLP-1 such as irritable bowel syndrome and other absorptive diseases of the gut, ischemia, stroke, and neurological disorders including anxiety, impaired cognition, and Alzheimer's disease.

The peptidyl nature of OXM precludes oral therapy with the native hormone. By contrast, the OXM derivatives presented herein may be administered as a pharmaceutical composition comprising one of the polypeptides of the present invention in combination with a pharmaceutically acceptable carrier which is suitable for administration by a variety of routes, including but not limited to oral, intranasal, sublingual, intraduodenal, subcutaneous, buccal, intracolonic, rectal, vaginal, mucosal, pulmonary, transdermal, intradermal, parenteral, intravenous, intramuscular and intraocular at a dosage range of 0.001 mg/kg to 10 mg/kg, more preferably from 1 μg/kg to 200 mg/kg with a dosing frequency ranging from twice daily to once per week or longer. The peptide pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc. The peptides are typically combined with a pharmaceutically acceptable carrier or excipient which can contain one or more physiologically acceptable compound(s) that may act to stabilize the composition or to increase or decrease the absorption of the active agent(s). Physiologically acceptable compounds can include, for example, carbohydrates, such as glucose, sucrose, or dextran, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers. Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The peptides can be administered in the native form or, if desired, in the form of salts provided the salts are pharmaceutically acceptable. Salts of the active agents may be prepared using standard procedures known to those skilled in the art of synthetic organic chemistry. Polypeptides of the present invention, as detailed in the Examples, were prepared as acetate salts.

An OXM polypeptide of the instant invention can be used in combination with other agents used in the treatment or prevention of diseases implicating the GLP1-R. Specific compounds of use in combination with a polypeptide of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a polypeptide of the present invention include: those described in WO03/077847, including: N[3-(4-chlorophenyl)-2(S)-phenyl-[(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-

2-methylpropyl}azetidin-1-yl)methyl]benionitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl-]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(1H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(8)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a polypeptide of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro[7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-aisobenzofuran-1(3H), 1'-cyclohexane]-4'-carboxamide, trans-3-oxo-N-(2-phenyl-1,2,3-triazol-4-yl)spiro[6-azaisobenzofuran-1(3H), 1'-cyclohexane]-4'-carboxamide, and pharmaceutically acceptable salts and esters thereof.

Specific ACC-1/2 inhibitors of use in combination with a polypeptide of the present invention include: 1'-[(4,8-dimethoxyquinolin-2-yl)carbonyl]-6-(1H-tetrazol-5-yl)spiro[chroman-2,4'-piperidin]-4-one, (5-{1'-[4,8-dimethoxyquinolin-2-yl)carbonyl]-4-oxospiro[chroman-2,4'-piperidin]-6-yl}-2H-tetrazol-2-yl)methyl pivalate, 5-{1'-[(8-cyclopropyl-4-methoxyquinolin-2-yl)carbonyl]-4-oxospiro[chroman-2,4'-piperidin]-6-yl}nicotinic acid, 1'-(8-methoxy-4-morpholin-4-yl-2-naphthoyl)-6-(1H-tetrazol-5-yl)spiro[chroman-2,4'-piperidin]-4-one, and 1'-[(4-ethoxy-8-ethylquinolin-2-yl)carbonyl]-6-(1H-tetrazol-5-yl)spiro[chroman-2,4'-piperidin]-4-one, and pharmaceutically acceptable salts thereof.

Specific MCH1R antagonist compounds of use in combination with a polypeptide of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(25)-1-ethylazetidin-2-yl]methoxy}phenyl)pyridin-2(1H)-one, or a pharmaceutically acceptable salt thereof.

Specific DP-IV inhibitors of use in combination with a polypeptide of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Additionally, other peptide analogs and mimetics of the incretin hormone glucagon-like peptide 1(GLP-1), may also be of use in combination with a polypeptide of the present invention.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1

Synthesis of Oxyntomodulin (OXM) Analogs

The peptide OXM analogs (see Table 1) were synthesized by solid phase using Fmoc/tBu chemistry on a peptide multisynthesizer APEX 396 (Advanced Chemtech) using a 40-well reaction block. Each peptide was synthesized in a single well. For peptide amides 0.1 g of a resin Fmoc-Linker AM-Champion, 1% cross-linked (Biosearch Technologies, Inc.) and a PEG-PS based resin derivatized with a modified Rink linker p-[(R,S)-α-[9H-Fluoren-9-yl-methoxyformamido]-2,4-dimethoxybenzyl]-phenoxyacetic acid (Rink, H., 1987, *Tetrahedron Lett.* 28:3787-3789; Bernatowicz, M. S. et al., 1989, *Tetrahedron Lett.* 30:4645-4667) was used. For peptide acids, 0.1 g of Champion resin, 1% cross-linked (Biosearch Technologies, Inc.) was used, which was previously derivatized with a hydroxymethylphenoxymethyl handle. All the amino acids were dissolved at a 0.5 M concentration in a solution of 0.5M HOBt (Hydroxybenzotriazole) in DMF. The acylation reactions were performed for 60 min with 6-fold excess of activated amino acid over the resin free amino groups. The amino acids were activated with equimolar amounts of HBTU (2-(1H-benzotriazole-1-yl)-1,1,3,3-tetramethyluronium hexafluorophosphate) and a 2-fold molar excess of DIEA (N,N-diisopropylethylamine).

Alternatively, the peptides were synthesized by solid phase using Fmoc/t-Bu chemistry on a Pioneer Peptide Synthesizer (Applied Biosystems). In this case, all the acylation reactions were performed for 60 minutes with a 4-fold excess of activated amino acid over the resin free amino groups following the end of peptide assembly on the synthesizer. The side chain protecting groups were: tert-butyl for Asp, Glu, Ser, Thr and Tyr; trityl for Asn, Cys, Gln and His; tert-butoxy-carbonyl for Lys, Trp; and, 2,2,4,6,7-pentamethyldihydrobenzofuran-5-sulfonyl for Arg. For the OXM2 and OXM3 peptides, the acetylation reaction was performed at the end of the peptide assembly by reaction with a 10-fold excess of acetic anhydride in DMF.

For OXM14, L-pyroglutamic acid was acylated by reaction with equimolar amounts of DIPC (diisopropylcarbodiimide) and HOBt (N-hydroxybenzotriazole) with a 4-fold excess of activated acylant over the resin free amino groups.

For OXM16, imidazole-lactic acid (Imi-H) was acylated by reaction with equimolar amounts of PyBOP (Benzotriazole-1-yl-oxy-tris-pyrrolidino-phosphonium hexafluorophosphate), HOBt and a 2-fold molar excess of DIEA (N,N-diisopropylethylamine) with a 4-fold excess of activated acylant over the resin free amino groups.

For OXM17, N-methyl-His (Me-H) was acylated by reaction with equimolar amounts of HBTU (2-(1H-benzotriazole-1-yl)-1,1,3,3-tetramethyluronium hexafluorophosphate) and a 2-fold molar excess of DMA. The acylation reaction was performed for 180 min with a 3-fold excess of activated acylant over the resin free amino groups.

For OXM18, desamino-His ($\Delta NH_2$—H) was acylated by reaction with equimolar amounts of HBTU and a 2-fold molar excess of DIEA. The acylation reaction was performed for 180 min with a 3-fold excess of activated acylant over the resin free amino groups.

For OXM19, N,N-dimethyl-His ($Me_2$-H) was acylated by reaction with equimolar amounts of HBTU and a 2-fold molar excess of DMA. The acylation reaction was performed overnight with a 3-fold excess of activated acylant over the resin free amino groups.

For OXM20, benzoyl-His (Bz-H) was acylated by reaction with equimolar amounts of HBTU and a 2-fold molar excess of DIEA. The acylation reaction was performed for 240 min with a 3-fold excess of activated acylant over the resin free amino groups.

For OXM21, Benzyl-His (Bzl-H) was acylated by reaction with equimolar amounts of HBTU and a 2-fold molar excess of DIEA. The acylation reaction was performed overnight with a 3-fold excess of activated acylant over the resin free amino groups.

At the end of the synthesis, the dry peptide-resins were individually treated with 20 mL of the cleavage mixture, 88% TFA, 5% phenol, 2% triisopropylsilane and 5% water (Sole, N. A. and G. Barany, 1992, *J. Org. Chem.* 57:5399-5403) for 1.5 hours at room temperature. Each resin was filtered and the solution was added to cold methyl-t-butyl ether in order to precipitate the peptide. After centrifugation, the peptide pellets were washed with fresh cold methyl-t-butyl ether to remove the organic scavengers. The process was repeated twice. Final pellets were dried, resuspended in $H_2O$, 20% acetonitrile, and lyophilized.

The synthesis of peptide OXM54 was performed by dissolving the thiol containing OXM peptide precursor (SEQ ID NO: 41) in TrisHCl 0.1M pH 8, guanidinium chloride 6M. A 10 molar excess of iodoacetamide was added. After 1 hour incubation, the peptide solution was purified by HPLC.

The synthesis of peptide OXM55 was performed by dissolving the thiol containing OXM peptide precursor (SEQ ID NO: 64) in TrisHCl 0.1M pH 8, guanidinium chloride 6M. A 10 molar excess of iodoacetamide was added to this solution. After 1 hour incubation, the peptide solution was purified by HPLC.

The crude peptides were purified by reverse-phase HPLC using semi-preparative Waters RCM Delta-Pak™ $C_{-4}$ cartridges (40×200 mm, 15 um) and using as eluents (A) 0.1% TFA in water and (B) 0.1% TFA in acetonitrile. The following gradient of eluent B was used: 20%-20% over 5 min and 20%-35% over 20 min, flow rate 80 mL/min. Analytical HPLC was performed on a Phenomenex, Jupiter $C_4$ column (150×4.6 mm, 5 μm) with the following gradient of eluent B: 20%-40% B (in 20 min)-80% (in 3 min), flow rate 1 mL/min. The purified peptide was characterized by electrospray mass spectrometry on a Micromass LCZ platform.

Example 2

PEGylation of Oxyntomodulin (OXM) Analogs

PEGylation reactions were run under conditions permitting thioester bond formation. The PEGylated OXM peptide was then isolated using reverse-phase HPLC or ion exchange chromatography and size exclusion chromatography (SEC). PEGylated OXM analogs were characterized using RP-HPLC, HPLC-SEC and MALDI-T of Mass Spectrometry.

OXM33, 34, 35, 36 and 54 peptides were synthesized from the thiol-containing OXM peptide precursor (SEQ ID NO: 41) to produce derivatives with PEG covalently attached via a thioether bond.

Synthesis of OXM433

10 mg of peptide precursor (2.2 μmoles) were dissolved in 0.2 mL of HEPES 0.1M pH 7.3, Guanidinium Chloride 6M, 2 mM EDTA. 22 mg of MPEG-MAL-5000 (NEKTAR 2F2MOH01) (4.4 μmoles) dissolved in 0.4 mL HEPES 0.1M, pH 7.3 (1:2 mole/mole ratio of peptide to PEG) was added to this solution. After 1 hour incubation, the PEGylated peptide was purified by RP-HPLC and characterized by MALDI-T of.

Synthesis of OXM34

10 mg of peptide precursor (2.2 μmoles) were dissolved in 0.2 mL of HEPES 0.1M pH 7.3, Guanidinium Chloride 6M, 2 mM EDTA. 80 mg of MPEG-MAL-20K (NEKTAR 2F2M0P01) (4.0 μmoles) dissolved in 0.5 mL HEPES 0.1M, pH 7.3 (1:1.8 mole/mole ratio of peptide to PEG) was added to this solution. After 1 hour incubation, the PEGylated peptide was purified by RP-HPLC and characterized by MALDI-T of.

Synthesis of OXM35

10 mg of peptide precursor (0.92 μmoles) were dissolved in 0.4 mL of HEPES 0.1M pH 7.3, Guanidinium Chloride 6M, 2 mM EDTA. 70 mg of MPEG2-MAL-40K (NEKTAR 2D3Y0T01) (1.7 μmoles) dissolved in 0.8 mL HEPES 0.1M, pH 7.3 in a 1:1.8 mole/mole ratio of peptide to PEG was added to this solution. After 1 hour incubation, the PEGylated peptide was purified by RP-HPLC and characterized by MALDI-T of.

The control peptide OXM54, was prepared by incubating the thiol containing peptide precursor with 10 eq. of iodoacetamide in 0.1 M TrisHCl pH 7.5, 6M guanidinium chloride. After 30 minutes incubation the peptide was purified by RP-HPLC and characterized by electrospray mass spectrometry.

The peptides OXM 56, 57, 58 were synthesized from the thiol containing OXM peptide precursor (SEQ ID NO: 64) to produce derivatives with PEG covalently attached via a thioether bond.

Synthesis of OXM56

5 mg of peptide precursor (1.1 μmoles) were dissolved in 0.2 mL of HEPES 0.1M pH 7.3. 57 mg of MPEG-MAL-5000 (NEKTAR 2F2MOH01) (11.4 μmoles) dissolved in 0.4 mL HEPES 0.1M, pH 7.3 (1:10 mole/mole ratio of peptide to PEG) was added to this solution. After 1 hour incubation, the PEGylated peptide solution was acidified to 1% acetic acid and purified by cation exchange chromatography (DCC) on fractogel TSK CM-650S with a linear gradient of NaCl in sodium acetate 50 mM pH 4.8. The DCC purified PEGylated-peptide was further purified by size-exclusion chromatography (SEC) and characterized by MALDI-T of.

Synthesis of OXM57

10 mg of peptide precursor (2.2 μmoles) were dissolved in 0.2 mL of DMSO. 50 mg of MPEG-MAL-20K (NEKTAR 2F2M0P01) (2.5 μmoles) dissolved in 0.6 mL HEPES 0.1M pH 7.3, 0.3M TRIS(2-carboxy-ethyl)phosphine with a 1:1.13 mole/mole ratio of peptide to PEG was added to this solution. After 1 hour incubation, the PEGylated peptide was purified by RP-HPLC and characterized by MALDI-T of.

Synthesis of OXM58

10 mg of peptide precursor (0.92 μmoles) were dissolved in 0.4 mL of HEPES 0.1M pH 7.3, Guanidinium Chloride 6M, 2 mM EDTA. 70 mg of MPEG2-MAL-40K (NEKTAR 2D3Y0T01) (1.7 μmoles) dissolved in 0.8 mL HEPES 0.1M, pH 7.3 (1:1.8 mole/mole ratio of peptide to PEG) was added to this solution. After 1 hour incubation, the PEGylated peptide was purified by RP-HPLC and characterized by MALDI-T of.

The control peptides OXM102, OXM112, and OXM116 were prepared by incubating the thiol-containing peptide precursor with 10 eq. of iodoacetamide in 0.1 M TrisHCl pH 7.5, 6M guanidinium chloride. After 30 minutes incubation the peptide was purified by RP-HPLC and characterized by electrospray mass spectrometry.

Synthesis of OXM103, OXM105, OXM107, OXM113

10 mg of the corresponding peptide precursors (2.26 μmoles) were dissolved in 2 mL of urea 8M, HEPES 0.1M pH 7.3, 2 mM EDTA. 109 mg of MPEG2-MAL-40K (NEKTAR 2D3Y0T01) (2.71 μmoles) dissolved in $H_2O$ (1:1.2 mole/mole ratio of peptide to PEG) was added to this solution. After 1 hour incubation, the PEGylated peptide solution was acidified to 1% acetic acid and purified by cation exchange chromatography (IXC) on TSK CM-650S with a linear gradient of NaCl in sodium acetate 50 mM pH 4.8. The DCC purified PEGylated-peptide was further purified by SEC and characterized by MALDI-T of.

Synthesis of OXM109

10 mg of the corresponding peptide precursors (2.25 μmoles) were dissolved in 2 ml urea 8M, HEPES 0.1M pH 7.3, 2 mM EDTA. 108 mg of MPEG2-MAL-40K (NEKTAR 2D3Y0T01) (2.7 μmoles) dissolved in 2 mL $H_2O$ (1:1.2 mole/mole ratio of peptide to PEG) was added to this solution. After 1 hour incubation, the PEGylated peptide solution was acidified to 1% acetic acid and purified by cation exchange chromatography (DCC) on TSK CM-650S with a linear gradient of NaCl in sodium acetate 50 mM pH 4.8. The IXC purified PEGylated-peptide was further purified by SEC and characterized by MALDI-T of.

Synthesis of OXM117

10 mg of the corresponding peptide precursors (2.19 μmoles) were dissolved in 2 mL of urea 8M, HEPES 0.2M pH 6.5, 2 mM EDTA. 105 mg of $MPEG_2$-MAL-40K (NEKTAR 2D3Y0T01) (2.63 μmoles) dissolved in $H_2O$ (1:1.2 mole/mole ratio of peptide to PEG) was added to this solution. After 1 hour incubation, the PEGylated peptide solution was acidified to 1% acetic acid and purified by cation exchange chromatography (DCC) on TSK CM-650S with a linear gradient of NaCl in sodium acetate 50 mM pH 4.8. The DCC purified PEGylated-peptide was further purified by SEC and characterized by MALDI-T of.

Synthesis of OXM125

10 mg of the corresponding peptide precursors (2.26 μmoles) were dissolved in 2 mL of Urea 8M, HEPES 0.25M pH 6.5, 2 mM EDTA. 105 mg of $MPEG_2$-MAL-40K (NEKTAR 2D3Y0T01) (2.71 μmoles) dissolved in $H_2O$ (1:1.2 mole/mole ratio of peptide to PEG) was added to this solution. After 1 hour incubation, the PEGylated peptide solution was acidified to 0.2% formic acid pH 2.8 and purified by cation exchange chromatography (IXC) on TSK SP-5PW with a linear gradient of NaCl in formic acid 0.2%. The DCC purified PEGylated-peptide was further purified by SEC and characterized by MALDI-T of.

Synthesis of OXM129

10 mg of the corresponding peptide precursors (2.26 μmoles) were dissolved in 2 mL of Urea 8M, HEPES 0.25M pH 6.5, 2 mM EDTA. 109 mg of $MPEG_2$-MAL-40K (NEKTAR 2D3Y0T01) (2.72 μmoles) dissolved in $H_2O$ (1:1.2 mole/mole ratio of peptide to PEG) was added to this solution. After 1 hour incubation, the PEGylated peptide solution was acidified to 0.2% formic acid and purified by cation exchange chromatography (DCC) on TSK SP-5PW with a linear gradient of NaCl in formic acid 0.2%. The DCC purified PEGylated-peptide was further purified by SEC and characterized by MALDI-T of.

Example 3

Design and Synthesis of Peptide Sequences

The biological activity of different PEG sizes (mPEG)5 kDa, (mPEG)$_2$40 kDa, (mPEG)$_2$40 kDa and (mPEG)$_2$60 kDa was compared in a series of experiments which demonstrated that the optimal PEG size to confer the maximal and durable activity in the mice is generally 40 kDa.

The peptide OXM103 (Aib (α) at position 2) was designed to explore position 20 within the oxyntomodulin sequence as the site for conjugation with (mPEG)$_2$40 kDa. OXM102 is a control peptide (CH$_2$CONH$_2$), in which the side-chain thiol (of cysteine at position 20) was reacted with iodoacetamide.

The peptide OXM105 (Aib (α) at position 2) was designed to explore position 21 within the oxyntomodulin sequence, as the site for conjugation with (mPEG)$_2$40 kDa. OXM104 is a control peptide (CH$_2$CONH$_2$), in which the side-chain thiol (of cysteine at position 21) was reacted with iodoacetamide.

The peptide OXM107 (Aib (α) at position 2, Met(O) at position 27) was designed to explore position 24 within the oxyntomodulin sequence, as the site for conjugation with (mPEG)$_2$40 kDa. OXM106 is a control peptide (CH$_2$CONH$_2$), in which the side-chain thiol (of cysteine at position 24) was reacted with iodoacetamide.

The peptide OXM109 (Aib (α) at position 2,) was designed to explore position 28 within the oxyntomodulin sequence, as the site for conjugation with (mPEG)$_2$40 kDa. OXM108 is a control peptide (CH$_2$CONH$_2$), in which the side-chain thiol (of cysteine at position 28) was reacted with iodoacetamide.

The peptide designated OXM141 has a Gln to Asp mutation at position 3, which confers specific selectivity to the GLP1-receptor. The peptide OXM141, which has a Gln to Asp mutation at position 3, Met(O) at position 27, and two conjugation sites at position 20 and 38, was designed to explore the potential of having a peptide conjugated with both a cholesterol group at C38 and PEG at position C20.

The peptide OXM142 (Aib (α), Met(O) at position 27, and two conjugation sites at position 20 and 38) was designed to explore the potential of having a peptide conjugated with both a, cholesterol group at C38 and PEG at position C20.

FIG. 14 summarizes the in vitro activity data for GLP1R and GCG receptors (also showing the GLP-1R and GLGR specificities) in tabular form. The (mPEG)$_2$40 kDa conjugate at position C20 retains activity on both receptors, therefore OXM103 as is referred to as a +/+ analog, while all the other (mPEG)$_2$40 kDa conjugates lose potency at the GCG receptor. In particular there is a between 2-3 orders of magnitude selectivity towards the GLP-1 receptor over the Gcg receptor for the (mPEG)$_2$40 kDa conjugates at position 38, 24 and 28. Therefore, the analogs OXM107 and 109 are referred to as +/0 analogs.

Figure 15A:
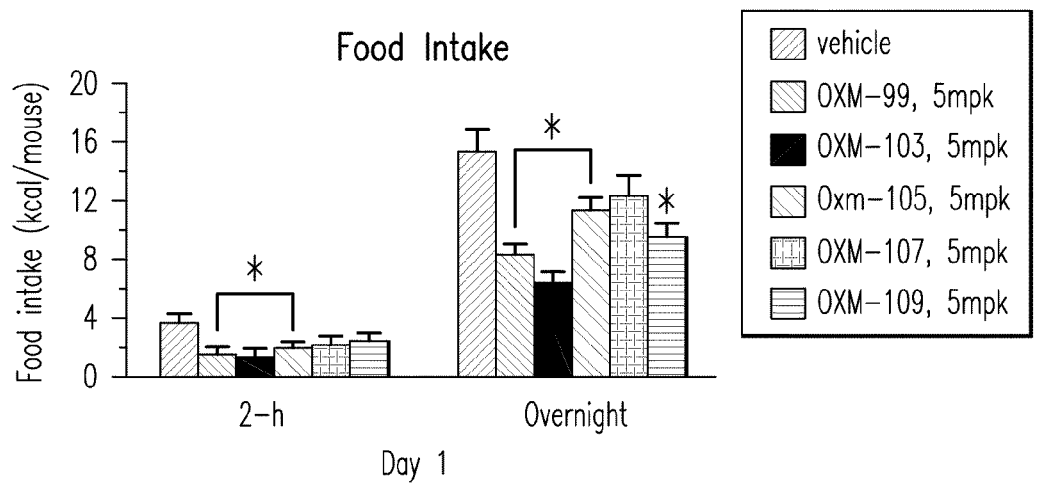
FIG. 15 shows in vivo activity of (mPEG)$_2$40 kDa conjugates on food intake and body weight loss in the DIO mouse model.
Figure 15B:
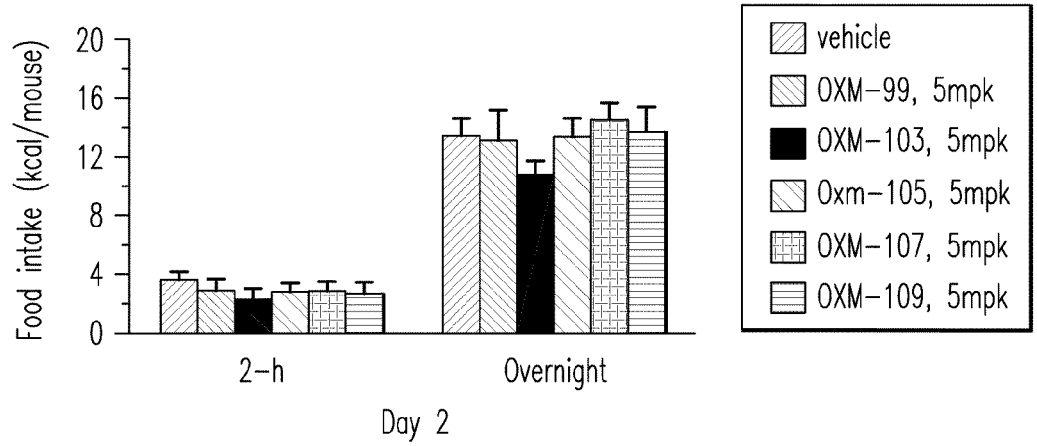
Figure 15C:
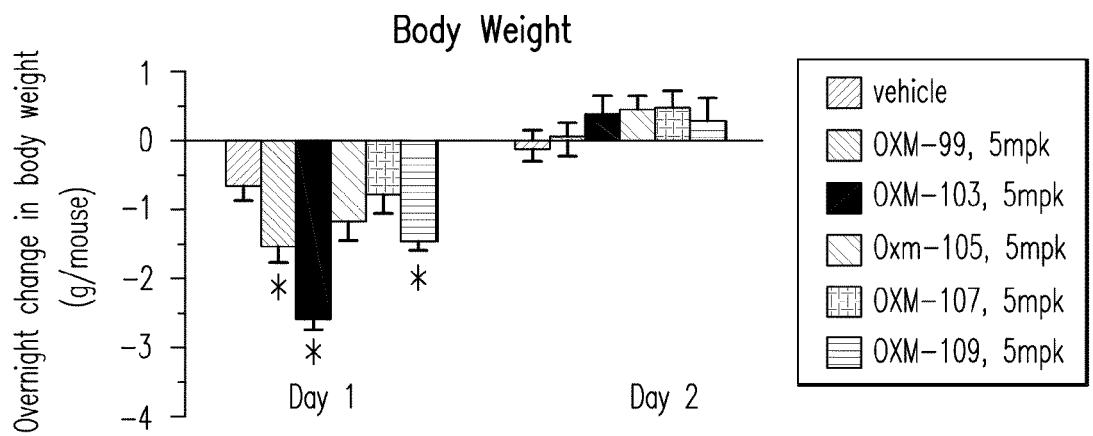

FIG. 15 shows the in vivo activity of the (mPEG)$_2$40 kDa conjugates on food intake and body weight loss on DIO mice. Ad libitum fed, DIO (~51 g each), male C57BL/6 mice were dosed i.p. with either vehicle (water) or Oxm analogs 99, 103, 105, 107, and 109 ~30 min prior to the onset of the dark phase. Food intake measured ~2 h and 18 h (overnight) later on day 1 and 26 and 42 h (overnight) later on day 2. *P<0.05 vs. vehicle, n=5-6 per group).

The peptide OXM110 (D-Ser (s) at position 2,) was designed to explore position 38 within the oxyntomodulin sequence, as the site for conjugation with a lipid such as a palmitoyl group. The palmitoyl group was acylated to the ε-amino group of a lysine added at the C-terminus of the oxyntomodulin sequence.

The peptide OXM113 (desamino-His (ΔNH$_2$—H) at position 1, Aib (α) at position 2, Met(O) at position 27, conjugation site 38) was designed to explore the potential of substituting the wild type (wt) His with a desamino-His at position 1 for protection from DPPIV proteolysis. OXM113 is the (mPEG)$_2$40 kDa conjugate, OXM114 is the cholesteryl conjugate and OXM112 is a control peptide (CH$_2$CONH$_2$), in which the side-chain thiol (of cysteine at position 38) was reacted with iodoacetamide). (OXM111 is the thiolated peptide precursor).

The peptides OXM117 and OXM118 (Aib (α) at position 2, Gln to Asp mutation at position 3, Met(O) at position 27, conjugation site 38) were designed to explore the potential of substituting the wild type Gln with an Asp at position 3. As mentioned above, this mutation confers specific selectivity towards the GLP-1R. OXM117 is the (mPEG)$_2$40 kDa conjugate and the OXM118 is the cholesteryl conjugate. (OXM116 is the thiolated peptide precursor).

The peptide OXM121 (Aib (α) at position 2, Met(O) at position 27, conjugation site 11) was designed to explore position 11 within the oxyntomodulin sequence as the site for the conjugation. OXM121 is the (mPEG)$_2$40 kDa conjugate, OXM119 is the thiolated peptide precursor and OXM120 is a control peptide (CH$_2$CONH$_2$), in which the side-chain thiol (of cysteine at position 11) was reacted with iodoacetamide.

The peptide OXM124 (Aib (α) at position 2, Met(O) at position 27, conjugation site 12) was designed to explore position 12 within the oxyntomodulin sequence as the site for conjugation. OXM124 is the (mPEG)$_2$40 kDa conjugate, OXM122 is the thiolated peptide precursor and OXM123 is a control peptide (CH$_2$CONH$_2$), in which the side-chain thiol (of cysteine at position 12) was reacted with iodoacetamide.

The peptide OXM125 (Aib (α) at position 2, Gln to Asp mutation at position 3, Met(O) at position 27, conjugation site 20) was designed to explore position 20 within the oxyntomodulin sequence as the site for conjugation of (mPEG)$_2$40 kDa as well as the Gln to Asp substitution at position 3 that confers selectivity towards the GLP-1R The peptide OXM127 (Aib (α) at position 2, Met(O) at position 27, conjugation site 22) was designed to explore position 22 within the oxyntomodulin sequence as the site for conjugation for cholesterol. OXM126 is the thiolated peptide precursor).

The peptide OXM129 (desamino-His (ΔNH$_2$—H) at position 1, Aib (α) at position 2, Gln to Asp mutation at position 3, Met(O) at position 27, conjugation site 20) was designed to explore the potential of the following combinations: substituting the wt His with desamino-His at position 1 for protection from DPPIV proteolysis, the Gln to Asp substitution at position 3 that confers selectivity towards the GLP-1R, and conjugation at position 20.

The peptide OXM134 (Aib (α) at position 2, Met(O) at position 27, conjugation site 20) is a(mPEG)$_2$40 kDa conjugate similar to the potent +/+ OXM103 analogue that only differs for the methionine substitution to methionine sulfoxide. This peptide is conjugated at the position 20 therefore displaying a +/+ pattern for GLP1R/GcgR selectivity.

Example 4

C-Terminal Truncated Analogs or GcgK Analogs

C-Terminal Truncated Analogs

A series of peptide OXM C-terminal truncated analogs were designed. An analysis of in vitro activity on both the GLP1 receptor (GLP1R) and the Gcg receptor (GcgR) demonstrated that the OXM sequence can be truncated at the C-terminus to have only one extra lysine residue with respect to wt glucagon, yielding a peptide such as OXM93 that is extremely potent on both the GLP1R and GcgR. The potency of OXM93 is at least one order (and possibly two) of magnitude higher than that of wt OXM. Because there is only one extra Lys residue with respect to Gcg, this new class is referred to as GcgK analogs. FIG. 16 illustrates in vitro potency data for the C-terminal truncated analogs acting at the GLP1 and GCG receptors in tabular form.

C-terminal truncated analogs which are selective GcgK Analogs

Peptides OXM130 and OXM131 were designed to confirm the in vitro analysis and introduce other mutations that are known to confer stability and suitable properties. OXM130 and OXM131 are C-terminal truncated analogues of the same length as OXM93. OXM130 has Aib ($\alpha$) at position 2, while OXM131 has Aib ($\alpha$) at position 2 and a Gln to Asp mutation at position 3 to confer selectivity for the GLP1R.

The following PEGylated analogs were designed based on these truncated sequences:

The peptide OXM136 (Aib ($\alpha$) at position 2, Met(O) at position 27, conjugation site 20) is the (mPEG)$_2$40 kDa conjugate. From prior studies (see above) it is known that the choice of PEG conjugation at position 20 allows for activity on both receptors GLP1R and GcgR, therefore OXM136 would be defined as the prototype Gcg +/+ analogue. (OXM135 is the thiolated peptide precursor).

The peptide OXM138 (Aib ($\alpha$) at position 2, Gln to Asp mutation at position 3, Met(O) at position 27, conjugation site 20) was designed to explore the potential of the following combinations: the Gln to Asp substitution at position 3 that confers selectivity towards the GLP-1R; conjugation at position 20 and mutating the wt Gln to Asp at position 3. Therefore OXM137 would be defined as the prototype GcgK +/0 analog (OXM137 is the thiolated peptide precursor).

FIG. 17 provides in vitro potency data at the GLP1 and GCG receptors for select PEGylated OXM analogs.

Example 5

Peptides with Alternative PEG Moieties

The peptide OXM145 (Aib ($\alpha$) at position 2, Gln to Asp mutation at position 3, Met(O) at position 27, conjugation site 38 with Y Shape PEG Maleimide from JenKem Therapeutics) was produced to explore the potential of using alternative branched 40 kDa PEG moieties. This is the conjugate obtained using a (mPEG)$_2$40 kDa from JenKem Therapeutics (Y-Shaped PEG Maleimide, MW40K, item number Y-MAL-40K and its structure is shown below:

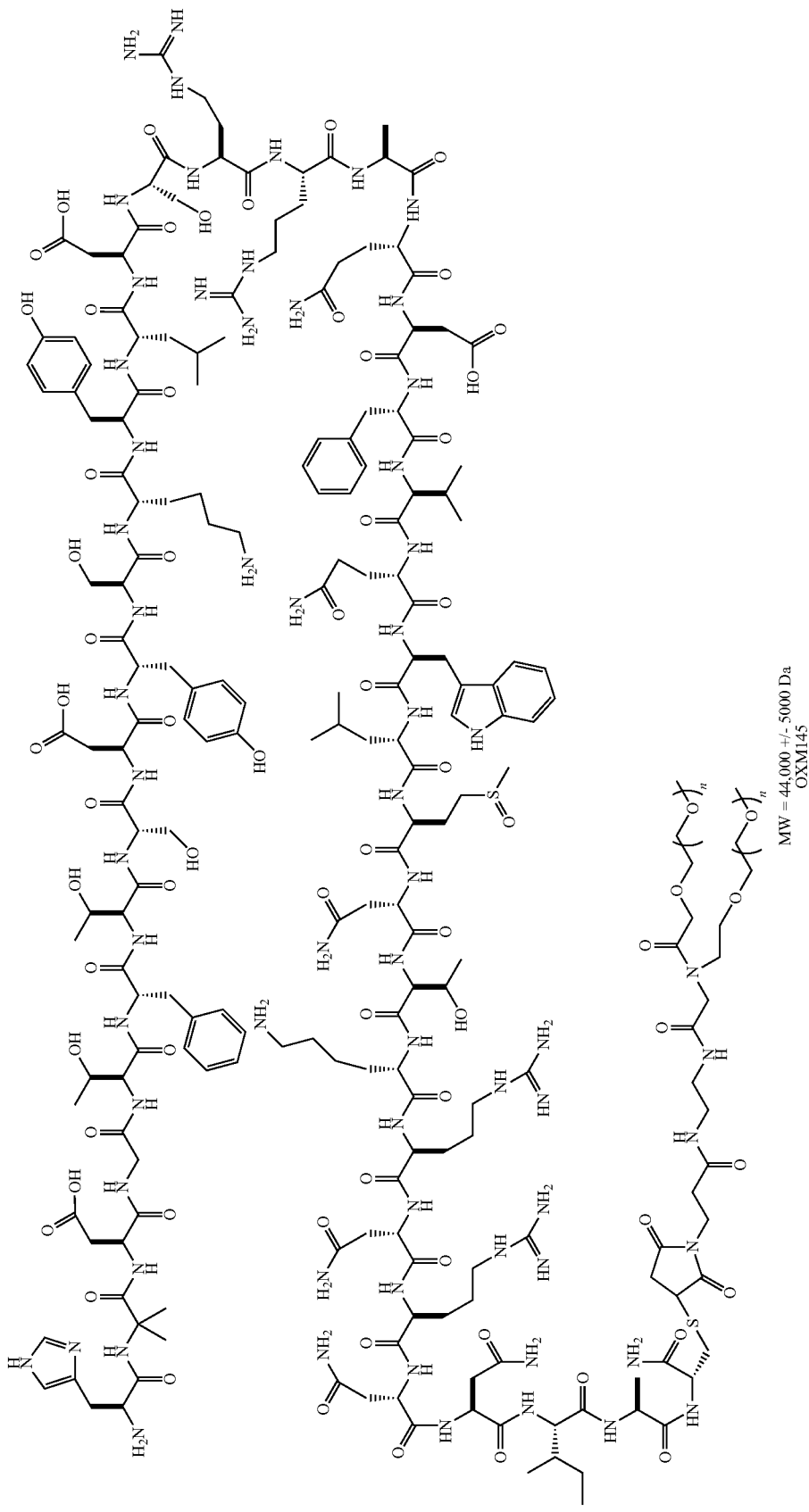

The peptide OXM146 is characterized by Aib (α) at position 2, Gln to Asp mutation at position 3, Met(O) at position 27, conjugation site 38 with SUNBRIGHT GL2-400MA Maleimide from NOF corporation. This is the conjugate obtained using a (mPEG)$_2$40 kDa from NOF Corporation (SUNBRIGHT GL2-400MA Maleimide) and its structure is shown below:

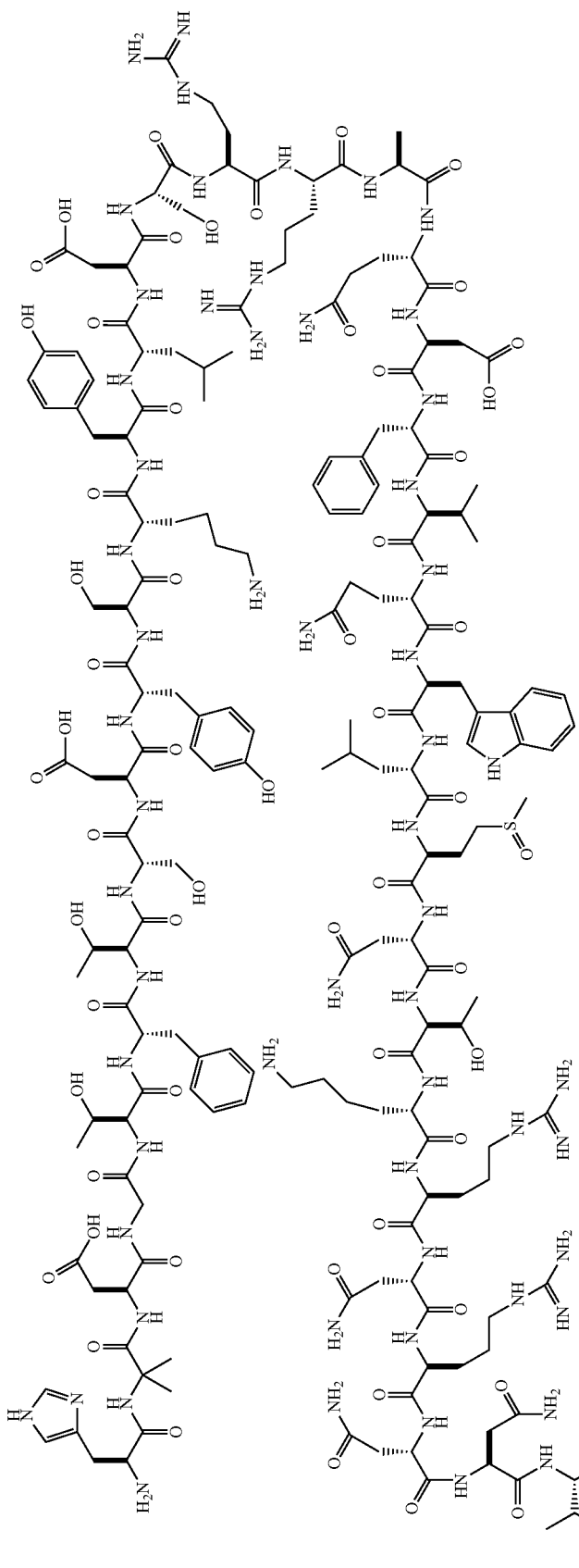

The peptide OXM151 (Aib (α) at position 2, Gln to Asp mutation at position 3, Arg to Glu mutation at position 17, Arg to Ala mutation at position 18, Met(O) at position 27, conjugation site 38) was designed to confer in vivo increased stability to the peptide sequence.

A detailed study was undertaken in which OXM139 was incubated in PBS containing 10% of mouse or human plasma at 37° C. Sample preparation was accomplished by mixing 1 μL of test solution and 1 μL of matrix (α-cyano) directly on the sample plate. After crystallization T of spectrum was collected: Time points at 30, 60, 120 and 720 minutes were analyzed and compared with the same time points of the control test solutions. Within the peptide sequence, the bond between Arg17 and Arg18 has been identified to be a primary hydrolysis site. The bond between Arg18 and Ala19 was also identified as a secondary site of hydrolysis, so it was decided to introduce mutations at sites 17 and 18. Specifically, Arg 17 was mutated to Glu and Arg 18 was mutated to Ala. The peptide OXM153 is the N-ethyl maleimide analog of OXM151. The peptide OXM154 is the conjugate obtained using a (mPEG)$_2$40 kDa from NOF Corporation (SUNBRIGHT GL2-400MA Maleimide).

The peptide OXM152 spans residues 1 to 16 of the Oxyntomodulin sequence (Aib (α) at position 2, Gln to Asp mutation at position 3, Ttds at position 17 as a spacer, Cys at position 18 for conjugation) and is a peptide that can be conjugated to a carrier protein to raise antibodies specific against the 1-16 sequence.

The peptide OXM155 (Aib (α) at position 2, Gln to Asp mutation at position 3, Met(O) at position 27, Ttds at position 38, 5 glutamic residues a position 39-43, Cys at position 44 for conjugation) is another peptide that can be conjugated to a carrier protein to raise antibodies. The addition of glutamic acids at the C terminus is needed for pI modulation that will enable conjugation to the carrier protein, as described in "A Method to Make a Peptide-Carrier Conjugate with a High Immunogenicity," Provisional Application Ser. No. 60/530,867, filed on Dec. 18, 2003, and herein incorporated by reference in its entirety.

Example 6

New Truncated Analogs or GcgK Analogs

The peptide OXM143 (Aib (α), Met(O) at position 27, conjugation site 20) is the N-ethyl maleimide analog of OXM135.

The peptide OXM144 (Aib (α), Gln to Asp mutation at position 3, Met(O) at position 27, and conjugations site at position 20 is the N-ethyl maleimide analog of OXM137.

The peptide OXM147 (Aib (α) at position 2, conjugation site 20) was designed to have a native Methionine residue at position 27 within the GcgK analog series having the conjugation site at C20. The rationale for this design was that a peptide analog with a native methionine is more active on the glucagon receptor.

The peptide OXM148 (Aib (α) at position 2, conjugation site 20) is the N-ethyl maleimide analog of OXM147.

The peptide OXM149 (Aib (α), Gln to Asp mutation at position 3, Met(O) at position 27, conjugations site at position 20 and D-Lysine replacement at position 30) was designed to provide protection in vivo from enzymatic degradation of the C-terminus of the peptide. The peptide OXM150 is the N-ethyl maleimide analog of OXM149.

A similar study of stability was performed on a GcgK series analog OXM144 to determine the primary sites of hydrolysis by incubation with PBS, containing 10% of either mouse or human plasma. In this instance, the bond between Arg17 and Arg18 was identified as a primary hydrolysis site. Also the bond between Arg18 and Ala19 was identified as a secondary site of hydrolysis. For this reason, it was decided to introduce mutations at the sites 17 and 18 also in the GcgK analog series.

Synthesis of OXM145

54 mg of the corresponding peptide precursors (11.8 μmoles) were dissolved in 2 mL of Urea 8M, HEPES 0.2M pH 6.5, 2 mM EDTA. 569 mg (14.2 μmoles) of Y-Shaped PEG Maleimide, MW40K (JenKem Technology, item number Y-MAL-40K) dissolved in H$_2$O (1:1.2 mole/mole ratio of peptide to PEG) was added to this solution. After 1 hour incubation, the PEGylated peptide solution was acidified to 0.2% formic acid pH 2.8 and purified by cation exchange chromatography (IXC) on TSK SP-5PW with a linear gradient of NaCl in formic acid 0.2%. The IXC purified PEGylated-peptide was further purified by SEC and characterized by MALDI-T of.

Synthesis of OXM146

55 mg of the corresponding peptide precursors (12 moles) were dissolved in 2 mL of Urea 8M, HEPES 0.2M pH 6.5, 2 mM EDTA. 531 mg (13.2 μmoles) of SUNBRIGHT GL2-400MA Maleimide, (NOF Corporation) dissolved in H$_2$O (1:1.1 mole/mole ratio of peptide to PEG) was added to this solution. After 1 hour incubation, the PEGylated peptide solution was acidified to 0.2% formic acid pH 2.8 and purified by cation exchange chromatography (IXC) on TSK SP-5PW with a linear gradient of NaCl in formic acid 0.2%. The DCC purified PEGylated-peptide was further purified by SEC and characterized by MALDI-T of.

Example 7

Measurement of GLP-1 Receptor (GLP-1R) Signaling Using a Cyclic AMP (cAMP) Homogenous Time Resolved Fluorescence (HTRF) Assay and Evaluation of Resistance to DP-IV Chinese hamster ovary (CHO) cell lines stably transfected with a mutant form of the human GLP-1R with bioactivity similar to that of the native receptor were maintained in complete Iscove's Modified Dulbecco's Medium (IMDM) media containing fetal bovine serum (FBS), penicillin-streptomycin, hypoxanthine-thymidine and G418. A homogenous time resolved fluorescence (HTRF) assay for GLP-1 receptor activation was used to measure cAMP accumulation in transfected cells upon incubation with peptides of this invention following the manufacturer's instructions (Cis Bio), with the exception that cells were incubated with ligand, XL-665 and anti-cAMP cryptate at 37° C. The assay was conducted in a 96 half-well plate format and the plate was read using a Perkin Elmer Envision plate reader. For polypeptides and polypeptide fragments/derivatives of this invention, "activation" of the GLP-1 receptor in a cAMP HTRF assay is induction of a maximal activity that is at least about 60% and up to about 200% of the maximal activity induced by the native human OXM sequence with a relative potency of at least 0.04% up to about 1000%. "Relative potency" is the EC$_{50}$ of native human OXM divided by the EC$_{50}$ of the polypeptide of the invention, multiplied by 100. "EC$_{50}$" is the concentration of a polypeptide at which 50% of the maximal activity is achieved.

Figure 2:
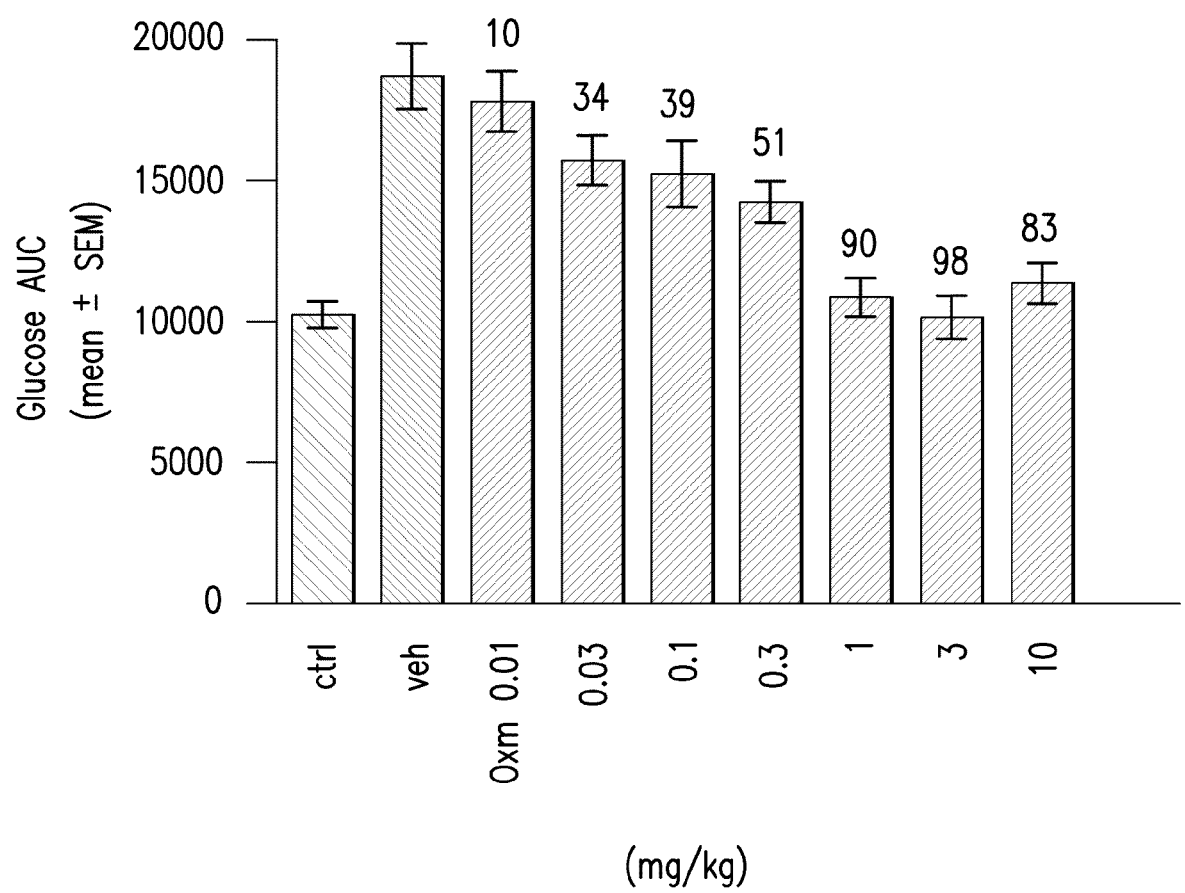
FIG. 2 shows incretin activity of porcine oxyntomodulin in the lean mouse intraperitoneal glucose tolerance test (IP-GTT). % inhibition of glucose excursion is indicated for each group. "ctrl"=vehicle-treated saline-challenged mice, "veh"=vehicle-treated dextrose-challenged mice.

To measure resistance to DP-IV cleavage, a 5 μM solution of peptide was pre-incubated with 10 nM of recombinant soluble human DP-IV in 100 μl assay buffer (10 mM HEPES, pH 7.5, 0.05% BSA) at 37° C. for 2 hours. Activation of hGLP-1R was subsequently measured using the Cis Bio HTRF cAMP assay and compared to control peptides preincubated at 37° C. for 2 hours in the absence of DP-W. For polypeptides and their fragments/derivatives of this invention, "resistance to DP-IV" in this experiment is defined as a potency ratio of 0.1 up to 35, where "potency ratio" is the $EC_{50}$ of a peptide preincubated with DP-IV divided by the $EC_{50}$ of the same polypeptide of the invention preincubated without DP-IV. (FIG. 2)

Example 8

Measurement of Glucagon Receptor (GcgR) Signaling Using a Cyclic AMP Flashplate Assay CHO cells expressing the cloned human glucagon receptor (CHO-hGCGR) (Cascieri et al., J. Biol. Chem. (1999), 274, 8694-8697) were maintained in IMDM supplemented with 10% FBS, 1 mM L-glutamine, Penicillin-Streptomycin (100 U/ml), and G418 (500 µg/ml) cAMP levels in transfected cells upon incubation with peptides of this invention were determined with the aid of a Flashplate assay (SMP-004B, Perkin Elmer Life Sciences) following the manufacturer's instructions. The cell stimulation was stopped by addition of an equal amount of a detection buffer containing cell lysis agent and $^{125}$I-labeled cAMP tracer. The $^{125}$I-cAMP bound to the plate was determined using a liquid scintillation counter and used to quantitate the amount of cAMP present in each sample. For polypeptides and polypeptide fragments/derivatives of this invention, "activation" of the Gcg receptor in a cAMP Flashplate assay is induction of a maximal activity that is at least about 60% up to about 200% of the maximal activity induced by the native glucagon peptide with a relative potency of at least 0.04% up to about 10000%. "Relative potency" is the $EC_{50}$ of native glucagon ($EC_{50}$=70 pM) divided by the $EC_{50}$ of the polypeptide of the invention, multiplied by 100. "$EC_{50}$" is the concentration of a polypeptide at which 50% of the maximal activity is achieved. Native porcine OXM activated the glucagon receptor with an $EC_{50}$ of 2.4 nM in this assay.

Example 9

Effect on Blood Glucose Excursion During an Intraperitoneal Glucose Tolerance Test (IPGTT) in Lean Mice Male C57BL/6N mice were distributed by weight into treatment groups and fasted approximately 5 hours prior to the start of the study. Baseline (t=−30 min) blood glucose concentration was determined by glucometer from tail nick blood. Animals were then injected intraperitoneally (i.p.) with vehicle (saline) or a polypeptide of the invention (0.01-10 mg/kg). Blood glucose concentration was measured 30 minutes after treatment (t=0 min) and mice were then challenged i.p. with dextrose (2 g/kg, 10 mL/kg). One group of vehicle-treated mice was challenged with normal saline as a negative control. Blood glucose levels were determined from tail bleeds taken 20, 40, 60 and 120 min after dextrose challenge. The blood glucose excursion profile from t=0 to t=120 min was used to integrate an area under the curve (AUC) for each treatment. Percent inhibition of glucose excursion for each treatment group was calculated from the AUC data normalized to the water-challenged controls as per the formula:

$$\% \text{ inhibition} = \frac{AUC_{dex} - AUC_{peptide}}{AUC_{dex} - AUC_{saline}} \times 100,$$

where
$AUC_{dex}$=average AUC for vehicle-treated dextrose-challenged animals,
$AUC_{peptide}$=average AUC for peptide-treated dextrose-challenged animals, and
$AUC_{saline}$=average AUC for vehicle-treated saline-challenged animals.

Incretin activity of a polypeptide of the invention in IPGTT is manifested as a dose-dependent increase in percent inhibition of glucose excursion, reaching at least 30% at the 10 mg/kg dosage. (FIG. 2)

Example 10

Acute Effects on Food Intake and Body Weight in Lean Mice

Figure 3A:
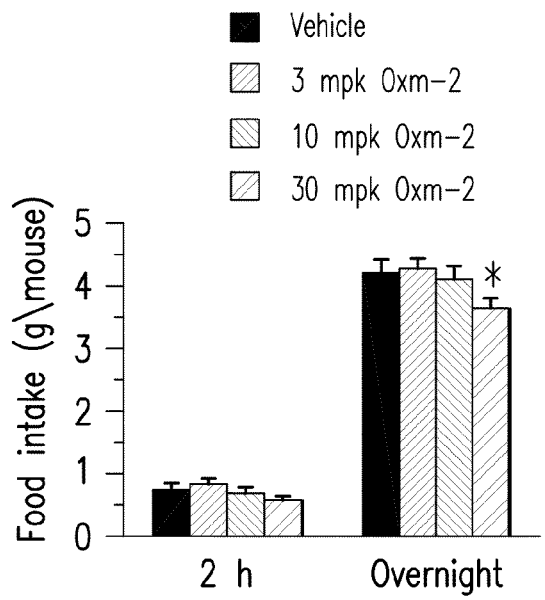
FIGS. 3A, 3B, and 3C illustrate the efficacy of the polypeptides denoted by sequences OXM2 and OXM3 in reducing overnight food intake and body weight gain in lean mice. * $p<0.05$ relative to the vehicle group.
Figure 3B:
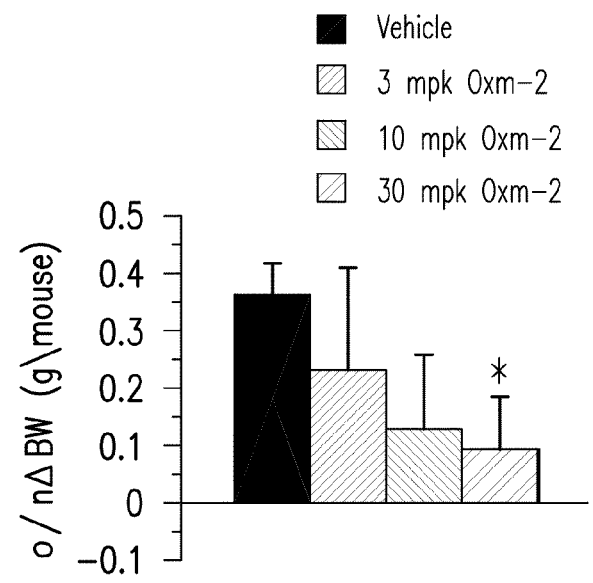
Figure 3C:
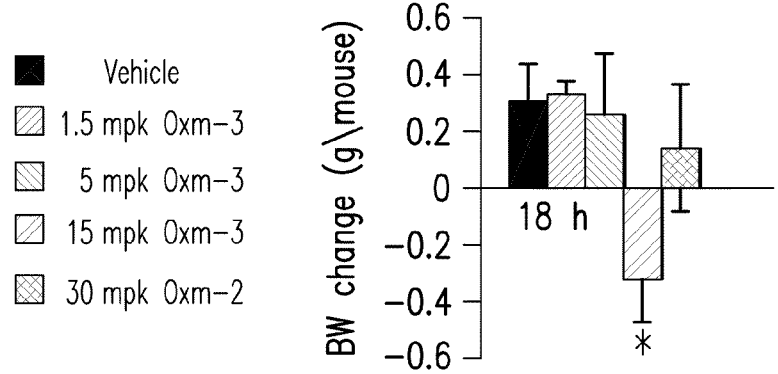

Approximately 3-month-old, ad libitum fed, male C57BL/6N mice were weighed and either vehicle (water) or OXM2 or OXM3 dissolved in vehicle was administered by i.p. injection ~30 min. prior to the onset of the dark phase of the light cycle. A pre-weighed aliquot of rodent chow (Teklad 7012) was provided in the food hopper of the wire cage top ~5 min. prior to the onset of the dark phase of the light cycle and weighed 2 and 18 hr (overnight) after the onset of the dark phase of the light cycle. Absolute changes in food intake were calculated for each animal by subtracting the amount of food remaining in the food hopper at the specified time points from that of the corresponding original pre-weighed aliquot. Absolute changes in body weight were calculated for each animal by subtracting the body weight of the animal prior to dosing from that of the corresponding animal at the specified time points. All values were reported as mean±SEM and peptide treatment groups were analyzed by the two-tailed unpaired Student's t test with reference to vehicle-treated animals. Reductions in food intake at any time point and/or in overnight body weight gain are considered to be statistically significant for P values $\leq 0.05$ and denotes efficacy of the corresponding OXM polypeptide (OXM2 or OXM3) in this model. (FIG. 3)

Example 11

Enhancement of Glucose-Stimulated Insulin Secretion in Mice

The in vitro potencies of native OXM in mediating insulin secretion at 16 mmol/l glucose were evaluated by measuring glucose-stimulated insulin secretion (GSIS) at 16 mmol/l glucose in the presence of increasing concentrations of the native OXM peptide in islets from wild type C57BL/6 mice and in MIN6c4 cells, a mouse insulinoma cell line with robust GSIS activity (Minami K, et al 2000 Am J Physiol Endocrinol Metab. 279:E773-E781). Pancreatic islets of Langerhans were isolated from the pancreas of normal C57BL/6J mice (Jackson Laboratory, Maine) by collagenase digestion and discontinuous Ficoll gradient separation, a modification of the original method of Lacy and Kostianovsky (Lacy et al., Diabetes 16:35-39, 1967). The islets were cultured overnight in RPMI 1640 medium (11 mM glucose) before GSIS assay. To measure GSIS, islets were first preincubated for 30 minutes in the Krebs-Ringer bicarbonate (KRB) buffer with 2 mM glucose (in Petri dishes). The KRB medium contains 143.5 mM Na⁺, 5.8 mM K⁺, 2.5 mM Ca²⁺, 1.2 mM Mg²⁺, 124.1 mM 1.2 mM PO₄³⁻, 1.2 mM SO₄²⁺, 25 mM CO₃²⁻, 2 mg/ml bovine serum albumin (pH 7.4). The islets were then transferred to a 96-well plate (one islet/well) and incubated at 37° C. for 60 minutes in 200 µl of KRB buffer with 2 or 16 mM glucose, along with other agents to be tested such as GLP-1 and OXM (Zhou et al., J. Biol. Chem. 278:51316-51323, 2003). Insulin was measured in aliquots of the incubation buffer by ELISA with a commercial kit (ALPCO Diagnostics, Windham, N.H.). The insulin secretion in the MIN6c4 cell was measured in cell seeded in 96-well plate in similar manner.

Figure 4A:
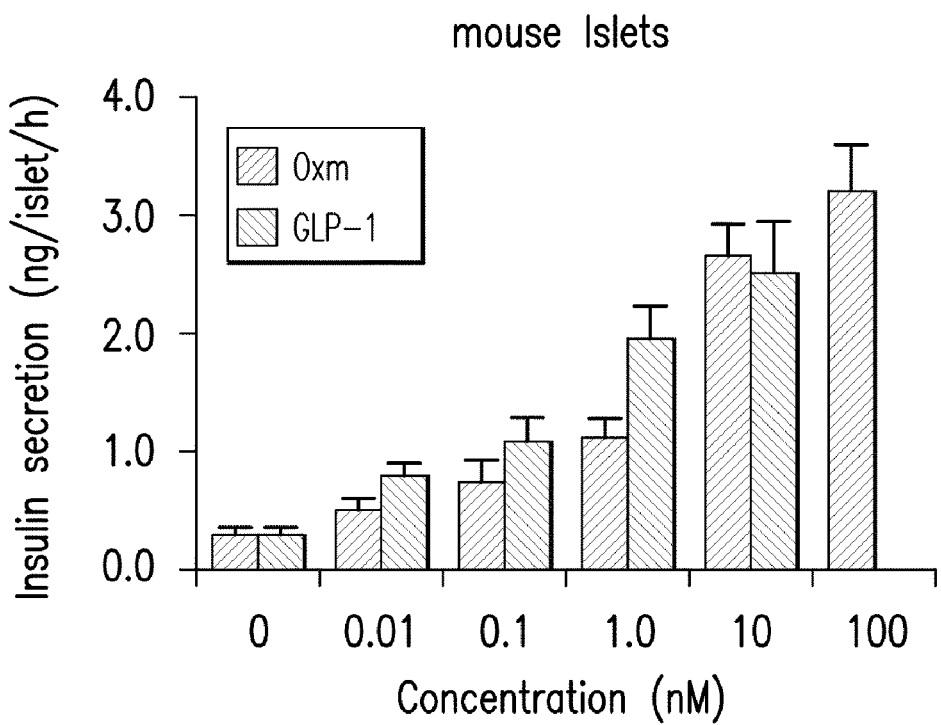
FIG. 4 depicts the effects of GLP-1 and OXM on glucose-stimulated insulin secretion (GSIS) in islets and MIN6 cells.
Figure 4B:
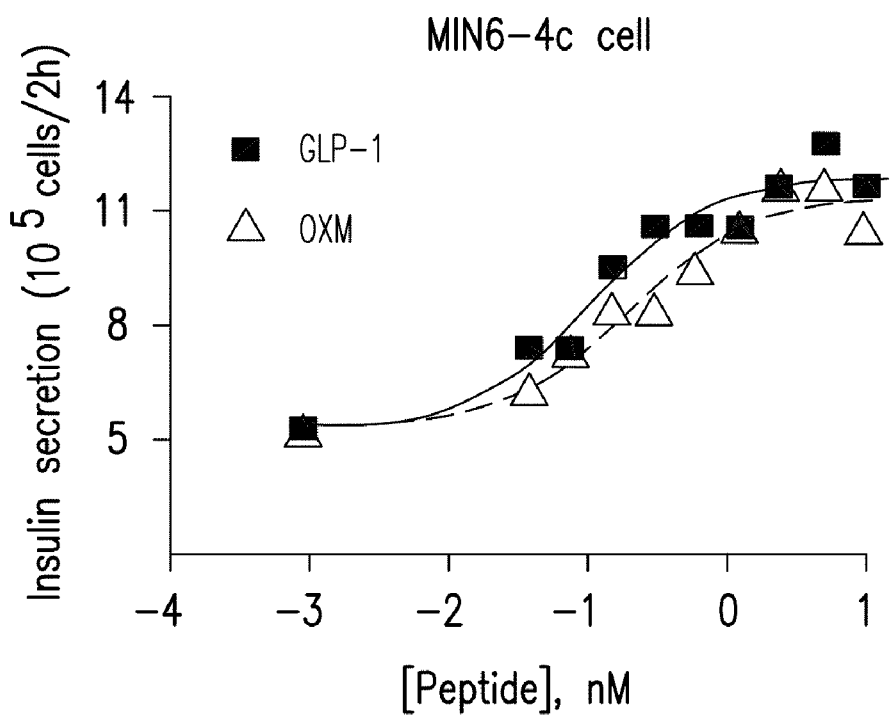

As shown in FIG. 4, the native OXM significantly enhanced GSIS in both mouse islets and the MIN6c4 cell. The EC50 of OXM on GSIS was about 2.9 nM in murine islets (FIG. 4A) and 155 pM respectively, FIG. 4B). Native GLP-1 was used as the positive control in this experiment. The maximal GSIS effects of the two peptides were similar in both islets and in MIN6 cells.

Figure 5A:
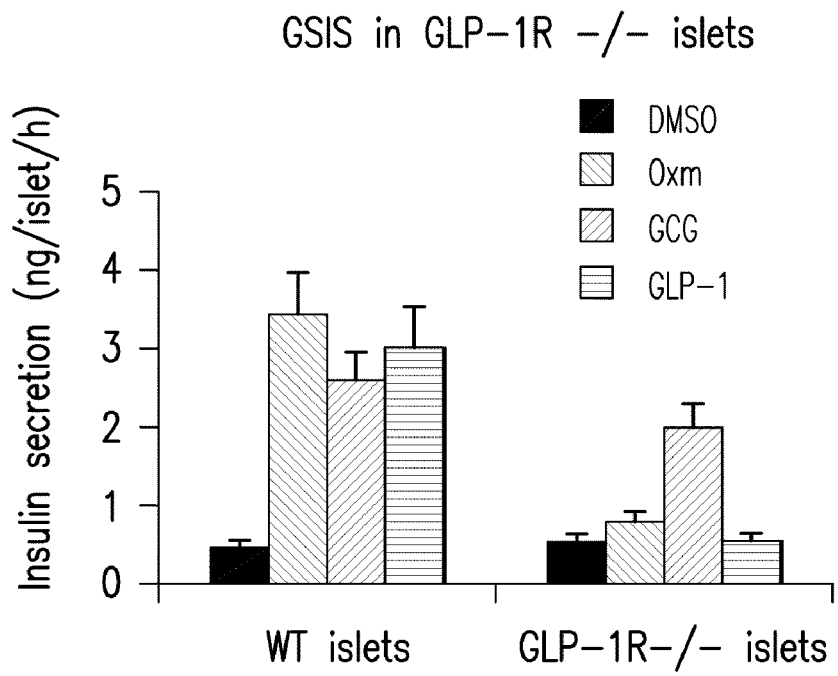
FIG. 5 shows the effects of GLP-1R deletion and receptor antagonism on OXM, GCG and GLP-1 mediated GSIS in islets.
Figure 5B:
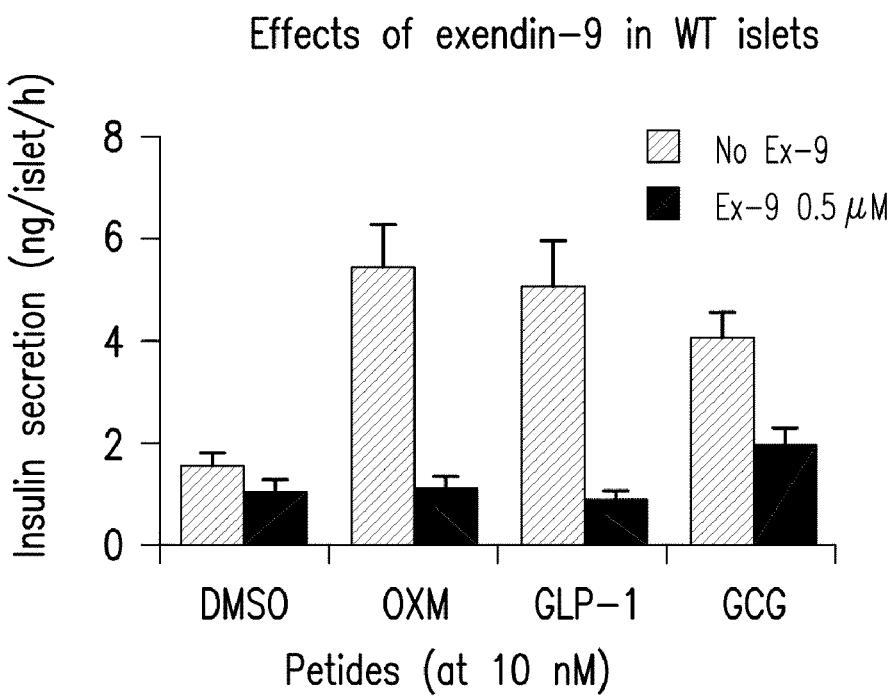

OXM activates both GLP-1R and GCG-R heterologously expressed in CHO cells as described in Example 7 and 8, and both receptors are known to be functional in pancreatic β-cells. To discern the potential roles of these two G-protein coupled receptors in the incretin action of OXM, the effects of OXM, GLP-1 and GCG on GSIS in islets from GLP-1R−/− mice (Scrocchi L A, et al. 1996 Nat Med 2:1254-1258) and age-matched WT C57BL/6 mice were examined. Consistent with previous results, all three peptides (10 nM each) were equally efficacious in augmenting GSIS at 16 mmol/l glucose from WT murine islets (FIG. 5A). GSIS and the potentiation of GSIS by GCG were not impaired in GLP-1R−/− islets, whereas both GLP-1 and OXM were completely unable to enhance GSIS in the latter. The involvement of GLP-1R in the incretin action of OXM was also indicated by antagonism of this activity by exendin-9, a widely-used peptide antagonist of GLP-1R. The potentiation of GSIS by OXM and GLP-1 was completely blocked in WT islets by 0.5 µM exendin-9 (FIG. 5B).

Figure 6A:
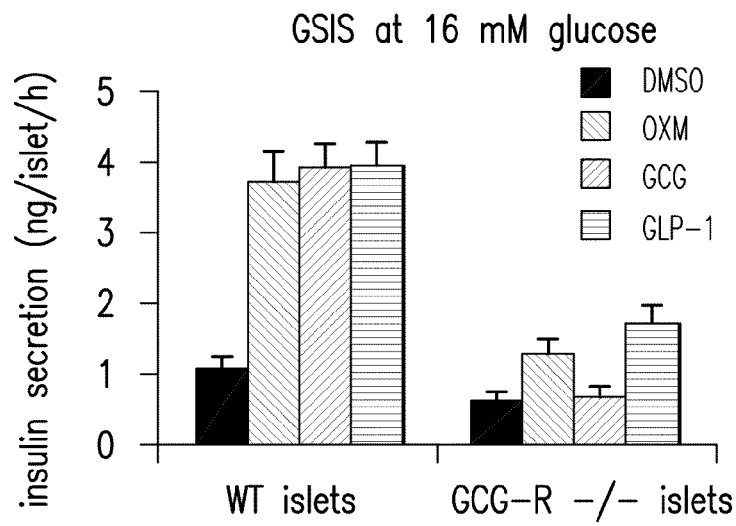
FIG. 6 illustrates the effect of OXM on GSIS in glucagon receptor −/− islets.
Figure 6B:
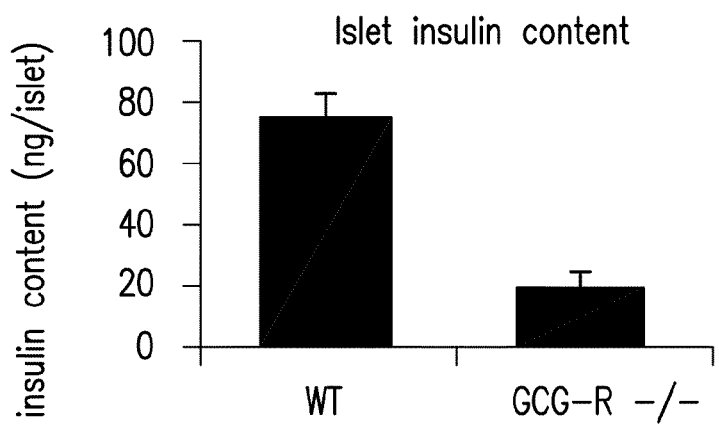
Figure 6C:
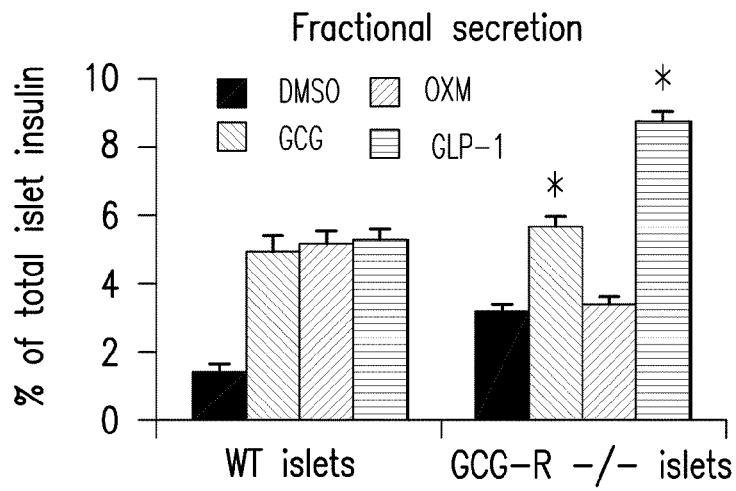

The potential participation of GCG-R in the incretin action of OXM was tested by comparing peptide-mediated GSIS at 16 mmol/l glucose in islets from WT and GCG-R−/− mice (Gelling, X Q, et al 2003; Proc. Natl. Acad. Sci. U.S.A. 100: 1438-1443). As described earlier, all three peptides (GLP-1, OXM and GCG, at 10 nM each) enhanced GSIS in WT islets with equal efficacy (FIG. 6A). Compared to size-matched WT islets however, insulin secretion at both 2 and 16 mM glucose was reduced by ~2-fold in GCG-R−/− islets (FIG. 6A). Islet insulin content was also reduced in GCG-R −/− islets by >3-fold relative to WT (FIG. 6B). GCG (10 nM) did not enhance GSIS at 16 mM glucose in GCG-R−/− islets whereas both GLP-1 and OXM (10 nM) significantly increased GSIS in this assay. When data were expressed as fractional GSIS (% insulin released relative to total islet insulin content), the fold-increase in GSIS mediated by OXM was reduced by only 32% (1.7 vs 2.5 fold) in GCG-R−/− islets relative to WT (FIG. 6C), whereas the fold-stimulation of GSIS by GLP-1 remained the same (2.5 fold). In contrast, GCG did not increase fractional GSIS over baseline (DMSO) in GCG-R−/− islets. These data suggest that GCG-R may play limited role in the action of OXM on GSIS.

Figure 7A:
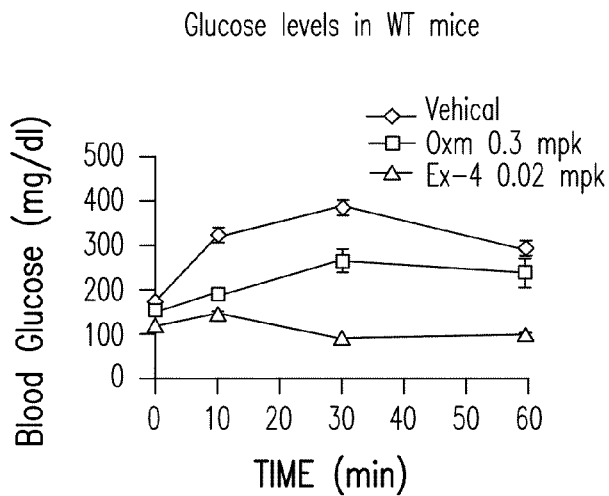
FIG. 7 shows the effects of OXM and exendin-4 on blood glucose and insulin levels during IPGTT in wild-type and GLP-1R−/− mice.
Figure 7C:
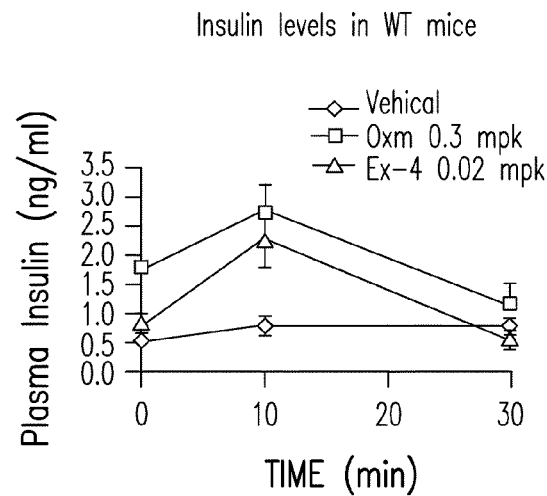
Figure 7B:
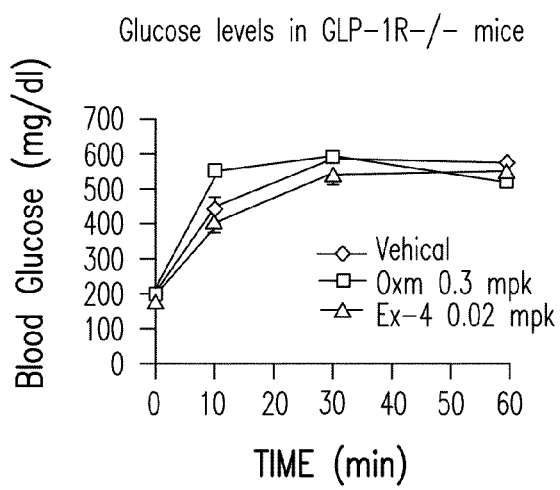

To determine whether the glucose-lowering effect of OXM (as described supra and as shown in FIG. 2) was secondary to increased in vivo GSIS the effects of OXM on plasma glucose and insulin levels during an IPGTT in WT and GLP-1R−/− mice was analyzed. Mice fasted overnight were pre-dosed with 0.3 mpk (mg peptide per kg of body weight) of native OXM (i.p.) prior to glucose challenge. The GLP-1 mimetic exendin-4 (dosed at 0.02 mpk i.p.) (Thorens, B, et al. 1993; Diabetes. 42: 1678-1682) was used as a comparator in this study. As shown in FIG. 7A, both exendin-4 and OXM significantly reduced glucose levels during an IPGTT in WT mice, with exendin-4 being more potent in suppressing glucose excursion. The area under the curve (AUC) for glucose excursion in the 0.3 mpk OXM treated group was reduced by approximately 30% relative to the vehicle group [13025 f 524 versus 19928±811 mg/dl/60 min], p<0.001, n=10 (vehicle) or 5 (OXM)], whereas reduction of glucose AUC in the exendin-4 treated group was >60% (AUC=6601±179 mg/dl/60 min). In contrast, the same doses of OXM and exendin-4 did not affect glucose excursion in an IPGTT in GLP-1R−/− mice (FIG. 7B).

Figure 7D:
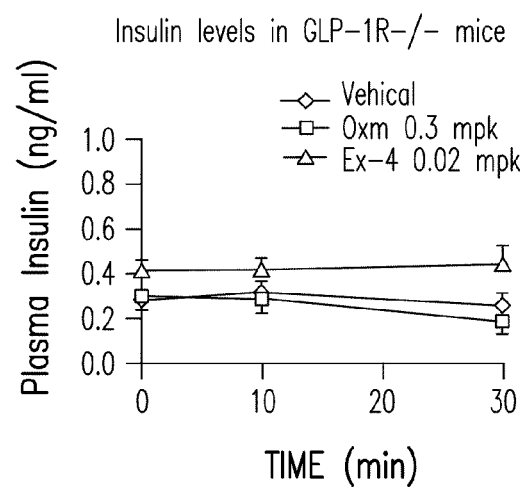
Figure 8A:
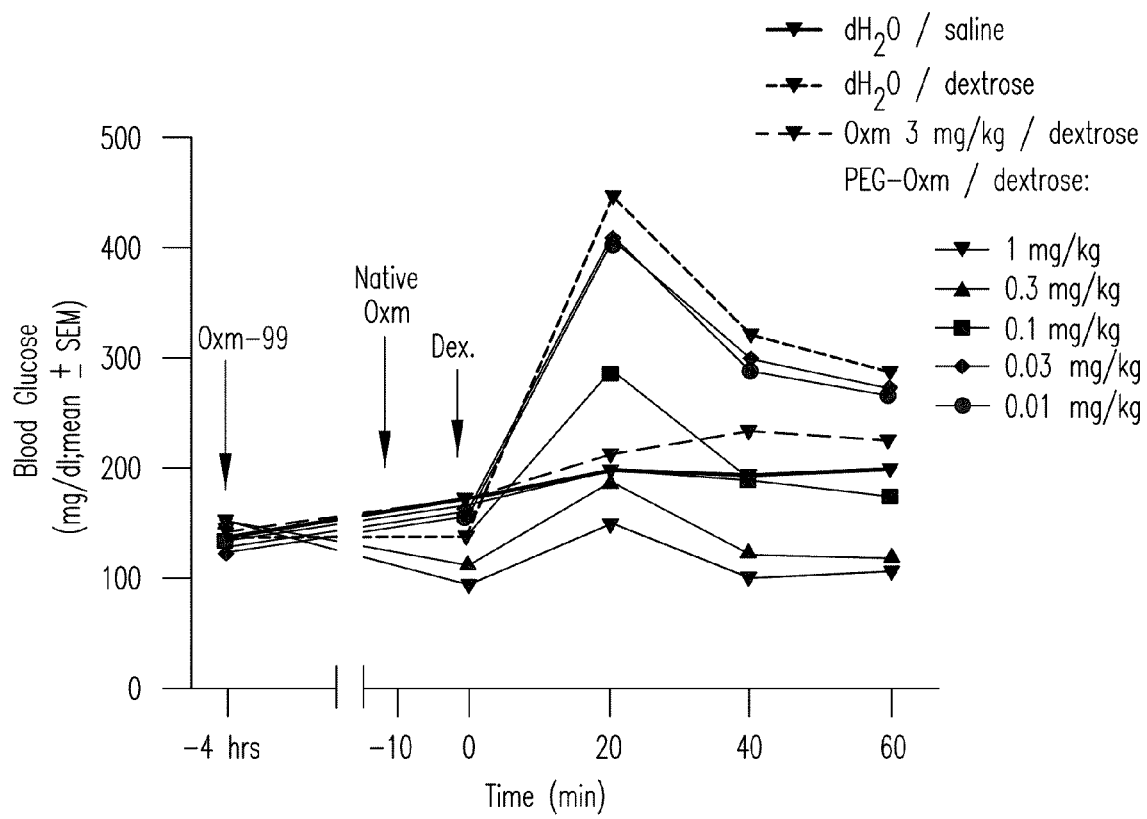
FIG. 8 shows the acute glucose-lowering effects of OXM99 in the lean mouse IPGTT.
Figure 8B:
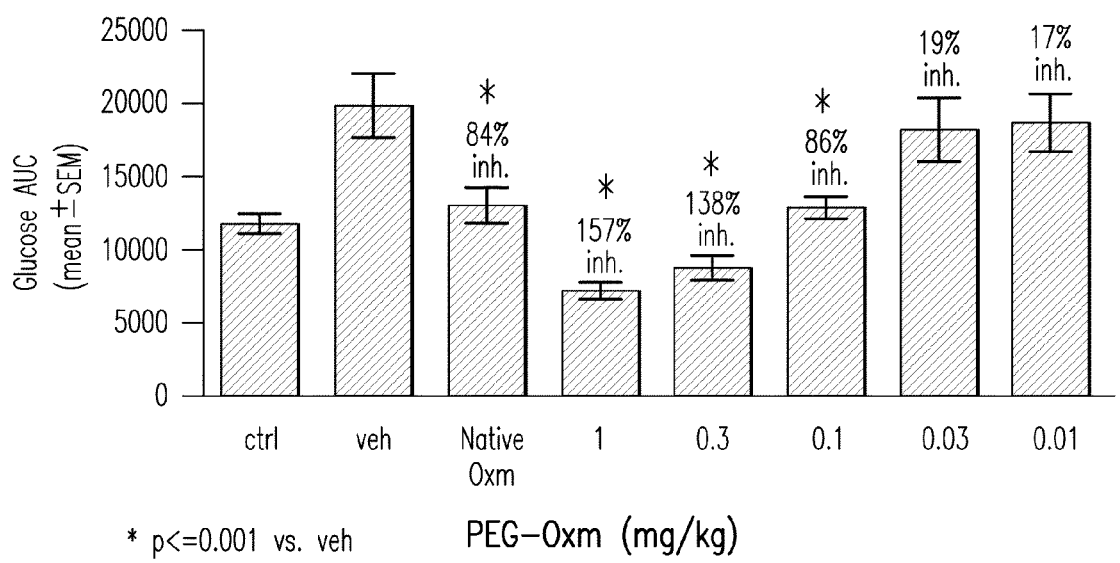
Figure 9:
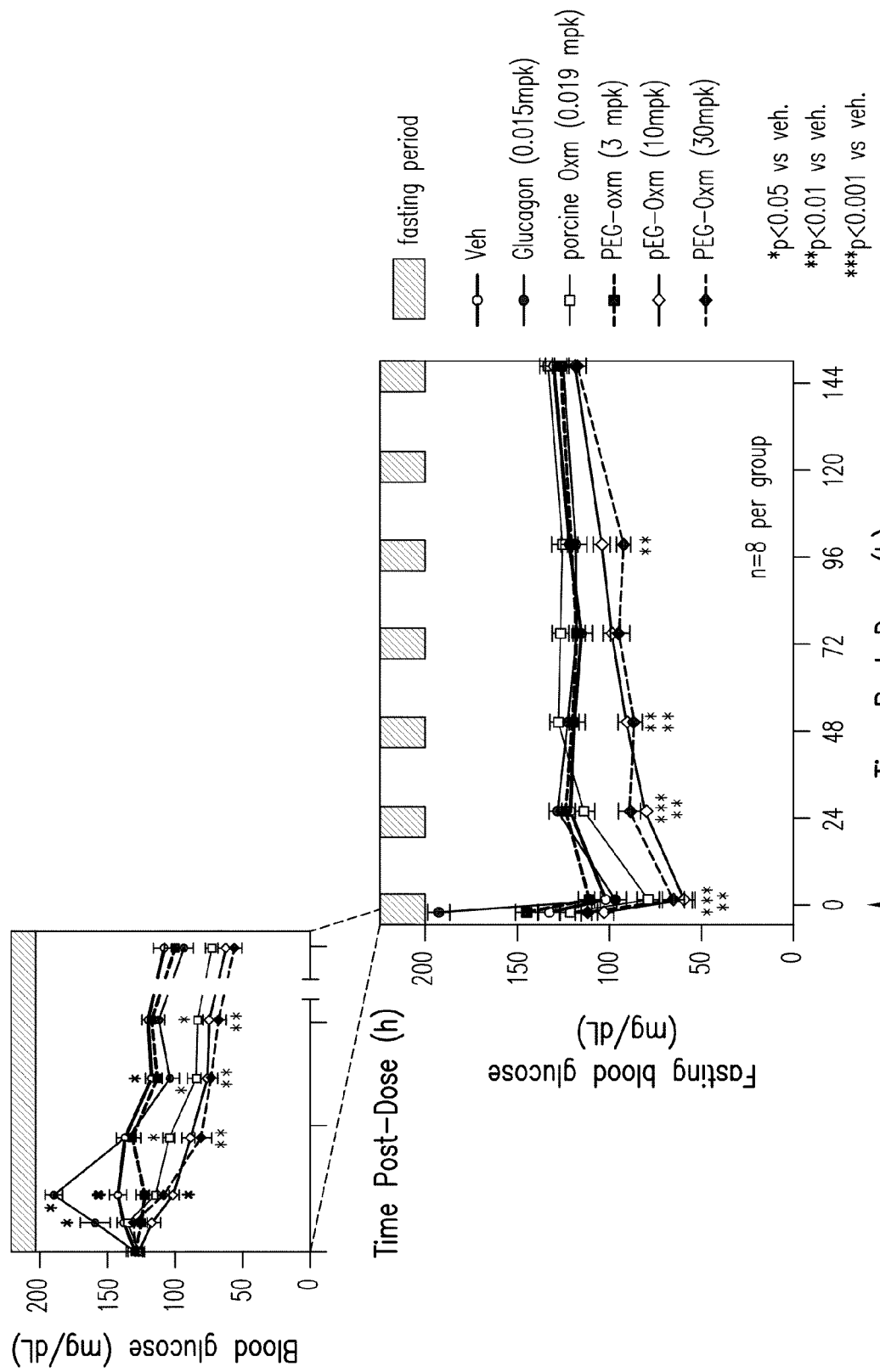
FIG. 9 depicts the effect of OXM99 in reducing blood glucose in lean mice.
Figure 10:
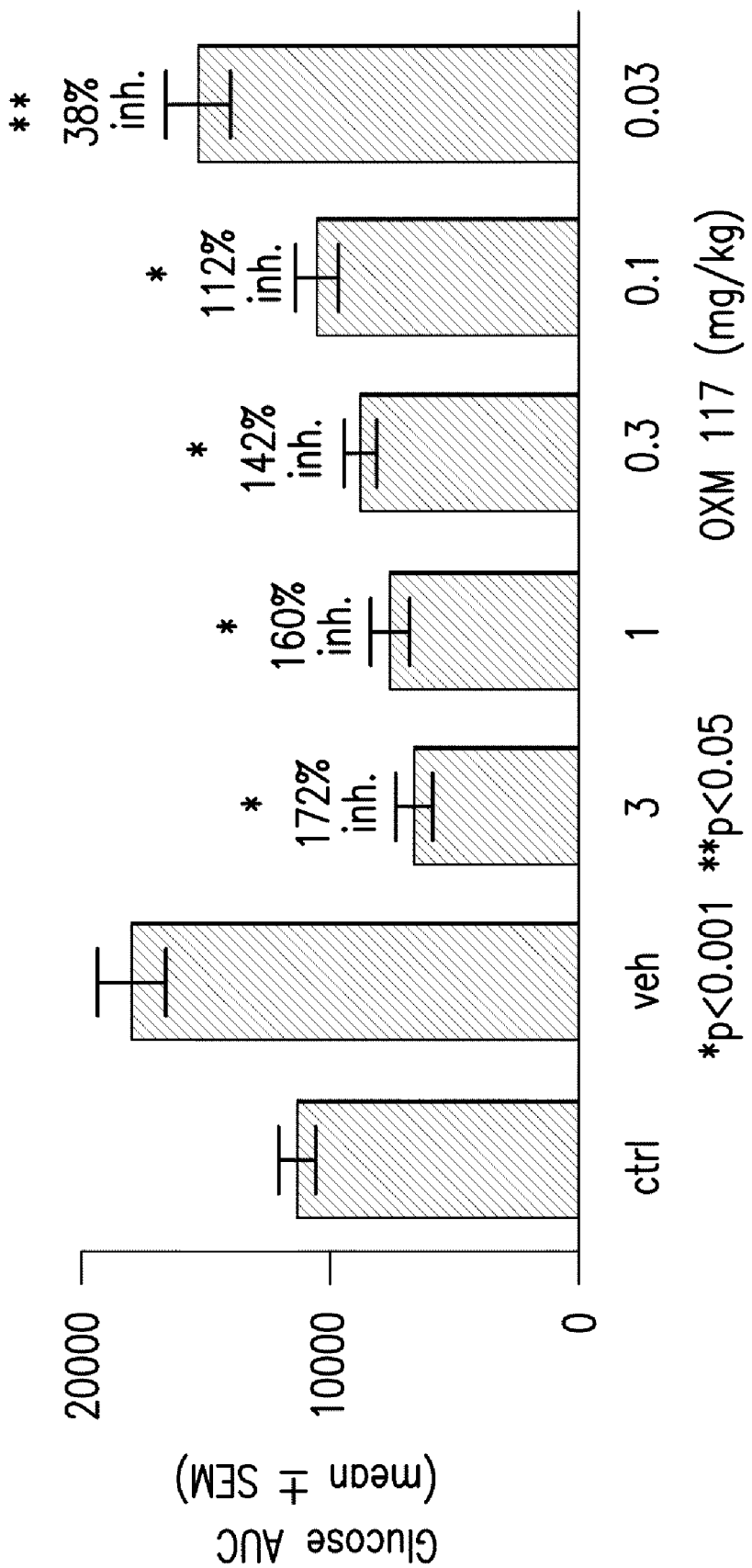
FIG. 10 illustrates the glucose-lowering effects of OXM117 in the lean mouse IPGTT.
Figure 11:
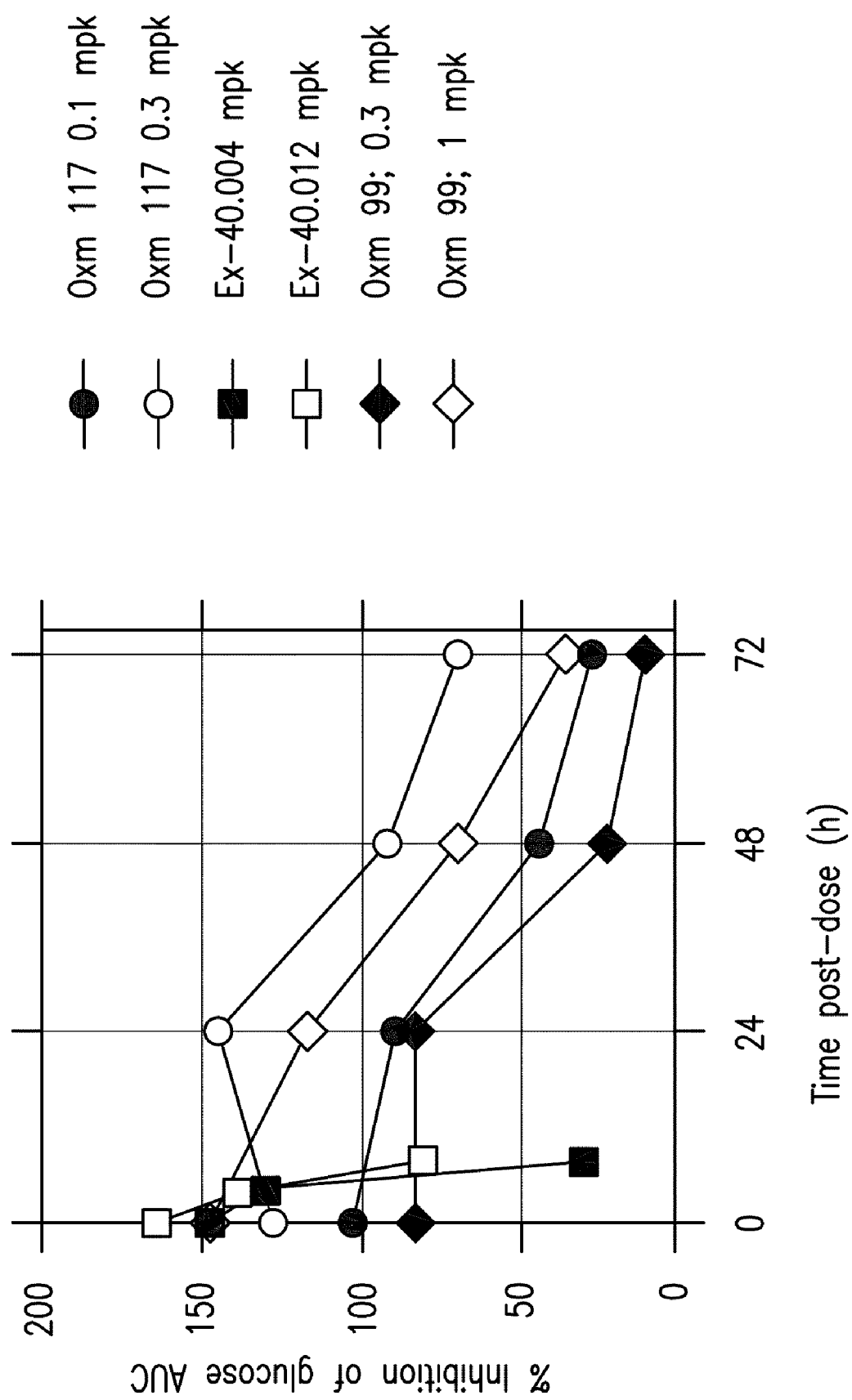
FIG. 11 shows the duration of action of the OXM analogs OXM117 and OXM99 compared with exendin-4.
Figure 12B:
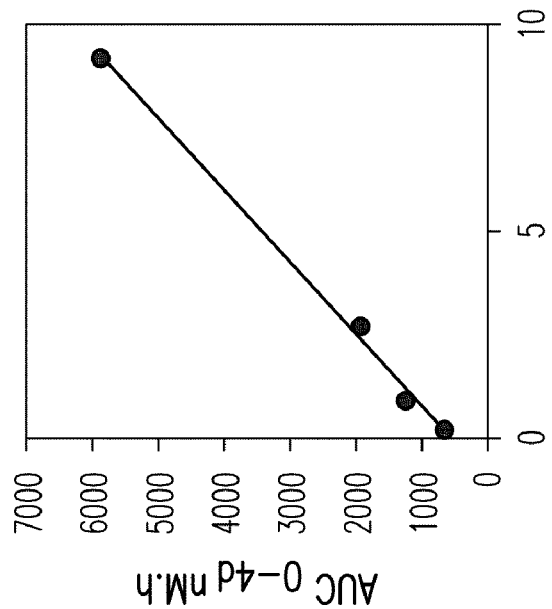
FIG. 12 depicts the pharmacokinetics for OXM117 using subcutaneous dosing in the rat.
Figure 12A:
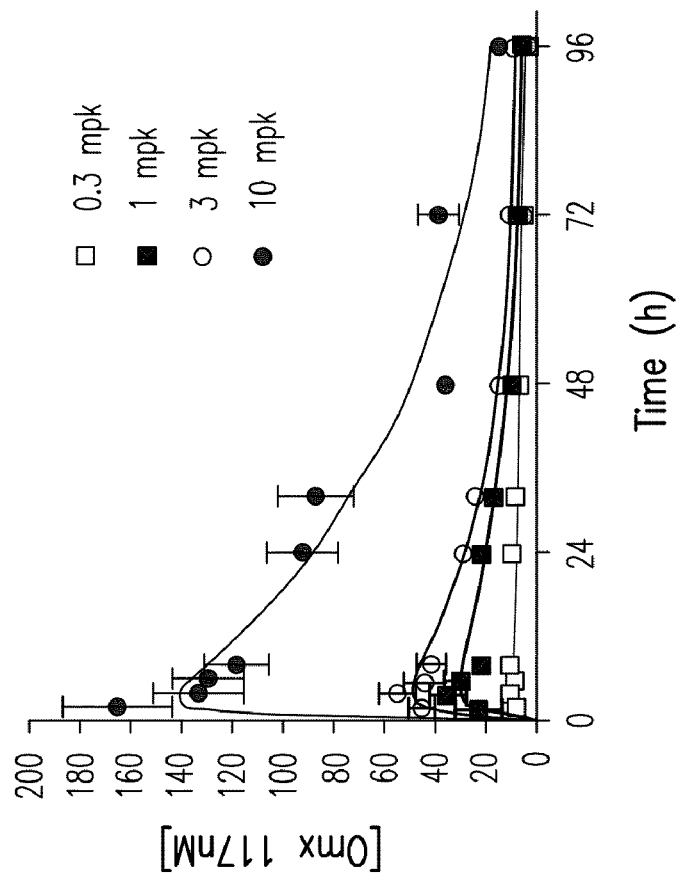
Figure 13A:
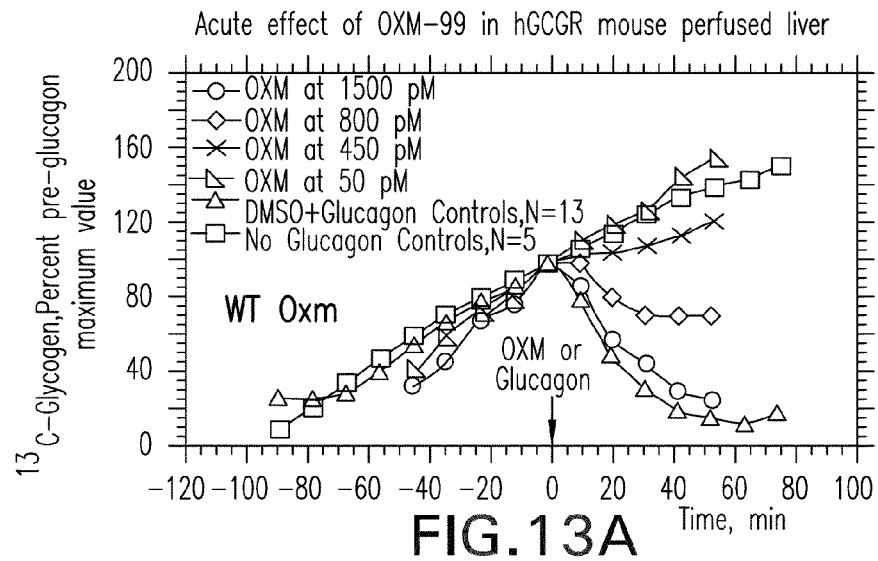
FIG. 13 shows the results of studies demonstrating that the OXM117 peptide shows no glucagon-like activity in vitro.
Figure 13B:
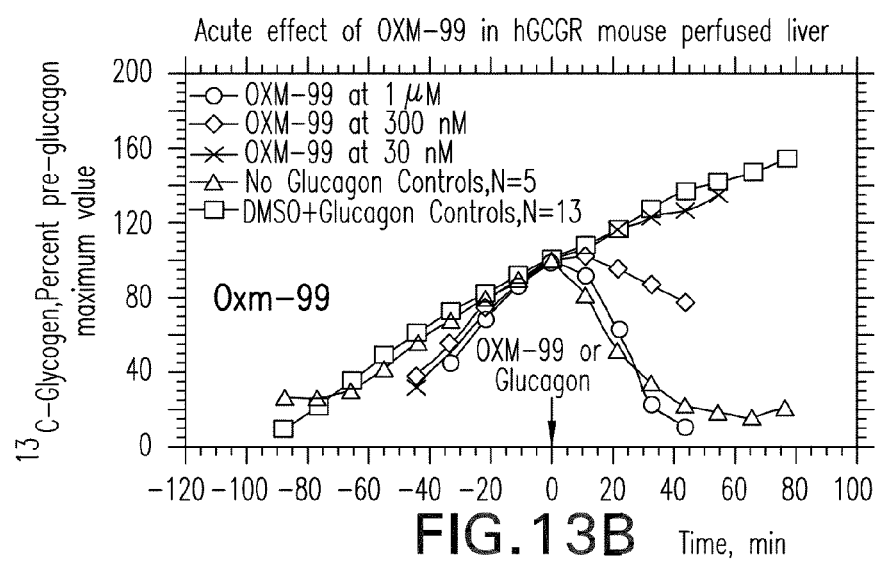
Figure 13C:
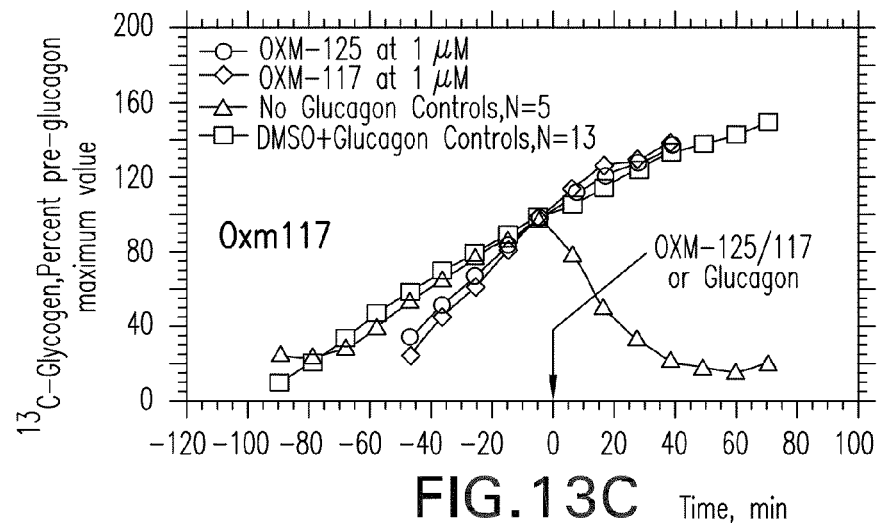

The effects of i.p. OXM and exendin-4 on in vivo GSIS were assessed by measuring plasma insulin levels before (at 0 min) and after (at 10 min) glucose challenge in the IPGTT studies. OXM increased basal (0 min) plasma insulin levels 4-fold in WT mice and significantly amplified the insulin response to i.p. glucose challenge (FIG. 7C). Similar effects were observed with exendin-4 in WT mice. In contrast, administration of OXM or exendin-4 to the GLP-1R−/− mice did not affect basal insulin levels, nor did it improve the insulin response to i.p. glucose challenge (FIG. 7D).

EXAMPLES OF PHARMACEUTICAL COMPOSITIONS

As a specific embodiment of an oral composition of a novel polypeptide of the present invention, 5 ma of a polypeptide as described by the formula

is formulated with sufficient finely divided lactose to provide a total amount of 580 to 590 mg to fill a size 0 hard gel capsule.

As another specific embodiment of an oral composition of a novel polypeptide of the present invention, 2.5 mg of a polypeptide as described by the formula

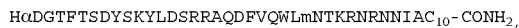

is formulated with sufficient finely divided lactose to provide a total amount of 580 to 590 mg to fill a size 0 hard gel capsule.

Other embodiments are within the following claims. While several embodiments have been shown and described, various modifications may be made without departing from the spirit and scope of the present invention.

What is claimed is:

1. A polypeptide comprising the amino acid sequence of SEQ ID NO:4, further comprising a substitution of Asp, Glu, Ile, Val, D-Ser, Met, D-Ala, Trp, Asn, Leu, or α-aminoisobutyric acid for the Ser at position 2 and a pharmaceutically acceptable salt thereof.

2. The polypeptide of claim 1, wherein the polypeptide further comprises one or more amino acid substitutions selected from
   (a) Asp, Glu, Pro, Leu or L-norleucine for the Gln at position 3;
   (b) Ala, Cys, Cys(mPEG), or Cys(cholesteryl) for the Ser at position 11;

(c) Cys, Cys(mPEG), or Cys(cholesteryl) for the Lys at position 12;
(d) Ala for the Ser at position 16;
(e) Cys, Cys(mPEG), or Cys(cholesteryl) for the Arg at position 17;
(f) Cys, Cys(mPEG), or Cys(cholesteryl) for the Arg at position 18;
(g) Cys, Cys(mPEG), or Cys(cholesteryl) for the Gln at position 20;
(h) Cys, Cys(mPEG), or Cys(cholesteryl) for the Asp at position 21;
(i) Cys, Cys(mPEG), or Cys(cholesteryl) for the Gln at position 24;
(j) Met(O), Val, norleucine, alanine, α-aminoisobutyric acid or O-methyl-homoserine for the Met at position 27;
(k) Cys, Cys(mPEG), or Cys(cholesteryl) for the Asn at position 28;
(l) Cys, Cys(mPEG), or Cys(cholesteryl) for the Thr at position 29;
(m) Cys, Cys(mPEG), or Cys(cholesteryl) for the Ile at position 36; or
(n) Cys, Cys(mPEG), or Cys(cholesteryl) for the Ala at position 37.

3. The polypeptide of claim 1, wherein the polypeptide further comprises a deletion of amino acids 31-37.

4. The polypeptide of claim 1, wherein the polypeptide further comprises a Lys(Palmitoyl), Cys, Cys(mPEG), or Cys(cholesteryl) at the carboxy terminus.

5. The polypeptide of claim 1, wherein the polypeptide comprises α-aminoisobutyric acid for the Ser at position 2, Asp for the Gln at position 3, Met(O) for the Met at position 27, and a Cys(mPEG) at the carboxy terminus.

6. The polypeptide of claim 1, wherein the polypeptide comprises α-aminoisobutyric acid for the Ser at position 2, Asp for the Gln at position 3, Met(O) for the Met at position 27, and a Cys(cholesteryl) at the carboxy terminus.

7. The polypeptide of claim 1, wherein the polypeptide comprises D-Ser for the Ser at position 2 and a Lys(palmitoyl) at the carboxy terminus.

8. The polypeptide of claim 1, wherein the polypeptide is selected from a polypeptide comprising the amino acid sequence of SEQ ID NO:114, SEQ ID NO:120, or SEQ ID NO:121.

9. A pharmaceutical composition comprising the polypeptide of claim 1 and a pharmaceutically suitable carrier.

10. A method for reducing body weight in a subject in need thereof comprising the step of administering to the subject a polypeptide comprising the amino acid sequence of SEQ ID NO:4, further comprising a substitution of Asp, Glu, Ile, Val, D-Ser, Met, D-Ala, Trp, Asn, Leu, or α-aminoisobutyric acid for the Ser at position 2 and a pharmaceutically acceptable salt thereof.

11. The method of claim 10, wherein the polypeptide further comprises one or more amino acid substitutions selected from
(a) Asp, Glu, Pro, Leu or L-norleucine for the Gln at position 3;
(b) Ala, Cys, Cys(mPEG), or Cys(cholesteryl) for the Ser at position 11;
(c) Cys, Cys(mPEG), or Cys(cholesteryl) for the Lys at position 12;
(d) Ala for the Ser at position 16;
(e) Cys, Cys(mPEG), or Cys(cholesteryl) for the Arg at position 17;
(f) Cys, Cys(mPEG), or Cys(cholesteryl) for the Arg at position 18;
(g) Cys, Cys(mPEG), or Cys(cholesteryl) for the Gln at position 20;
(h) Cys, Cys(mPEG), or Cys(cholesteryl) for the Asp at position 21;
(i) Cys, Cys(mPEG), or Cys(cholesteryl) for the Gln at position 24;
(j) Met(O), Val, norleucine, alanine, α-aminoisobutyric acid or O-methyl-homoserine for the Met at position 27;
(k) Cys, Cys(mPEG), or Cys(cholesteryl) for the Asn at position 28;
(l) Cys, Cys(mPEG), or Cys(cholesteryl) for the Thr at position 29;
(m) Cys, Cys(mPEG), or Cys(cholesteryl) for the Ile at position 36; or
(n) Cys, Cys(mPEG), or Cys(cholesteryl) for the Ala at position 37.

12. The method of claim 10, wherein the polypeptide further comprises a deletion of amino acids 31-37.

13. The method of claim 10, wherein the polypeptide further comprises a Lys(Palmitoyl), Cys, Cys(mPEG), or Cys(cholesteryl) at the carboxy terminus.

14. The method of claim 10, wherein the polypeptide comprises α-aminoisobutyric acid for the Ser at position 2, Asp for the Gln at position 3, Met(O) for the Met at position 27, and a Cys(mPEG) at the carboxy terminus.

15. The method of claim 10, wherein the polypeptide comprises α-aminoisobutyric acid for the Ser at position 2, Asp for the Gln at position 3, Met(O) for the Met at position 27, and a Cys(cholesteryl) at the carboxy terminus.

16. The method of claim 10, wherein the polypeptide comprises D-Ser for the Ser at position 2 and a Lys(palmitoyl) at the carboxy terminus.

17. The method of claim 10, wherein the polypeptide is selected from a polypeptide comprising the amino acid sequence of SEQ ID NO:114, SEQ ID NO:120, or SEQ ID NO:121.

18. The method of claim 10, wherein the treatment lowers glucose levels in the subject.

* * * * *

SEQUENCE LISTING

<160> NUMBER OF SEQ ID NOS: 168

<210> SEQ ID NO 1
<211> LENGTH: 38

```
<212> TYPE: PRT
<213> ORGANISM: Artificial Sequence
<220> FEATURE:
<223> OTHER INFORMATION: Synthetic peptide based on the human
      oxyntomodulin sequence

<400> SEQUENCE: 1

His Gly Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Ala
        35

<210> SEQ ID NO 2
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (38)..(38)
<223> OTHER INFORMATION: X=Cysteine PEGylated via side chain thiol to
      linear methoxy PEG 20kDa

<400> SEQUENCE: 2

His Gly Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 3
<211> LENGTH: 38
<212> TYPE: PRT
<213> ORGANISM: Artificial Sequence
<220> FEATURE:
<223> OTHER INFORMATION: Synthesized oxyntomodulin polypeptide
<220> FEATURE:
<221> NAME/KEY: MOD_RES
<222> LOCATION: (38)..(38)
<223> OTHER INFORMATION: X= Cysteine  PEGylated via the side-chain
      thiol with branched methoxyPEG
<220> FEATURE:
<221> NAME/KEY: MOD_RES
<222> LOCATION: (38)..(38)
<223> OTHER INFORMATION: X= Cysteine  PEGylated via the side-chain
      thiol with branched methoxy PEG 40kDa

<400> SEQUENCE: 3

His Gly Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 4
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
```

<221> NAME/KEY: MOD_RES
<222> LOCATION: (37)..(37)
<223> OTHER INFORMATION: AMIDATION

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 5
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (37)..(37)
<223> OTHER INFORMATION: AMIDATION

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 6
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: ACETYLATION

<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 7
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib

<400> SEQUENCE: 7

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 8
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence

<400> SEQUENCE: 8

His Val Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 9
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: Xaa=D-alanine

<400> SEQUENCE: 9

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 10
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=D-serine

<400> SEQUENCE: 10

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

```
<210> SEQ ID NO 11
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence

<400> SEQUENCE: 11

His Ser Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 12
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence

<400> SEQUENCE: 12

His Ser Asp Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 13
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence

<400> SEQUENCE: 13

His Ser Leu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 14
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (3)..(3)
<223> OTHER INFORMATION: X= Norleucine

<400> SEQUENCE: 14

His Ser Xaa Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30
```

Arg Asn Asn Ile Ala
        35

<210> SEQ ID NO 15
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence

<400> SEQUENCE: 15

His Gly Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 16
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence

<400> SEQUENCE: 16

Phe Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 17
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MUTAGEN
<222> LOCATION: (1)..(1)
<223> OTHER INFORMATION: Pyr-His
<220> FEATURE:
<221> NAME/KEY: MOD_RES
<222> LOCATION: (37)..(37)
<223> OTHER INFORMATION: AMIDATION

<400> SEQUENCE: 17

Xaa Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 18
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence -continued

```
<400> SEQUENCE: 18

His Ser Pro Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 19
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MUTAGEN
<222> LOCATION: (1)..(1)
<223> OTHER INFORMATION: X=Imidazole-lactic acid histidine
<220> FEATURE:
<221> NAME/KEY: MOD_RES
<222> LOCATION: (37)..(37)
<223> OTHER INFORMATION: AMIDATION

<400> SEQUENCE: 19

Xaa Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 20
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MUTAGEN
<222> LOCATION: (1)..(1)
<223> OTHER INFORMATION: X=N-methyl-Histidine
<220> FEATURE:
<221> NAME/KEY: MOD_RES
<222> LOCATION: (37)..(37)
<223> OTHER INFORMATION: AMIDATION

<400> SEQUENCE: 20

Xaa Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 21
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MUTAGEN
<222> LOCATION: (1)..(1)
<223> OTHER INFORMATION: X=desamino-histidine
<220> FEATURE:
```

```
<221> NAME/KEY: MOD_RES
<222> LOCATION: (37)..(37)
<223> OTHER INFORMATION: AMIDATION

<400> SEQUENCE: 21

Xaa Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 22
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MUTAGEN
<222> LOCATION: (1)..(1)
<223> OTHER INFORMATION: X= N,N-dimethyl-histidine
<220> FEATURE:
<221> NAME/KEY: MOD_RES
<222> LOCATION: (37)..(37)
<223> OTHER INFORMATION: AMIDATION

<400> SEQUENCE: 22

Xaa Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 23
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MUTAGEN
<222> LOCATION: (1)..(1)
<223> OTHER INFORMATION: X= benzoyl-histidine
<220> FEATURE:
<221> NAME/KEY: MOD_RES
<222> LOCATION: (37)..(37)
<223> OTHER INFORMATION: AMIDATION

<400> SEQUENCE: 23

Xaa Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 24
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
```

```
<221> NAME/KEY: MUTAGEN
<222> LOCATION: (1)..(1)
<223> OTHER INFORMATION: X=Benzyl-histidine
<220> FEATURE:
<221> NAME/KEY: MOD_RES
<222> LOCATION: (37)..(37)
<223> OTHER INFORMATION: AMIDATION

<400> SEQUENCE: 24

Xaa Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 25
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 25

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Met Asn Thr Lys Arg Asn
            20                  25                  30

Arg Asn Asn Ile Ala
        35

<210> SEQ ID NO 26
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 26

His Ser Gln Gly Thr Phe Thr Ser Asp Tyr Ala Lys Tyr Leu Asp Ala
 1               5                  10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 27
<211> LENGTH: 36
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (36)..(36)
<223> OTHER INFORMATION: AMIDATION
```

```
<400> SEQUENCE: 27

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile
        35

<210> SEQ ID NO 28
<211> LENGTH: 35
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (35)..(35)
<223> OTHER INFORMATION: AMIDATION

<400> SEQUENCE: 28

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn
        35

<210> SEQ ID NO 29
<211> LENGTH: 34
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (34)..(34)
<223> OTHER INFORMATION: AMIDATION

<400> SEQUENCE: 29

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn

<210> SEQ ID NO 30
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib

<400> SEQUENCE: 30

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
```

<210> SEQ ID NO 31
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (38)..(38)
<223> OTHER INFORMATION: AMIDATION

<400> SEQUENCE: 31

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 32
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (37)..(37)
<223> OTHER INFORMATION: AMIDATION

<400> SEQUENCE: 32

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Cys Thr Lys Arg Asn
            20                  25                  30

Arg Asn Asn Ile Ala
        35

<210> SEQ ID NO 33
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (27)..(27)
<223> OTHER INFORMATION: X=Methionine sulfoxide

<400> SEQUENCE: 33

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala
        35

<210> SEQ ID NO 34
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (37)..(37)
<223> OTHER INFORMATION: AMIDATION

<400> SEQUENCE: 34

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 35
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: AMIDATION

<400> SEQUENCE: 35

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 36
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-serine
<220> FEATURE:
<221> NAME/KEY: MOD_RES
<222> LOCATION: (38)..(38)
<223> OTHER INFORMATION: X= Cysteine residue  PEGylated via side-
      chain thiol with linear methoxyPEG 5 kDa
<220> FEATURE:

```
<221> NAME/KEY: MOD_RES
<222> LOCATION: (38)..(38)
<223> OTHER INFORMATION: AMIDATION

<400> SEQUENCE: 36

His Xaa Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
             20                  25                  30

Arg Asn Asn Ile Ala Xaa
         35

<210> SEQ ID NO 37
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= cysteine residue PEGylated via side-chain
      thiol with linear methoxyPEG 20 kDa
<220> FEATURE:
<221> NAME/KEY: MOD_RES
<222> LOCATION: (38)..(38)
<223> OTHER INFORMATION: AMIDATION

<400> SEQUENCE: 37

His Xaa Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
             20                  25                  30

Arg Asn Asn Ile Ala Xaa
         35

<210> SEQ ID NO 38
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= Cysteine residue PEGylated via the side-
      chain thiol with branched methoxyPEG 40kDa
<220> FEATURE:
<221> NAME/KEY: MOD_RES
<222> LOCATION: (38)..(38)
<223> OTHER INFORMATION: AMIDATION

<400> SEQUENCE: 38

His Xaa Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
             20                  25                  30

Arg Asn Asn Ile Ala Xaa
         35
```

```
<210> SEQ ID NO 39
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= Cysteine residue linked to cholesterol
      via the side-chain thiol
<220> FEATURE:
<221> NAME/KEY: MOD_RES
<222> LOCATION: (38)..(38)
<223> OTHER INFORMATION: AMIDATION

<400> SEQUENCE: 39

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 40
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 40

His Ala Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 41
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 41

His Arg Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
```

<210> SEQ ID NO 42
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 42

His Asn Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 43
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 43

His Asp Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 44
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 44

His Glu Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 45
<211> LENGTH: 37
<212> TYPE: PRT
<213> ORGANISM: Artificial Sequence
<220> FEATURE:

<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 45

His Gln Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 46
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 46

His His Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 47
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 47

His Ile Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 48
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 48

His Leu Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 49
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 49

His Lys Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 50
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 50

His Met Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 51
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 51

His Phe Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala

<210> SEQ ID NO 52
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 52

His Pro Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 53
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 53

His Thr Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 54
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 54

His Trp Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
            35

<210> SEQ ID NO 55
<211> LENGTH: 37
<212> TYPE: PRT
<213> ORGANISM: Artificial Sequence
<220> FEATURE:

<223> OTHER INFORMATION: Synthetic peptide based on the human
      oxyntomodulin sequence
<220> FEATURE:
<221> NAME/KEY: MOD_RES
<222> LOCATION: (37)..(37)
<223> OTHER INFORMATION: AMIDATION

<400> SEQUENCE: 55

His Tyr Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 56
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (37)..(37)
<223> OTHER INFORMATION: AMIDATION

<400> SEQUENCE: 56

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 57
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=D-Serine
<220> FEATURE:
<221> NAME/KEY: MOD_RES
<222> LOCATION: (38)..(38)
<223> OTHER INFORMATION: X= cysteine residue in which the side-chain
      thiol is reacted with iodoacetamide

<400> SEQUENCE: 57

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 58
<211> LENGTH: 37
<212> TYPE: PRT
<213> ORGANISM: Artificial Sequence

```
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (37)..(37)
<223> OTHER INFORMATION: AMIDATION

<400> SEQUENCE: 58

His Xaa Gln Gly Thr Phe Thr Ser Asp Tyr Ser Lys Tyr Leu Asp Ser
1               5                   10                  15

Arg Arg Ala Cys Asp Phe Val Gln Trp Leu Met Asn Thr Lys Arg Asn
            20                  25                  30

Arg Asn Asn Ile Ala
        35

<210> SEQ ID NO 59
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (20)..(20)
<223> OTHER INFORMATION: X=  cysteine residue in which the side-chain
      thiol is reacted with iodoacetamide
<220> FEATURE:
<221> NAME/KEY: MOD_RES
<222> LOCATION: (37)..(37)
<223> OTHER INFORMATION: AMIDATION

<400> SEQUENCE: 59

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Met Asn Thr Lys Arg Asn
            20                  25                  30

Arg Asn Asn Ile Ala
        35

<210> SEQ ID NO 60
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (20)..(20)
<223> OTHER INFORMATION: X= Cysteine PEGylated via the side-chain
      thiol with linear methoxyPEG 5 kDa
<220> FEATURE:
<221> NAME/KEY: MOD_RES
<222> LOCATION: (37)..(37)
<223> OTHER INFORMATION: AMIDATION

<400> SEQUENCE: 60
```

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Met Asn Thr Lys Arg Asn
            20                  25                  30

Arg Asn Asn Ile Ala
            35

<210> SEQ ID NO 61
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (20)..(20)
<223> OTHER INFORMATION: X= Cysteine PEGylated via the side-chain
      thiol with linear methoxyPEG 20 kDa
<220> FEATURE:
<221> NAME/KEY: MOD_RES
<222> LOCATION: (37)..(37)
<223> OTHER INFORMATION: AMIDATION

<400> SEQUENCE: 61

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Met Asn Thr Lys Arg Asn
            20                  25                  30

Arg Asn Asn Ile Ala
            35

<210> SEQ ID NO 62
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (20)..(20)
<223> OTHER INFORMATION: X= Cysteine residue PEGylated via the side-
      chain thiol with branched methoxyPEG 40 kDa
<220> FEATURE:
<221> NAME/KEY: MOD_RES
<222> LOCATION: (37)..(37)
<223> OTHER INFORMATION: AMIDATION

<400> SEQUENCE: 62

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Met Asn Thr Lys Arg Asn
            20                  25                  30

Arg Asn Asn Ile Ala
            35

<210> SEQ ID NO 63
<211> LENGTH: 37
<212> TYPE: PRT
<213> ORGANISM: Artificial Sequence

```
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (20)..(20)
<223> OTHER INFORMATION: X= Cys(Cholesteroyl), cysteine residue
      linked to cholesterol via the side-chain thiol
<220> FEATURE:
<221> NAME/KEY: MOD_RES
<222> LOCATION: (37)..(37)
<223> OTHER INFORMATION: AMIDATION

<400> SEQUENCE: 63

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Met Asn Thr Lys Arg Asn
            20                  25                  30

Arg Asn Asn Ile Ala
        35

<210> SEQ ID NO 64
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (27)..(27)
<223> OTHER INFORMATION: X= Nle
<220> FEATURE:
<221> NAME/KEY: MOD_RES
<222> LOCATION: (37)..(37)
<223> OTHER INFORMATION: AMIDATION

<400> SEQUENCE: 64

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala
        35

<210> SEQ ID NO 65
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (28)..(28)
<223> OTHER INFORMATION: X= Cys(CH2CONH2), cysteine residue in which
      the side-chain thiol was reacted with iodoacetamide
<220> FEATURE:
<221> NAME/KEY: MOD_RES
<222> LOCATION: (37)..(37)
```

```
<223> OTHER INFORMATION: AMIDATION

<400> SEQUENCE: 65

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Xaa Thr Lys Arg Asn
            20                  25                  30

Arg Asn Asn Ile Ala
        35

<210> SEQ ID NO 66
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (28)..(28)
<223> OTHER INFORMATION: X= Cysteine PEGylated via the side-chain
      thiol with linear methoxyPEG 5 kDa
<220> FEATURE:
<221> NAME/KEY: MOD_RES
<222> LOCATION: (37)..(37)
<223> OTHER INFORMATION: AMIDATION

<400> SEQUENCE: 66

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Xaa Thr Lys Arg Asn
            20                  25                  30

Arg Asn Asn Ile Ala
        35

<210> SEQ ID NO 67
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (28)..(28)
<223> OTHER INFORMATION: X= Cysteine PEGylated via the side-chain
      thiol with linear methoxyPEG 20 kDa
<220> FEATURE:
<221> NAME/KEY: MOD_RES
<222> LOCATION: (37)..(37)
<223> OTHER INFORMATION: AMIDATION

<400> SEQUENCE: 67

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Xaa Thr Lys Arg Asn
            20                  25                  30

Arg Asn Asn Ile Ala
        35
```

```
<210> SEQ ID NO 68
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (28)..(28)
<223> OTHER INFORMATION: X= Cysteine PEGylated via the side-chain
      thiol with branched mPEG
<220> FEATURE:
<221> NAME/KEY: MOD_RES
<222> LOCATION: (37)..(37)
<223> OTHER INFORMATION: AMIDATION

<400> SEQUENCE: 68

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Xaa Thr Lys Arg Asn
            20                  25                  30

Arg Asn Asn Ile Ala
        35

<210> SEQ ID NO 69
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (28)..(28)
<223> OTHER INFORMATION: X= Cys(Cholesteroyl),  Cysteine linked to
      cholesterol via the side-chain thiol
<220> FEATURE:
<221> NAME/KEY: MOD_RES
<222> LOCATION: (37)..(37)
<223> OTHER INFORMATION: AMIDATION

<400> SEQUENCE: 69

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Xaa Thr Lys Arg Asn
            20                  25                  30

Arg Asn Asn Ile Ala
        35

<210> SEQ ID NO 70
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (38)..(38)
```

<223> OTHER INFORMATION: X= Cys(CH2CONH2), Cysteine n which the side-
      chain thiol was reacted with iodoacetamide
<220> FEATURE:
<221> NAME/KEY: MOD_RES
<222> LOCATION: (38)..(38)
<223> OTHER INFORMATION: AMIDATION

<400> SEQUENCE: 70

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
            35

<210> SEQ ID NO 71
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (38)..(38)
<223> OTHER INFORMATION: X= Cysteine PEGylated via the side-chain
      thiol with linear methoxyPEG 5 kDa
<220> FEATURE:
<221> NAME/KEY: MOD_RES
<222> LOCATION: (38)..(38)
<223> OTHER INFORMATION: AMIDATION

<400> SEQUENCE: 71

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
            35

<210> SEQ ID NO 72
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (38)..(38)
<223> OTHER INFORMATION: X= Cysteine PEGylated via the side-chain
      thiol with linear methoxyPEG 20kDa
<220> FEATURE:
<221> NAME/KEY: MOD_RES
<222> LOCATION: (38)..(38)
<223> OTHER INFORMATION: AMIDATION

<400> SEQUENCE: 72

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 73
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (38)..(38)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (38)..(38)
<223> OTHER INFORMATION: AMIDATION

<400> SEQUENCE: 73

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 74
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (38)..(38)
<223> OTHER INFORMATION: X= Cys(Cholesteroyl), Cysteine linked to
      cholesterol via the side-chain thiol
<220> FEATURE:
<221> NAME/KEY: MOD_RES
<222> LOCATION: (38)..(38)
<223> OTHER INFORMATION: AMIDATION

<400> SEQUENCE: 74

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 75
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: AMIDATION

<400> SEQUENCE: 75

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 76
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (38)..(38)
<223> OTHER INFORMATION: AMIDATION

<400> SEQUENCE: 76

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 77
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= Cysteine  PEGylated via the side-chain
      thiol with linear methoxyPEG 5 kDa
<220> FEATURE:
<221> NAME/KEY: MOD_RES
<222> LOCATION: (38)..(38)
<223> OTHER INFORMATION: AMIDATION

<400> SEQUENCE: 77

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 78
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= Cysteine PEGylated via the side-chain
      thiol with linear methoxyPEG 20 kDa
<220> FEATURE:
<221> NAME/KEY: MOD_RES
<222> LOCATION: (38)..(38)
<223> OTHER INFORMATION: AMIDATION

<400> SEQUENCE: 78

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 79
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (38)..(38)
<223> OTHER INFORMATION: AMIDATION

<400> SEQUENCE: 79

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 80
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES

```
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= Cys(Cholesteroyl), Cysteine linked to
      cholesterol via the side-chain thiol
<220> FEATURE:
<221> NAME/KEY: MOD_RES
<222> LOCATION: (38)..(38)
<223> OTHER INFORMATION: AMIDATION

<400> SEQUENCE: 80

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
            35

<210> SEQ ID NO 81
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (37)..(37)
<223> OTHER INFORMATION: AMIDATION

<400> SEQUENCE: 81

His Ser Gln Gly Thr Phe Thr Ser Asp Tyr Ser Lys Tyr Leu Asp Ser
1               5                   10                  15

Arg Arg Ala Gln Cys Phe Val Gln Trp Leu Met Asn Thr Lys Arg Asn
            20                  25                  30

Arg Asn Asn Ile Ala
            35

<210> SEQ ID NO 82
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (21)..(21)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (37)..(37)
<223> OTHER INFORMATION: AMIDATION

<400> SEQUENCE: 82

His Xaa Gln Gly Thr Phe Thr Ser Asp Tyr Ser Lys Tyr Leu Asp Ser
1               5                   10                  15

Arg Arg Ala Gln Xaa Phe Val Gln Trp Leu Met Asn Thr Lys Arg Asn
            20                  25                  30
```

Arg Asn Asn Ile Ala
        35

<210> SEQ ID NO 83
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (21)..(21)
<223> OTHER INFORMATION: X= Cysteine  PEGylated via the side-chain
      thiol with linear methoxyPEG 5 kDa
<220> FEATURE:
<221> NAME/KEY: MOD_RES
<222> LOCATION: (37)..(37)
<223> OTHER INFORMATION: AMIDATION

<400> SEQUENCE: 83

His Xaa Gln Gly Thr Phe Thr Ser Asp Tyr Ser Lys Tyr Leu Asp Ser
1               5                   10                  15

Arg Arg Ala Gln Xaa Phe Val Gln Trp Leu Met Asn Thr Lys Arg Asn
            20                  25                  30

Arg Asn Asn Ile Ala
        35

<210> SEQ ID NO 84
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (21)..(21)
<223> OTHER INFORMATION: X= Cysteine PEGylated via the side-chain
      thiol with linear methoxyPEG 20 kDa
<220> FEATURE:
<221> NAME/KEY: MOD_RES
<222> LOCATION: (37)..(37)
<223> OTHER INFORMATION: AMIDATION

<400> SEQUENCE: 84

His Xaa Gln Gly Thr Phe Thr Ser Asp Tyr Ser Lys Tyr Leu Asp Ser
1               5                   10                  15

Arg Arg Ala Gln Xaa Phe Val Gln Trp Leu Met Asn Thr Lys Arg Asn
            20                  25                  30

Arg Asn Asn Ile Ala
        35

<210> SEQ ID NO 85
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES

```
<222> LOCATION: (2)..(2)
<223> OTHER INFORMATION: X= D-Serine
<220> FEATURE:
<221> NAME/KEY: MOD_RES
<222> LOCATION: (21)..(21)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (37)..(37)
<223> OTHER INFORMATION: AMIDATION

<400> SEQUENCE: 85

His Xaa Gln Gly Thr Phe Thr Ser Asp Tyr Ser Lys Tyr Leu Asp Ser
1               5                   10                  15

Arg Arg Ala Gln Xaa Phe Val Gln Trp Leu Met Asn Thr Lys Arg Asn
            20                  25                  30

Arg Asn Asn Ile Ala
        35

<210> SEQ ID NO 86
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (21)..(21)
<223> OTHER INFORMATION: X= Cys(Cholesteroyl), Cysteine linked to
      cholesterol via the side-chain thiol
<220> FEATURE:
<221> NAME/KEY: MOD_RES
<222> LOCATION: (37)..(37)
<223> OTHER INFORMATION: AMIDATION

<400> SEQUENCE: 86

His Xaa Gln Gly Thr Phe Thr Ser Asp Tyr Ser Lys Tyr Leu Asp Ser
1               5                   10                  15

Arg Arg Ala Gln Xaa Phe Val Gln Trp Leu Met Asn Thr Lys Arg Asn
            20                  25                  30

Arg Asn Asn Ile Ala
        35

<210> SEQ ID NO 87
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=D-Serine
<220> FEATURE:
<221> NAME/KEY: MOD_RES
<222> LOCATION: (37)..(37)
<223> OTHER INFORMATION: AMIDATION

<400> SEQUENCE: 87

His Xaa Gln Gly Thr Phe Thr Ser Asp Tyr Ser Lys Tyr Leu Asp Ser
1               5                   10                  15

Arg Arg Ala Gln Asp Phe Val Cys Trp Leu Met Asn Thr Lys Arg Asn
            20                  25                  30
```

Arg Asn Asn Ile Ala
        35

<210> SEQ ID NO 88
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (24)..(24)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (37)..(37)
<223> OTHER INFORMATION: AMIDATION

<400> SEQUENCE: 88

His Xaa Gln Gly Thr Phe Thr Ser Asp Tyr Ser Lys Tyr Leu Asp Ser
1               5                   10                  15

Arg Arg Ala Gln Asp Phe Val Xaa Trp Leu Met Asn Thr Lys Arg Asn
            20                  25                  30

Arg Asn Asn Ile Ala
        35

<210> SEQ ID NO 89
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (24)..(24)
<223> OTHER INFORMATION: X= Cysteine  PEGylated via the side-
      chain thiol with linear methoxyPEG 5 kDa
<220> FEATURE:
<221> NAME/KEY: MOD_RES
<222> LOCATION: (37)..(37)
<223> OTHER INFORMATION: AMIDATION

<400> SEQUENCE: 89

His Xaa Gln Gly Thr Phe Thr Ser Asp Tyr Ser Lys Tyr Leu Asp Ser
1               5                   10                  15

Arg Arg Ala Gln Asp Phe Val Xaa Trp Leu Met Asn Thr Lys Arg Asn
            20                  25                  30

Arg Asn Asn Ile Ala
        35

<210> SEQ ID NO 90
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES

```
<222> LOCATION: (2)..(2)
<223> OTHER INFORMATION: X= D-Serine
<220> FEATURE:
<221> NAME/KEY: MOD_RES
<222> LOCATION: (24)..(24)
<223> OTHER INFORMATION: X= Cysteine PEGylated via the side-
      chain thiol with linear methoxyPEG 20 kDa
<220> FEATURE:
<221> NAME/KEY: MOD_RES
<222> LOCATION: (37)..(37)
<223> OTHER INFORMATION: AMIDATION

<400> SEQUENCE: 90

His Xaa Gln Gly Thr Phe Thr Ser Asp Tyr Ser Lys Tyr Leu Asp Ser
1               5                   10                  15

Arg Arg Ala Gln Asp Phe Val Xaa Trp Leu Met Asn Thr Lys Arg Asn
            20                  25                  30

Arg Asn Asn Ile Ala
            35

<210> SEQ ID NO 91
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=D-Serine
<220> FEATURE:
<221> NAME/KEY: MOD_RES
<222> LOCATION: (24)..(24)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (37)..(37)
<223> OTHER INFORMATION: AMIDATION

<400> SEQUENCE: 91

His Xaa Gln Gly Thr Phe Thr Ser Asp Tyr Ser Lys Tyr Leu Asp Ser
1               5                   10                  15

Arg Arg Ala Gln Asp Phe Val Xaa Trp Leu Met Asn Thr Lys Arg Asn
            20                  25                  30

Arg Asn Asn Ile Ala
            35

<210> SEQ ID NO 92
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (24)..(24)
<223> OTHER INFORMATION: X= Cys(Cholesteroyl), Cysteine linked to
      cholesterol via the side-chain thiol
<220> FEATURE:
<221> NAME/KEY: MOD_RES
<222> LOCATION: (37)..(37)
<223> OTHER INFORMATION: AMIDATION

<400> SEQUENCE: 92
```

His Xaa Gln Gly Thr Phe Thr Ser Asp Tyr Ser Lys Tyr Leu Asp Ser
1               5                   10                  15

Arg Arg Ala Gln Asp Phe Val Xaa Trp Leu Met Asn Thr Lys Arg Asn
            20                  25                  30

Arg Asn Asn Ile Ala
        35

<210> SEQ ID NO 93
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (37)..(37)
<223> OTHER INFORMATION: AMIDATION

<400> SEQUENCE: 93

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Val Asn Thr Lys Arg Asn
            20                  25                  30

Arg Asn Asn Ile Ala
        35

<210> SEQ ID NO 94
<211> LENGTH: 33
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (33)..(33)
<223> OTHER INFORMATION: AMIDATION

<400> SEQUENCE: 94

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg

<210> SEQ ID NO 95
<211> LENGTH: 32
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (32)..(32)
<223> OTHER INFORMATION: AMIDATION

<400> SEQUENCE: 95

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

```
<210> SEQ ID NO 96
<211> LENGTH: 31
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (31)..(31)
<223> OTHER INFORMATION: AMIDATION

<400> SEQUENCE: 96

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (30)..(30)
<223> OTHER INFORMATION: AMIDATION

<400> SEQUENCE: 97

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys
            20                  25                  30

<210> SEQ ID NO 98
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X=Methionine sulfoxide
<220> FEATURE:
<221> NAME/KEY: MOD_RES
<222> LOCATION: (38)..(38)
<223> OTHER INFORMATION: AMIDATION

<400> SEQUENCE: 98

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Cys
        35

<210> SEQ ID NO 99
<211> LENGTH: 38
<212> TYPE: PRT
<213> ORGANISM: Artificial Sequence
```

```
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: MOD_RES
<222> LOCATION: (38)..(38)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (38)..(38)
<223> OTHER INFORMATION: AMIDATION

<400> SEQUENCE: 99

His Xaa Asp Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 100
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (38)..(38)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (38)..(38)
<223> OTHER INFORMATION: AMIDATION

<400> SEQUENCE: 100

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 101
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (38)..(38)
<223> OTHER INFORMATION: X= Cys(CH2CONH2), Cysteine in which the side-
      chain thiol was reacted with iodoacetamide
<220> FEATURE:
<221> NAME/KEY: MOD_RES
```

```
<222> LOCATION: (38)..(38)
<223> OTHER INFORMATION: AMIDATION

<400> SEQUENCE: 101

His Xaa Asp Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
            35

<210> SEQ ID NO 102
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X=Methionine sulfoxide
<220> FEATURE:
<221> NAME/KEY: MOD_RES
<222> LOCATION: (38)..(38)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (38)..(38)
<223> OTHER INFORMATION: AMIDATION

<400> SEQUENCE: 102

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Xaa
            35

<210> SEQ ID NO 103
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X=Methionine sulfoxide
<220> FEATURE:
<221> NAME/KEY: MOD_RES
<222> LOCATION: (38)..(38)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (38)..(38)
<223> OTHER INFORMATION: AMIDATION

<400> SEQUENCE: 103

His Xaa Gln Gly Thr Phe Thr Ser Asp Tyr Ser Lys Tyr Leu Asp Ser
```

```
                1               5                   10                  15
Arg Arg Ala Gln Asp Phe Val Gln Trp Leu Xaa Asn Thr Lys Arg Asn
            20                  25                  30

Arg Asn Asn Ile Ala Xaa
        35

<210> SEQ ID NO 104
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X=Methionine sulfoxide
<220> FEATURE:
<221> NAME/KEY: MOD_RES
<222> LOCATION: (38)..(38)
<223> OTHER INFORMATION: X= CysteinePEGylated via the side-chain thiol
      with branched methoxyPEG 60 kDa
<220> FEATURE:
<221> NAME/KEY: MOD_RES
<222> LOCATION: (38)..(38)
<223> OTHER INFORMATION: AMIDATION

<400> SEQUENCE: 104

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Xaa
        35

<210> SEQ ID NO 105
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cys(Cholesteroyl), Cysteine linked to
      cholesterol via the side-chain thiol
<220> FEATURE:
<221> NAME/KEY: MOD_RES
<222> LOCATION: (38)..(38)
<223> OTHER INFORMATION: X= Cys(Cholesteroyl), Cysteine linked to
      cholesterol via the side-chain thiol

<400> SEQUENCE: 105

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30
```

Arg Asn Asn Ile Ala Xaa
            35

<210> SEQ ID NO 106
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (20)..(20)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (37)..(37)
<223> OTHER INFORMATION: AMIDATION

<400> SEQUENCE: 106

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Met Asn Thr Lys Arg Asn
            20                  25                  30

Arg Asn Asn Ile Ala
            35

<210> SEQ ID NO 107
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (37)..(37)
<223> OTHER INFORMATION: AMIDATION

<400> SEQUENCE: 107

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Met Asn Thr Lys Arg Asn
            20                  25                  30

Arg Asn Asn Ile Ala
            35

<210> SEQ ID NO 108
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)

```
<223> OTHER INFORMATION: X=Aib
<220> FEATURE:
<221> NAME/KEY: MOD_RES
<222> LOCATION: (21)..(21)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (37)..(37)
<223> OTHER INFORMATION: AMIDATION

<400> SEQUENCE: 108

His Xaa Gln Gly Thr Phe Thr Ser Asp Tyr Ser Lys Tyr Leu Asp Ser
1               5                   10                  15

Arg Arg Ala Gln Xaa Phe Val Gln Trp Leu Met Asn Thr Lys Arg Asn
            20                  25                  30

Arg Asn Asn Ile Ala
            35

<210> SEQ ID NO 109
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (21)..(21)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (37)..(37)
<223> OTHER INFORMATION: AMIDATION

<400> SEQUENCE: 109

His Xaa Gln Gly Thr Phe Thr Ser Asp Tyr Ser Lys Tyr Leu Asp Ser
1               5                   10                  15

Arg Arg Ala Gln Xaa Phe Val Gln Trp Leu Met Asn Thr Lys Arg Asn
            20                  25                  30

Arg Asn Asn Ile Ala
            35

<210> SEQ ID NO 110
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (24)..(24)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION
```

<400> SEQUENCE: 110

His Xaa Gln Gly Thr Phe Thr Ser Asp Tyr Ser Lys Tyr Leu Asp Ser
1               5                   10                  15

Arg Arg Ala Gln Asp Phe Val Xaa Trp Leu Xaa Asn Thr Lys Arg Asn
            20                  25                  30

Arg Asn Asn Ile Ala
            35

<210> SEQ ID NO 111
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (24)..(24)
<223> OTHER INFORMATION: X= Cysteine PEGylated via the side-
      chain thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 111

His Xaa Gln Gly Thr Phe Thr Ser Asp Tyr Ser Lys Tyr Leu Asp Ser
1               5                   10                  15

Arg Arg Ala Gln Asp Phe Val Xaa Trp Leu Xaa Asn Thr Lys Arg Asn
            20                  25                  30

Arg Asn Asn Ile Ala
            35

<210> SEQ ID NO 112
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (28)..(28)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (37)..(37)
<223> OTHER INFORMATION: AMIDATION

<400> SEQUENCE: 112

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Xaa Thr Lys Arg Asn
            20                  25                  30

Arg Asn Asn Ile Ala

-continued

```
<210> SEQ ID NO 113
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (28)..(28)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (37)..(37)
<223> OTHER INFORMATION: AMIDATION

<400> SEQUENCE: 113

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Xaa Thr Lys Arg Asn
            20                  25                  30

Arg Asn Asn Ile Ala
        35

<210> SEQ ID NO 114
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= D-Serine
<220> FEATURE:
<221> NAME/KEY: LIPID
<222> LOCATION: (38)..(38)
<223> OTHER INFORMATION: X= K PALMITATE
<220> FEATURE:
<221> NAME/KEY: MOD_RES
<222> LOCATION: (38)..(38)
<223> OTHER INFORMATION: AMIDATION

<400> SEQUENCE: 114

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Xaa
        35

<210> SEQ ID NO 115
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: X= = desamino-His
<220> FEATURE:
```

```
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: AMIDATION

<400> SEQUENCE: 115

Xaa Xaa Gln Gly Thr Phe Thr Ser Asp Tyr Ser Lys Tyr Leu Asp Ser
 1               5                  10                  15

Arg Arg Ala Gln Asp Phe Val Gln Trp Leu Xaa Asn Thr Lys Arg Asn
            20                  25                  30

Arg Asn Asn Ile Ala Cys
        35

<210> SEQ ID NO 116
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: X= desamino-His
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (38)..(38)
<223> OTHER INFORMATION: AMIDATION

<400> SEQUENCE: 116

Xaa Xaa Gln Gly Thr Phe Thr Ser Asp Tyr Ser Lys Tyr Leu Asp Ser
 1               5                  10                  15

Arg Arg Ala Gln Asp Phe Val Gln Trp Leu Xaa Asn Thr Lys Arg Asn
            20                  25                  30

Arg Asn Asn Ile Ala Xaa
        35

<210> SEQ ID NO 117
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: X= desamino-His
<220> FEATURE:
<221> NAME/KEY: MOD_RES
<222> LOCATION: (2)..(2)
<223> OTHER INFORMATION: X= Aib
```

```
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cysteine PEGylated via the side-
      chain thiol with branched mPEG 40 kDa
<220> FEATURE:
<221> NAME/KEY: MOD_RES
<222> LOCATION: (38)..(38)
<223> OTHER INFORMATION: AMIDATION

<400> SEQUENCE: 117

Xaa Xaa Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Xaa
        35

<210> SEQ ID NO 118
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: X= desamino-His
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cys(Cholesteroyl), Cysteine linked to
      cholesterol via the side-chain thiol
<220> FEATURE:
<221> NAME/KEY: MOD_RES
<222> LOCATION: (38)..(38)
<223> OTHER INFORMATION: AMIDATION

<400> SEQUENCE: 118

Xaa Xaa Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Xaa
        35

<210> SEQ ID NO 119
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
```

```
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: AMIDATION

<400> SEQUENCE: 119

His Xaa Asp Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Cys
        35

<210> SEQ ID NO 120
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cysteine PEGylated via the side-
      chain thiol with branched mPEG 40 kDa
<220> FEATURE:
<221> NAME/KEY: MOD_RES
<222> LOCATION: (38)..(38)
<223> OTHER INFORMATION: AMIDATION

<400> SEQUENCE: 120

His Xaa Asp Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Xaa
        35

<210> SEQ ID NO 121
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cys(Cholesteroyl), Cysteine linked to
      cholesterol via the side-chain thiol
<220> FEATURE:
<221> NAME/KEY: MOD_RES
<222> LOCATION: (38)..(38)
<223> OTHER INFORMATION: AMIDATION
```

<400> SEQUENCE: 121

His Xaa Asp Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Xaa
            35

<210> SEQ ID NO 122
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 122

His Xaa Gln Gly Thr Phe Thr Ser Asp Tyr Cys Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala
            35

<210> SEQ ID NO 123
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (11)..(11)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 123

His Xaa Gln Gly Thr Phe Thr Ser Asp Tyr Xaa Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala
            35

<210> SEQ ID NO 124
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (11)..(11)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 124

His Xaa Gln Gly Thr Phe Thr Ser Asp Tyr Xaa Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala
            35

<210> SEQ ID NO 125
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 125

His Xaa Gln Gly Thr Phe Thr Ser Asp Tyr Ser Cys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala
            35

<210> SEQ ID NO 126
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES

```
<222> LOCATION: (2)..(2)
<223> OTHER INFORMATION: X= Aib
<220> FEATURE:
<221> NAME/KEY: MOD_RES
<222> LOCATION: (12)..(12)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 126

His Xaa Gln Gly Thr Phe Thr Ser Asp Tyr Ser Xaa Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala
            35

<210> SEQ ID NO 127
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (12)..(12)
<223> OTHER INFORMATION: X= Cysteine PEGylated via the side-
      chain thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 127

His Xaa Gln Gly Thr Phe Thr Ser Asp Tyr Ser Xaa Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala
            35

<210> SEQ ID NO 128
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-
```

```
      chain thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 128

His Xaa Asp Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys Arg Asn
            20                  25                  30

Arg Asn Asn Ile Ala
        35

<210> SEQ ID NO 129
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 129

His Xaa Gln Gly Thr Phe Thr Ser Asp Tyr Ser Lys Tyr Leu Asp Ser
1               5                   10                  15

Arg Arg Ala Gln Asp Cys Val Gln Trp Leu Xaa Asn Thr Lys Arg Asn
            20                  25                  30

Arg Asn Asn Ile Ala
        35

<210> SEQ ID NO 130
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (22)..(22)
<223> OTHER INFORMATION: X= Cys(Cholesteroyl), Cysteine linked to
      cholesterol via the side-chain thiol
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 130
```

His Xaa Gln Gly Thr Phe Thr Ser Asp Tyr Ser Lys Tyr Leu Asp Ser
1               5                   10                  15

Arg Arg Ala Gln Asp Xaa Val Gln Trp Leu Xaa Asn Thr Lys Arg Asn
            20              25                  30

Arg Asn Asn Ile Ala
            35

<210> SEQ ID NO 131
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: X= desamino-His
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 131

Xaa Xaa Asp Gly Thr Phe Thr Ser Asp Tyr Ser Lys Tyr Leu Asp Ser
1               5                   10                  15

Arg Arg Ala Cys Asp Phe Val Gln Trp Leu Xaa Asn Thr Lys Arg Asn
            20              25                  30

Arg Asn Asn Ile Ala
            35

<210> SEQ ID NO 132
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: X= desamino-His
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 132

Xaa Xaa Asp Gly Thr Phe Thr Ser Asp Tyr Ser Lys Tyr Leu Asp Ser
1               5                   10                  15

-continued

```
Arg Arg Ala Xaa Asp Phe Val Gln Trp Leu Xaa Asn Thr Lys Arg Asn
         20                  25                  30

Arg Asn Asn Ile Ala
         35

<210> SEQ ID NO 133
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (30)..(30)
<223> OTHER INFORMATION: AMIDATION

<400> SEQUENCE: 133

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys
         20                  25                  30

<210> SEQ ID NO 134
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (30)..(30)
<223> OTHER INFORMATION: AMIDATION

<400> SEQUENCE: 134

His Xaa Asp Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys
         20                  25                  30

<210> SEQ ID NO 135
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 135
```

```
His Xaa Gln Gly Thr Phe Thr Ser Asp Tyr Ser Lys Tyr Leu Asp Ser
1               5                   10                  15

Arg Arg Ala Cys Asp Phe Val Gln Trp Leu Xaa Asn Thr Lys Arg Asn
            20                  25                  30

Arg Asn Asn Ile Ala
        35

<210> SEQ ID NO 136
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cys(CH2CONH2), Cysteine in which the side-
      chain thiol was reacted with iodoacetamide
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 136

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys Arg Asn
            20                  25                  30

Arg Asn Asn Ile Ala
        35

<210> SEQ ID NO 137
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (37)..(37)
<223> OTHER INFORMATION: AMIDATION

<400> SEQUENCE: 137

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys Arg Asn
            20                  25                  30
```

```
Arg Asn Asn Ile Ala
            35

<210> SEQ ID NO 138
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (30)..(30)
<223> OTHER INFORMATION: AMIDATION

<400> SEQUENCE: 138

His Xaa Gln Gly Thr Phe Thr Ser Asp Tyr Ser Lys Tyr Leu Asp Ser
1               5                   10                  15

Arg Arg Ala Cys Asp Phe Val Gln Trp Leu Xaa Asn Thr Lys
            20                  25                  30

<210> SEQ ID NO 139
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (30)..(30)
<223> OTHER INFORMATION: AMIDATION

<400> SEQUENCE: 139

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
```

```
<222> LOCATION: (27)..(27)
<223> OTHER INFORMATION: X= Methionine sulfoxide
<220> FEATURE:
<221> NAME/KEY: MOD_RES
<222> LOCATION: (30)..(30)
<223> OTHER INFORMATION: AMIDATION

<400> SEQUENCE: 140

His Xaa Asp Gly Thr Phe Thr Ser Asp Tyr Ser Lys Tyr Leu Asp Ser
1               5                   10                  15

Arg Arg Ala Cys Asp Phe Val Gln Trp Leu Xaa Asn Thr Lys
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (30)..(30)
<223> OTHER INFORMATION: AMIDATION

<400> SEQUENCE: 141

His Xaa Asp Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys
            20                  25                  30

<210> SEQ ID NO 142
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cys(N-ethylmaleimidyl)
<220> FEATURE:
<221> NAME/KEY: MOD_RES
<222> LOCATION: (38)..(38)
<223> OTHER INFORMATION: AMIDATION

<400> SEQUENCE: 142

His Xaa Asp Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
```

-continued

```
                20                  25                  30

Arg Asn Asn Ile Ala Xaa
            35

<210> SEQ ID NO 143
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X=Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cys(Cholesteryl), Cysteine linked to
      cholesterol via the side-chain thiol
<220> FEATURE:
<221> NAME/KEY: MOD_RES
<222> LOCATION: (38)..(38)
<223> OTHER INFORMATION: AMIDATION

<400> SEQUENCE: 143

His Xaa Asp Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys Arg Asn
                20                  25                  30

Arg Asn Asn Ile Ala Xaa
            35

<210> SEQ ID NO 144
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cys(Cholesteryl), Cysteine linked to
      cholesterol via the side-chain thiol
<220> FEATURE:
<221> NAME/KEY: MOD_RES
<222> LOCATION: (38)..(38)
<223> OTHER INFORMATION: AMIDATION

<400> SEQUENCE: 144
```

```
His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys Arg Asn
            20                  25                  30

Arg Asn Asn Ile Ala Xaa
            35

<210> SEQ ID NO 145
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cys(N-ethylmaleimidyl)
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (30)..(30)
<223> OTHER INFORMATION: AMIDATION

<400> SEQUENCE: 145

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys
            20                  25                  30

<210> SEQ ID NO 146
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cys(N-ethylmaleimidyl)
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (30)..(30)
<223> OTHER INFORMATION: AMIDATION

<400> SEQUENCE: 146

His Xaa Asp Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys
            20                  25                  30

<210> SEQ ID NO 147
<211> LENGTH: 30
<212> TYPE: PRT
<213> ORGANISM: Artificial Sequence
```

```
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (30)..(30)
<223> OTHER INFORMATION: AMIDATION

<400> SEQUENCE: 147

His Xaa Gln Gly Thr Phe Thr Ser Asp Tyr Ser Lys Tyr Leu Asp Ser
 1               5                  10                  15

Arg Arg Ala Cys Asp Phe Val Gln Trp Leu Met Asn Thr Lys
            20                  25                  30

<210> SEQ ID NO 148
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cys(N-ethylmaleimidyl)
<220> FEATURE:
<221> NAME/KEY: MOD_RES
<222> LOCATION: (30)..(30)
<223> OTHER INFORMATION: AMIDATION

<400> SEQUENCE: 148

His Xaa Gln Gly Thr Phe Thr Ser Asp Tyr Ser Lys Tyr Leu Asp Ser
 1               5                  10                  15

Arg Arg Ala Xaa Asp Phe Val Gln Trp Leu Met Asn Thr Lys
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (30)..(30)
<223> OTHER INFORMATION: X= D-Lysine
<220> FEATURE:
<221> NAME/KEY: MOD_RES
<222> LOCATION: (30)..(30)
<223> OTHER INFORMATION: AMIDATION

<400> SEQUENCE: 149

His Xaa Asp Gly Thr Phe Thr Ser Asp Tyr Ser Lys Tyr Leu Asp Ser
 1               5                  10                  15

Arg Arg Ala Cys Asp Phe Val Gln Trp Leu Xaa Asn Thr Xaa
            20                  25                  30
```

<210> SEQ ID NO 150
<211> LENGTH: 30
<212> TYPE: PRT
<213> ORGANISM: Artificial Sequence
<220> FEATURE:
<223> OTHER INFORMATION: Synthetic peptide based on the human oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cys(N-ethylmaleimidyl)
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (30)..(30)
<223> OTHER INFORMATION: X= D-Lysine
<220> FEATURE:
<221> NAME/KEY: MOD_RES
<222> LOCATION: (30)..(30)
<223> OTHER INFORMATION: AMIDATION

<400> SEQUENCE: 150

His Xaa Asp Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Xaa
            20                  25                  30

<210> SEQ ID NO 151
<211> LENGTH: 38
<212> TYPE: PRT
<213> ORGANISM: Artificial Sequence
<220> FEATURE:
<223> OTHER INFORMATION: Synthetic peptide based on the human oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: AMIDATION

<400> SEQUENCE: 151

His Xaa Asp Gly Thr Phe Thr Ser Asp Tyr Ser Lys Tyr Leu Asp Ser
1               5                   10                  15

Glu Ala Ala Gln Asp Phe Val Gln Trp Leu Xaa Asn Thr Lys Arg Asn
            20                  25                  30

Arg Asn Asn Ile Ala Cys
        35

<210> SEQ ID NO 152
<211> LENGTH: 19
<212> TYPE: PRT
<213> ORGANISM: Artificial Sequence
<220> FEATURE:
<223> OTHER INFORMATION: Synthetic peptide based on the human oxyntomodulin sequence
<220> FEATURE:

```
<221> NAME/KEY: MOD_RES
<222> LOCATION: (2)..(2)
<223> OTHER INFORMATION: X= Aib
<220> FEATURE:
<221> NAME/KEY: MISC_FEATURE
<222> LOCATION: (17)..(17)
<223> OTHER INFORMATION: 1-amino-4,7,10-trioxa-13-tridecanamine
      succinimic acid inserted as a spacer
<220> FEATURE:
<221> NAME/KEY: MOD_RES
<222> LOCATION: (19)..(19)
<223> OTHER INFORMATION: AMIDATION

<400> SEQUENCE: 152

His Xaa Asp Gly Thr Phe Thr Ser Asp Tyr Ser Lys Tyr Leu Asp Ser
1               5                   10                  15

Xaa Glu Cys

<210> SEQ ID NO 153
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cys(N-ethylmaleimidyl)
<220> FEATURE:
<221> NAME/KEY: MOD_RES
<222> LOCATION: (38)..(38)
<223> OTHER INFORMATION: AMIDATION

<400> SEQUENCE: 153

His Xaa Asp Gly Thr Phe Thr Ser Asp Tyr Ser Lys Tyr Leu Asp Ser
1               5                   10                  15

Glu Ala Ala Gln Asp Phe Val Gln Trp Leu Xaa Asn Thr Lys Arg Asn
            20                  25                  30

Arg Asn Asn Ile Ala Xaa
            35

<210> SEQ ID NO 154
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MOD_RES
<222> LOCATION: (38)..(38)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (38)..(38)
```

<223> OTHER INFORMATION: AMIDATION

<400> SEQUENCE: 154

His Xaa Asp Gly Thr Phe Thr Ser Asp Tyr Ser Lys Tyr Leu Asp Ser
1               5                   10                  15

Glu Ala Ala Gln Asp Phe Val Gln Trp Leu Xaa Asn Thr Lys Arg Asn
            20                  25                  30

Arg Asn Asn Ile Ala Xaa
        35

<210> SEQ ID NO 155
<211> LENGTH: 44
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (27)..(27)
<223> OTHER INFORMATION: X= Methionine sulfoxide
<220> FEATURE:
<221> NAME/KEY: MISC_FEATURE
<222> LOCATION: (38)..(38)
<223> OTHER INFORMATION: 1-amino-4,7,10-trioxa-13-tridecanamine
      succinimic acid inserted as a spacer

<400> SEQUENCE: 155

His Xaa Asp Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr Lys Arg Asn
            20                  25                  30

Arg Asn Asn Ile Ala Xaa Glu Glu Glu Glu Glu Cys
        35                  40

<210> SEQ ID NO 156
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (37)..(37)
<223> OTHER INFORMATION: AMIDATION

<400> SEQUENCE: 156

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Ala Asn Thr Lys Arg Asn
            20                  25                  30

Arg Asn Asn Ile Ala
        35

```
<210> SEQ ID NO 157
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (37)..(37)
<223> OTHER INFORMATION: AMIDATION

<400> SEQUENCE: 157

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Val Asn Thr Lys Arg Asn
            20                  25                  30

Arg Asn Asn Ile Ala
        35

<210> SEQ ID NO 158
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= Aib
<220> FEATURE:
<221> NAME/KEY: MOD_RES
<222> LOCATION: (37)..(37)
<223> OTHER INFORMATION: AMIDATION

<400> SEQUENCE: 158

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys Arg Asn
            20                  25                  30

Arg Asn Asn Ile Ala
        35

<210> SEQ ID NO 159
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
```

```
<223> OTHER INFORMATION: X= Aib
<220> FEATURE:
<221> NAME/KEY: MOD_RES
<222> LOCATION: (20)..(20)
<223> OTHER INFORMATION: X= Cysteine PEGylated via the side-chain
      thiol with branched mPEG 40 kDa
<220> FEATURE:
<221> NAME/KEY: MOD_RES
<222> LOCATION: (27)..(27)
<223> OTHER INFORMATION: X= O-methyl-homoserine
<220> FEATURE:
<221> NAME/KEY: MOD_RES
<222> LOCATION: (37)..(37)
<223> OTHER INFORMATION: AMIDATION

<400> SEQUENCE: 159

His Xaa Gln Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr Lys Arg Asn
            20                  25                  30

Arg Asn Asn Ile Ala
        35

<210> SEQ ID NO 160
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (1)..(1)
<223> OTHER INFORMATION: X= His, imidazole-lactic acid (ImiH);
      desamino- His (?NH2-H), acetyl His, pyroglutamyl His, N-methyl-
      His (Me-H), N,N-dimethyl-His (Me2-H); Benzoyl His (Bz-H),
      Benzyl His (Bzl-H), and Phe
<220> FEATURE:
<221> NAME/KEY: MOD_RES
<222> LOCATION: (2)..(2)
<223> OTHER INFORMATION: X= Ser, Gly, Ala, Arg; Asn, Asp, Glu, Gln,
      His, Ile, Lys, Met, Phe, Pro, Thr, Trp, Tyr, Val, D-Ala,
      D-Ser, and aib
<220> FEATURE:
<221> NAME/KEY: MOD_RES
<222> LOCATION: (3)..(3)
<223> OTHER INFORMATION: X= Gln, Asp, Glu, Pro, Leu or L-norleucine
<220> FEATURE:
<221> NAME/KEY: MOD_RES
<222> LOCATION: (11)..(11)
<223> OTHER INFORMATION: X= Ser, Ala, Cys, Cys(mPEG), or Cys
      (cholesteryl)
<220> FEATURE:
<221> NAME/KEY: MOD_RES
<222> LOCATION: (12)..(12)
<223> OTHER INFORMATION: X= Lys, Cys, Cys(mPEG), or Cys(cholesteryl)
<220> FEATURE:
<221> NAME/KEY: MOD_RES
<222> LOCATION: (16)..(16)
<223> OTHER INFORMATION: X= Ser or Ala
<220> FEATURE:
<221> NAME/KEY: MOD_RES
<222> LOCATION: (17)..(17)
<223> OTHER INFORMATION: X= any amino acid
<220> FEATURE:
<221> NAME/KEY: MOD_RES
<222> LOCATION: (18)..(18)
<223> OTHER INFORMATION: X= any amino acid
<220> FEATURE:
<221> NAME/KEY: MOD_RES
<222> LOCATION: (20)..(20)
<223> OTHER INFORMATION: X= Gln, Cys, Cys(mPEG), or Cys(cholesteryl)
<220> FEATURE:
<221> NAME/KEY: MOD_RES
<222> LOCATION: (21)..(21)
<223> OTHER INFORMATION: X= Asp, Cys, Cys(mPEG), or Cys(cholesteryl)
```

```
<220> FEATURE:
<221> NAME/KEY: MOD_RES
<222> LOCATION: (24)..(24)
<223> OTHER INFORMATION: X= Gln, Cys, Cys(mPEG), or Cys(cholesteryl)
<220> FEATURE:
<221> NAME/KEY: MOD_RES
<222> LOCATION: (27)..(27)
<223> OTHER INFORMATION: X= Met, Met(O), Val, norleucine, alanine, ?a-
      aminoisobutyric acid or O-methyl-homoserine
<220> FEATURE:
<221> NAME/KEY: MOD_RES
<222> LOCATION: (28)..(28)
<223> OTHER INFORMATION: X= Asn, Cys, Cys(mPEG), or Cys(cholesteryl)
<220> FEATURE:
<221> NAME/KEY: MOD_RES
<222> LOCATION: (29)..(29)
<223> OTHER INFORMATION: X= Thr, Cys, Cys(mPEG), or Cys(cholesteryl)
<220> FEATURE:
<221> NAME/KEY: MOD_RES
<222> LOCATION: (36)..(36)
<223> OTHER INFORMATION: X= Ile, Cys, Cys(mPEG), or Cys(cholesteryl)
<220> FEATURE:
<221> NAME/KEY: MOD_RES
<222> LOCATION: (37)..(37)
<223> OTHER INFORMATION: X= Ala, Cys, Cys(mPEG), or Cys(cholesteryl)
<220> FEATURE:
<221> NAME/KEY: MOD_RES
<222> LOCATION: (38)..(38)
<223> OTHER INFORMATION: X = amide, carboxylic acid (COOH),
      carboxamide, secondary amide, Ala, K(palmitoyl), Cys, Cys(mPEG),
      Cys(cholesteryl), or any linker to which mPEG or cholesterol is
      linked with a chemical bond

<400> SEQUENCE: 160

Xaa Xaa Xaa Gly Thr Phe Thr Ser Asp Tyr Xaa Xaa Tyr Leu Asp Xaa
1               5                   10                  15

Xaa Xaa Ala Xaa Xaa Phe Val Xaa Trp Leu Xaa Xaa Xaa L

```
<221> NAME/KEY: MOD_RES
<222> LOCATION: (2)..(2)
<223> OTHER INFORMATION: X= Ser, Gly, Ala, Arg; Asn, Asp, Glu, Gln,
      His, Ile, Lys, Met, Phe, Pro, Thr, Trp, Tyr, Val, D-Ala, D-Ser,
      and aib

<400> SEQUENCE: 162

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 163
<211> LENGTH: 37
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (3)..(3)
<223> OTHER INFORMATION: X= Gln, Asp, Glu, Pro, Leu or L-norleucine

<400> SEQUENCE: 163

His Ser Xaa Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 164
<211> LENGTH: 38
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (11)..(11)
<223> OTHER INFORMATION: X= Ser, Ala, Cys(mPEG), or Cys(cholesteryl)
<220> FEATURE:
<221> NAME/KEY: MOD_RES
<222> LOCATION: (12)..(12)
<223> OTHER INFORMATION: X= Lys, Cys(mPEG), or Cys(cholesteryl)
<220> FEATURE:
<221> NAME/KEY: MOD_RES
<222> LOCATION: (17)..(17)
<223> OTHER INFORMATION: X= Arg, Cys(mPEG), or Cys(cholesteryl)
<220> FEATURE:
<221> NAME/KEY: MOD_RES
<222> LOCATION: (18)..(18)
<223> OTHER INFORMATION: X= Arg, Cys(mPEG), or Cys(cholesteryl)
<220> FEATURE:
<221> NAME/KEY: MOD_RES
<222> LOCATION: (20)..(20)
<223> OTHER INFORMATION: X= Gln, Cys(mPEG), or Cys(cholesteryl)
<220> FEATURE:
<221> NAME/KEY: MOD_RES
<222> LOCATION: (21)..(21)
<223> OTHER INFORMATION: X= Asp, Cys(mPEG), or Cys(cholesteryl)
<220> FEATURE:
<221> NAME/KEY: MOD_RES
<222> LOCATION: (24)..(24)
<223> OTHER INFORMATION: X= Gln, Cys(mPEG), or Cys(cholesteryl)
<220> FEATURE:
<221> NAME/KEY: MOD_RES
<222> LOCATION: (28)..(28)
```

```
<223> OTHER INFORMATION: X= Asn, Cys(mPEG), or Cys(cholesteryl)
<220> FEATURE:
<221> NAME/KEY: MOD_RES
<222> LOCATION: (29)..(29)
<223> OTHER INFORMATION: X= Thr, Cys(mPEG), or Cys(cholesteryl)
<220> FEATURE:
<221> NAME/KEY: MOD_RES
<222> LOCATION: (36)..(36)
<223> OTHER INFORMATION: X= Ile, Cys(mPEG), or Cys(cholesteryl)
<220> FEATURE:
<221> NAME/KEY: MOD_RES
<222> LOCATION: (37)..(37)
<223> OTHER INFORMATION: X= Ala, Cys(mPEG), or Cys(cholesteryl)
<220> FEATURE:
<221> NAME/KEY: MOD_RES
<222> LOCATION: (38)..(38)
<223> OTHER INFORMATION: X= amide, carboxylate, secondary amide, Ala,
      K(palmitoyl), Cys(mPEG), Cys(cholesteryl), or any linker
      to which mPEG or cholesterol is linked with a chemical bond

<400> SEQUENCE: 164

His Ser Gln Gly Thr Phe Thr Ser Asp Tyr Xaa Xaa Tyr Leu Asp Ser
1               5                   10                  15

Xaa Xaa Ala Xaa Xaa Phe Val Xaa Trp Leu Met Xaa Xaa Lys Arg Asn
            20                  25                  30

Arg Asn Asn Xaa Xaa Xaa
            35

<210> SEQ ID NO 165
<211> LENGTH: 30
<212> TYPE: PRT
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= aib
<220> FEATURE:
<221> NAME/KEY: MOD_RES
<222> LOCATION: (3)..(3)
<223> OTHER INFORMATION: X= Asp or Gln
<220> FEATURE:
<221> NAME/KEY: MOD_RES
<222> LOCATION: (17)..(17)
<223> OTHER INFORMATION: X= Aany amino acid
<220> FEATURE:
<221> NAME/KEY: MOD_RES
<222> LOCATION: (18)..(18)
<223> OTHER INFORMATION: X= any amino acid
<220> FEATURE:
<221> NAME/KEY: MOD_RES
<222> LOCATION: (20)..(20)
<223> OTHER INFORMATION: X= Gln, Cys, or Cys(N-ethylmaleimidyl)
<220> FEATURE:
<221> NAME/KEY: MOD_RES
<222> LOCATION: (27)..(27)
<223> OTHER INFORMATION: X= Met or Met(O)
<220> FEATURE:
<221> NAME/KEY: MOD_RES
<222> LOCATION: (30)..(30)
<223> OTHER INFORMATION: X= amidated D-Lys or Lys

<400> SEQUENCE: 165

His Xaa Xaa Gly Thr Phe Thr Ser Asp Tyr Ser Lys Tyr Leu Asp Ser
1               5                   10                  15

Xaa Xaa Ala Xaa Asp Phe Val Gln Trp Leu Xaa Asn Thr Xaa
            20                  25                  30

<210> SEQ ID NO 166
<211> LENGTH: 38
<212> TYPE: PRT
```

```
<213> ORGANISM: Artificial Sequence
<220> FEATURE:
<223> OTHER INFORMATION: Synthetic peptide based on the human
      oxyntomodulin sequence
<220> FEATURE:
<221> NAME/KEY: MOD_RES
<222> LOCATION: (2)..(2)
<223> OTHER INFORMATION: X= aib
<220> FEATURE:
<221> NAME/KEY: MOD_RES
<222> LOCATION: (17)..(17)
<223> OTHER INFORMATION: X= any amino acid
<220> FEATURE:
<221> NAME/KEY: MOD_RES
<222> LOCATION: (18)..(18)
<223> OTHER INFORMATION: X= any amino acid
<220> FEATURE:
<221> NAME/KEY: MOD_RES
<222> LOCATION: (27)..(27)
<223> OTHER INFORMATION: X= Met(O)
<220> FEATURE:
<221> NAME/KEY: MOD_RES
<222> LOCATION: (38)..(38)
<223> OTHER INFORMATION: X= Cys or Cys(N-ethylmaleimidyl)

<400> SEQUENCE: 166

His Xaa Asp Gly Thr Phe Thr Ser Asp Tyr Ser Lys Tyr Leu Asp Ser
1               5                   10                  15

Xaa Xaa Ala Gln Asp Phe Val Gln Trp Leu Xaa Asn Thr Lys Arg Asn
            20                  25                  30

Arg Asn Asn Ile Ala Xaa
        35

<210> SEQ ID NO 167
<211> LENGTH: 37
<212> TYPE: PRT
<213> ORGANISM: Homo Sapiens
<220> FEATURE:
<223> OTHER INFORMATION: human oxyntomodulin sequence

<400> SEQUENCE: 167

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 168
<211> LENGTH: 29
<212> TYPE: PRT
<213> ORGANISM: Homo Sapiens
<220> FEATURE:
<223> OTHER INFORMATION: human glucagon sequence

<400> SEQUENCE: 167

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```